(12) United States Patent
Furitsu et al.

(10) Patent No.: US 9,504,746 B2
(45) Date of Patent: *Nov. 29, 2016

(54) PHARMACEUTICAL COMPOSITIONS OF 4-(3-CHLORO-4-(CYCLOPROPYLAMINO-CARBONYL)AMINOPHENOXY)-7-METHOXY-6-QUINOLINECARBOXAMIDE

(71) Applicant: Eisai R&D Management Co., Ltd., Tokyo (JP)

(72) Inventors: Hisao Furitsu, Tsukuba (JP); Yasuyuki Suzuki, Kakamigahara (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 439 days.

This patent is subject to a terminal disclaimer.

(21) Appl. No.: 13/870,507

(22) Filed: Apr. 25, 2013

(65) Prior Publication Data

US 2013/0237565 A1    Sep. 12, 2013

Related U.S. Application Data

(63) Continuation of application No. 11/662,425, filed as application No. PCT/JP2005/016941 on Sep. 14, 2005, now Pat. No. 8,969,379.

(30) Foreign Application Priority Data

Sep. 17, 2004  (JP) .................... 2004-272625

(51) Int. Cl.
*A61K 31/47* (2006.01)
*C07D 215/48* (2006.01)
(Continued)

(52) U.S. Cl.
CPC ............. *A61K 47/02* (2013.01); *A61K 9/2009* (2013.01); *A61K 9/2018* (2013.01); *A61K 9/2054* (2013.01); *A61K 9/2866* (2013.01); *A61K 31/47* (2013.01); *C07D 215/48* (2013.01)

(58) Field of Classification Search
CPC ..... C07D 214/48; A61K 31/47; A61K 47/02
See application file for complete search history.

(56) References Cited

U.S. PATENT DOCUMENTS

| 4,526,988 A | 7/1985 | Hertel |
| 4,563,417 A | 1/1986 | Albarella et al. |

(Continued)

FOREIGN PATENT DOCUMENTS

| CA | 2 361 057 | 7/2000 |
| CN | 1473041 | 2/2004 |

(Continued)

OTHER PUBLICATIONS

FMC BioPolymer; http://www.fmcbiopolymer.com/portals/pharm/content/docs/fmc_alubra_brochurefinal.pdf; accessed Mar. 16, 2015.*

(Continued)

*Primary Examiner* — Timothy Thomas
(74) *Attorney, Agent, or Firm* — Fish & Richardson P.C.

(57) ABSTRACT

A pharmaceutical composition comprising: an active ingredient consisting of 4-(3-chloro-4-(cyclopropylaminocarbonyl)aminophenoxy)-7-methoxy-6-quinolinecarboxamide, salt thereof, or solvate of the foregoing; and (i) a compound, a 5% (w/w) aqueous solution or suspension of which has a pH of 8 or more, and/or (ii) silicic acid, salt thereof, or solvate of the foregoing is a highly stable pharmaceutical composition, wherein under humidified and heated storage conditions, the decomposition of said compound is sufficiently reduced, or the gelation on the surface of the pharmaceutical composition is sufficiently inhibited.

19 Claims, 6 Drawing Sheets

(51) Int. Cl.
  *A61K 47/02* (2006.01)
  *A61K 9/20* (2006.01)
  *A61K 9/28* (2006.01)

(56) References Cited

U.S. PATENT DOCUMENTS

| | | | |
|---|---|---|---|
| 4,582,789 A | 4/1986 | Sheldon, III et al. |
| 4,742,003 A | 5/1988 | Derynck et al. |
| 4,764,454 A | 8/1988 | Ichijima et al. |
| 5,180,818 A | 1/1993 | Cech et al. |
| 5,211,951 A | 5/1993 | Sparer et al. |
| 5,445,934 A | 8/1995 | Fodor et al. |
| 5,464,826 A | 11/1995 | Grindey et al. |
| 5,487,889 A | 1/1996 | Eckert et al. |
| 5,553,037 A | 9/1996 | Tachibana |
| 5,624,937 A | 4/1997 | Reel et al. |
| 5,656,454 A | 8/1997 | Lee et al. |
| 5,658,374 A | 8/1997 | Glover |
| 5,733,913 A | 3/1998 | Blankley et al. |
| 5,747,651 A | 5/1998 | Lemischka |
| 5,750,376 A | 5/1998 | Weiss et al. |
| 5,770,599 A | 6/1998 | Gibson |
| 5,792,783 A | 8/1998 | Tang et al. |
| 5,891,996 A | 4/1999 | Mateo de Acosta del Rio et al. |
| 5,948,438 A | 9/1999 | Staniforth et al. |
| 6,027,880 A | 2/2000 | Cronin et al. |
| 6,057,100 A | 5/2000 | Heyneker |
| 6,143,764 A | 11/2000 | Kubo et al. |
| 6,156,501 A | 12/2000 | McGall et al. |
| 6,156,522 A | 12/2000 | Keay et al. |
| 6,217,866 B1 | 4/2001 | Schlessinger et al. |
| 6,261,776 B1 | 7/2001 | Pirrung et al. |
| 6,346,398 B1 | 2/2002 | Pavco et al. |
| 6,351,255 B1 | 2/2002 | Ishizuka et al. |
| 6,476,040 B1 | 11/2002 | Norris et al. |
| 6,524,583 B1 | 2/2003 | Thorpe et al. |
| 6,534,535 B1 | 3/2003 | Zhu et al. |
| 6,576,424 B2 | 6/2003 | Fodor et al. |
| 6,676,941 B2 | 1/2004 | Thorpe et al. |
| 6,797,823 B1 | 9/2004 | Kubo et al. |
| 6,811,779 B2 | 11/2004 | Rockwell et al. |
| 6,812,341 B1 | 11/2004 | Conrad |
| 6,821,987 B2 | 11/2004 | Kubo et al. |
| 7,101,663 B2 | 9/2006 | Godfrey et al. |
| 7,135,466 B2 | 11/2006 | Sakai et al. |
| 7,169,789 B2 | 1/2007 | Kubo et al. |
| 7,253,286 B2 | 8/2007 | Funahashi et al. |
| 7,435,590 B2 | 10/2008 | Komurasaki |
| 7,485,658 B2 | 2/2009 | Bolger et al. |
| 7,495,104 B2 | 2/2009 | Miwa et al. |
| 7,547,703 B2 | 6/2009 | Roth et al. |
| 7,550,483 B2 | 6/2009 | Sakaguchi et al. |
| 7,612,092 B2 | 11/2009 | Funahashi et al. |
| 7,612,208 B2 | 11/2009 | Matsushima et al. |
| 7,759,518 B2 | 7/2010 | Maderna et al. |
| 7,820,664 B2 | 10/2010 | Vernier et al. |
| 7,846,941 B2 | 12/2010 | Zhang et al. |
| 7,855,290 B2 | 12/2010 | Matsushima et al. |
| 7,863,288 B2 | 1/2011 | Ibrahim et al. |
| 7,973,160 B2 | 7/2011 | Funahashi et al. |
| 7,998,948 B2 | 8/2011 | Obaishi et al. |
| 8,044,240 B2 | 10/2011 | Dimock |
| 8,063,049 B2 | 11/2011 | Koh et al. |
| 8,101,799 B2 | 1/2012 | Maderna et al. |
| 8,143,271 B2 | 3/2012 | Ibrahim et al. |
| 8,252,842 B2 | 8/2012 | Dimock |
| 8,288,538 B2 | 10/2012 | Matsushima et al. |
| 8,372,981 B2 | 2/2013 | Funahashi et al. |
| 8,377,938 B2 | 2/2013 | Matsushima et al. |
| 8,415,469 B2 | 4/2013 | Ibrahim et al. |
| 8,466,316 B2 | 6/2013 | Dimock |
| 8,470,818 B2 | 6/2013 | Ibrahim et al. |
| 8,580,254 B2 | 11/2013 | Adam et al. |
| 8,648,116 B2 | 2/2014 | Vernier et al. |
| 8,759,577 B2 | 6/2014 | Dimock |
| 8,808,742 B2 | 8/2014 | Quart et al. |
| 2002/0040127 A1 | 4/2002 | Jiang et al. |
| 2003/0013208 A1 | 1/2003 | Jendoubi |
| 2003/0087907 A1 | 5/2003 | Kubo et al. |
| 2003/0113713 A1 | 6/2003 | Glezer et al. |
| 2003/0215523 A1 | 11/2003 | Ozawa et al. |
| 2004/0009965 A1 | 1/2004 | Collins et al. |
| 2004/0034026 A1 | 2/2004 | Wood et al. |
| 2004/0053908 A1 | 3/2004 | Funahashi et al. |
| 2004/0086915 A1 | 5/2004 | Lin et al. |
| 2004/0132727 A1 | 7/2004 | Sakai et al. |
| 2004/0132772 A1 | 7/2004 | Awad et al. |
| 2004/0152759 A1 | 8/2004 | Abrams et al. |
| 2004/0167134 A1 | 8/2004 | Bruns et al. |
| 2004/0171068 A1 | 9/2004 | Wehland et al. |
| 2004/0191254 A1 | 9/2004 | Fagin |
| 2004/0224972 A1 | 11/2004 | Ozawa et al. |
| 2004/0242506 A1 | 12/2004 | Barges Causeret et al. |
| 2004/0253205 A1* | 12/2004 | Yamamoto et al. ....... 424/78.23 |
| 2004/0259834 A1 | 12/2004 | Kasprzyk et al. |
| 2005/0014727 A1 | 1/2005 | Muller et al. |
| 2005/0049264 A1 | 3/2005 | Miwa et al. |
| 2005/0119303 A1 | 6/2005 | Wakabayashi et al. |
| 2005/0176802 A1 | 8/2005 | Tang et al. |
| 2005/0187236 A1 | 8/2005 | Tsuruoka et al. |
| 2005/0209452 A1 | 9/2005 | Bornsen et al. |
| 2005/0272688 A1 | 12/2005 | Higgins et al. |
| 2005/0277652 A1 | 12/2005 | Matsushima et al. |
| 2005/0288521 A1 | 12/2005 | Naidu et al. |
| 2006/0004017 A1 | 1/2006 | Stokes et al. |
| 2006/0004029 A1 | 1/2006 | Tsuruoka et al. |
| 2006/0057195 A1 | 3/2006 | Nonomura et al. |
| 2006/0079494 A1 | 4/2006 | Santi et al. |
| 2006/0135486 A1 | 6/2006 | Owa et al. |
| 2006/0160832 A1 | 7/2006 | Funahashi et al. |
| 2006/0178399 A1 | 8/2006 | Nishizawa et al. |
| 2006/0189629 A1 | 8/2006 | Bolger et al. |
| 2006/0292192 A1 | 12/2006 | Hasenzahl et al. |
| 2007/0004773 A1 | 1/2007 | Sakaguchi et al. |
| 2007/0027318 A1 | 2/2007 | Kubo et al. |
| 2007/0032521 A1 | 2/2007 | Moussy et al. |
| 2007/0037849 A1 | 2/2007 | Naito et al. |
| 2007/0078159 A1 | 4/2007 | Matsushima |
| 2007/0117842 A1 | 5/2007 | Arimoto et al. |
| 2007/0214604 A1 | 9/2007 | Yi |
| 2008/0207617 A1 | 8/2008 | Miwa et al. |
| 2008/0214604 A1 | 9/2008 | Furitsu et al. |
| 2008/0241835 A1 | 10/2008 | Mehraban et al. |
| 2009/0047278 A1 | 2/2009 | Owa et al. |
| 2009/0047365 A1 | 2/2009 | Owa et al. |
| 2009/0053236 A1 | 2/2009 | Yamamoto |
| 2009/0202541 A1 | 8/2009 | Bruns et al. |
| 2009/0209580 A1 | 8/2009 | Matsui |
| 2009/0247576 A1 | 10/2009 | Kamata |
| 2009/0264464 A1 | 10/2009 | Yamamoto et al. |
| 2009/0304694 A1 | 12/2009 | Oliner et al. |
| 2010/0048503 A1 | 2/2010 | Yamamoto |
| 2010/0048620 A1 | 2/2010 | Yamamoto |
| 2010/0105031 A1 | 4/2010 | Matsui et al. |
| 2010/0239688 A1 | 9/2010 | Yamamoto |
| 2010/0324087 A1 | 12/2010 | Yamamoto |
| 2011/0118470 A1 | 5/2011 | Funahashi et al. |
| 2011/0158983 A1 | 6/2011 | Bascomb et al. |
| 2011/0166174 A1 | 7/2011 | Zhang et al. |
| 2011/0293615 A1 | 12/2011 | Yamamoto |
| 2012/0022076 A1 | 1/2012 | Maderna et al. |
| 2012/0077842 A1 | 3/2012 | Bando |
| 2012/0207753 A1 | 8/2012 | Yu et al. |
| 2012/0219522 A1 | 8/2012 | Xi |
| 2012/0244209 A1 | 9/2012 | Roth et al. |
| 2012/0263677 A1 | 10/2012 | Eagle et al. |
| 2012/0283206 A1 | 11/2012 | Bruns et al. |
| 2013/0123274 A1 | 5/2013 | Nakagawa et al. |
| 2013/0296365 A1 | 11/2013 | Bando |

FOREIGN PATENT DOCUMENTS

| | | |
|---|---|---|
| CN | 1478078 | 2/2004 |
| CN | 1890220 | 1/2007 |

(56) References Cited

FOREIGN PATENT DOCUMENTS

| | | |
|---|---|---|
| CN | 101001629 | 7/2007 |
| CN | 101029022 | 9/2007 |
| CN | 101198590 | 6/2008 |
| CN | 101316590 | 12/2008 |
| CN | 101454311 | 6/2009 |
| CN | 101616671 | 12/2009 |
| CN | 102470133 | 5/2012 |
| EP | 0 405 425 | 1/1991 |
| EP | 0 602 851 | 6/1994 |
| EP | 0 684 820 | 12/1995 |
| EP | 0 712 863 | 5/1996 |
| EP | 0 795 556 | 9/1997 |
| EP | 0 837 063 | 4/1998 |
| EP | 8 860 433 | 8/1998 |
| EP | 0 870 842 | 10/1998 |
| EP | 0 930 305 | 7/1999 |
| EP | 0 930 310 | 7/1999 |
| EP | 1 029 853 | 8/2000 |
| EP | 0 543 942 | 1/2001 |
| EP | 1 153 920 | 11/2001 |
| EP | 1 411 046 | 4/2004 |
| EP | 1 415 987 | 5/2004 |
| EP | 1 447 045 | 8/2004 |
| EP | 1447405 | 8/2004 |
| EP | 1 506 962 | 2/2005 |
| EP | 1 522 540 | 4/2005 |
| EP | 1 535 910 | 6/2005 |
| EP | 1 552 833 | 7/2005 |
| EP | 1 566 379 | 8/2005 |
| EP | 1 604 665 | 12/2005 |
| EP | 1 331 005 | 4/2006 |
| EP | 1 683 785 | 7/2006 |
| EP | 1 698 623 | 9/2006 |
| EP | 1 777 218 | 4/2007 |
| EP | 1 797 877 | 6/2007 |
| EP | 1 797 881 | 6/2007 |
| EP | 1 859 793 | 11/2007 |
| EP | 1 859 797 | 11/2007 |
| EP | 1 889 836 | 2/2008 |
| EP | 1 894 918 | 3/2008 |
| EP | 1 925 676 | 5/2008 |
| EP | 1 925 941 | 5/2008 |
| EP | 1 949 902 | 7/2008 |
| EP | 1 964 837 | 9/2008 |
| EP | 2 062 886 | 5/2009 |
| EP | 2 116 246 | 11/2009 |
| EP | 2 119 707 | 11/2009 |
| EP | 2 133 094 | 12/2009 |
| EP | 2 133 095 | 12/2009 |
| EP | 2 218 712 | 8/2010 |
| EP | 2293071 | 3/2011 |
| GB | 2253848 | 9/1992 |
| GB | 2456907 | 8/2009 |
| JP | 63-028427 | 6/1988 |
| JP | 1-022874 | 1/1989 |
| JP | 2-291295 | 12/1990 |
| JP | 4-341454 | 11/1992 |
| JP | 6-153952 | 6/1994 |
| JP | 6-287148 | 10/1994 |
| JP | 7-176103 | 7/1995 |
| JP | 8-045927 | 2/1996 |
| JP | 8-048078 | 2/1996 |
| JP | 9-023885 | 1/1997 |
| JP | 9-234074 | 9/1997 |
| JP | 3088018 | 6/1998 |
| JP | 11-501343 | 2/1999 |
| JP | 11-143429 | 5/1999 |
| JP | 11-158149 | 6/1999 |
| JP | 11-322596 | 11/1999 |
| JP | 3040486 | 5/2000 |
| JP | 3420549 | 10/2000 |
| JP | 2000-325080 | 11/2000 |
| JP | 2001-131071 | 5/2001 |
| JP | 2002-003365 | 1/2002 |
| JP | 2002-114710 | 4/2002 |
| JP | 2002-536414 | 10/2002 |
| JP | 2003-012668 | 1/2003 |
| JP | 2003-026576 | 1/2003 |
| JP | 2003-033472 | 2/2003 |
| JP | 2003-525595 | 9/2003 |
| JP | 2004-513964 | 5/2004 |
| JP | 2004-155773 | 6/2004 |
| JP | 2004-531549 | 10/2004 |
| JP | 2005-272474 | 10/2004 |
| JP | 2005-501074 | 1/2005 |
| JP | 2005-504111 | 2/2005 |
| JP | 2005-520834 | 7/2005 |
| JP | 3712393 | 11/2005 |
| JP | 2006-508981 | 3/2006 |
| JP | 2008-546797 | 12/2008 |
| JP | 2009-132660 | 6/2009 |
| JP | 2010-535233 | 11/2010 |
| KR | 10-0589032 | 11/2005 |
| RU | 2328489 | 7/2008 |
| RU | 2362771 | 7/2009 |
| WO | WO 92/20642 | 11/1992 |
| WO | WO 94/09010 | 4/1994 |
| WO | WO 95/15758 | 6/1995 |
| WO | WO 95/17181 | 6/1995 |
| WO | WO 95/19774 | 7/1995 |
| WO | WO 96/09294 | 3/1996 |
| WO | WO 96/26997 | 9/1996 |
| WO | WO 96/30347 | 10/1996 |
| WO | WO 96/33980 | 10/1996 |
| WO | WO 96/39145 | 12/1996 |
| WO | WO 96/40142 | 12/1996 |
| WO | WO 97/03069 | 1/1997 |
| WO | WO 97/13760 | 4/1997 |
| WO | WO 97/13771 | 4/1997 |
| WO | WO 97/17329 | 5/1997 |
| WO | WO 97/21437 | 6/1997 |
| WO | WO 97/38984 | 10/1997 |
| WO | WO 97/48693 | 12/1997 |
| WO | WO 98/00134 | 1/1998 |
| WO | WO 98/02434 | 1/1998 |
| WO | WO 98/02437 | 1/1998 |
| WO | WO 98/02438 | 1/1998 |
| WO | WO 98/13350 | 4/1998 |
| WO | WO 98/14437 | 4/1998 |
| WO | WO 98/23613 | 6/1998 |
| WO | WO 98/32436 | 7/1998 |
| WO | WO 98/35958 | 8/1998 |
| WO | WO 98/37079 | 8/1998 |
| WO | WO 98/50346 | 11/1998 |
| WO | WO 98/52558 | 11/1998 |
| WO | WO 99/00357 | 1/1999 |
| WO | WO 99/32106 | 7/1999 |
| WO | WO 99/32110 | 7/1999 |
| WO | WO 99/32111 | 7/1999 |
| WO | WO 99/32436 | 7/1999 |
| WO | WO 99/35132 | 7/1999 |
| WO | WO 99/35146 | 7/1999 |
| WO | WO 99/43654 | 9/1999 |
| WO | WO 99/62890 | 12/1999 |
| WO | WO 00/31048 | 6/2000 |
| WO | WO 00/42012 | 7/2000 |
| WO | WO 00/43366 | 7/2000 |
| WO | WO 00/43384 | 7/2000 |
| WO | WO 00/44728 | 8/2000 |
| WO | WO 00/47212 | 8/2000 |
| WO | WO 00/50405 | 8/2000 |
| WO | WO 00/71097 | 11/2000 |
| WO | WO 01/02369 | 1/2001 |
| WO | WO 01/23375 | 4/2001 |
| WO | WO 01/27081 | 4/2001 |
| WO | WO 01/32926 | 5/2001 |
| WO | WO 01/36403 | 5/2001 |
| WO | WO 01/40217 | 6/2001 |
| WO | WO 01/45689 | 6/2001 |
| WO | WO 01/47890 | 7/2001 |
| WO | WO 01/47931 | 7/2001 |
| WO | WO 01/60814 | 8/2001 |
| WO | WO 02/16348 | 2/2002 |
| WO | WO 02/32872 | 4/2002 |

(56) References Cited

FOREIGN PATENT DOCUMENTS

| WO | WO 02/36117 | 5/2002 |
|---|---|---|
| WO | WO 02/41882 | 5/2002 |
| WO | WO 02/44156 | 6/2002 |
| WO | WO 02/072578 | 9/2002 |
| WO | WO 02/080975 | 10/2002 |
| WO | WO 02/088110 | 11/2002 |
| WO | WO 02/092091 | 11/2002 |
| WO | WO 03/006462 | 1/2003 |
| WO | WO 03/013529 | 2/2003 |
| WO | WO 03/027102 | 3/2003 |
| WO | WO 03/028711 | 4/2003 |
| WO | WO 03/033472 | 4/2003 |
| WO | WO 03/050090 | 6/2003 |
| WO | WO 03/074045 | 9/2003 |
| WO | WO 03/079020 | 9/2003 |
| WO | WO 2004/006862 | 1/2004 |
| WO | WO 2004/020434 | 3/2004 |
| WO | WO 2004/032872 | 4/2004 |
| WO | WO 2004/032937 | 4/2004 |
| WO | WO 2004/035052 | 4/2004 |
| WO | WO 2004/039782 | 5/2004 |
| WO | WO 2004/041308 | 5/2004 |
| WO | WO 2004/043472 | 5/2004 |
| WO | WO 2004/064730 | 8/2004 |
| WO | WO 2004/078144 | 9/2004 |
| WO | WO 2004/080462 | 9/2004 |
| WO | WO 2004/101526 | 11/2004 |
| WO | WO 2005/004870 | 1/2005 |
| WO | WO 2005/021537 | 3/2005 |
| WO | WO 2005/027972 | 3/2005 |
| WO | WO 2005/030140 | 4/2005 |
| WO | WO 2005/044788 | 5/2005 |
| WO | WO 2005/051366 | 6/2005 |
| WO | WO 2005/056764 | 6/2005 |
| WO | WO 2005/063713 | 7/2005 |
| WO | WO 2005/082854 | 9/2005 |
| WO | WO 2005/092896 | 10/2005 |
| WO | WO 2005/117887 | 12/2005 |
| WO | WO 2006/030826 | 3/2006 |
| WO | WO 2006/030941 | 3/2006 |
| WO | WO 2006/030947 | 3/2006 |
| WO | WO 2006/036941 | 4/2006 |
| WO | WO 2006/062984 | 6/2006 |
| WO | WO 2006/090930 | 8/2006 |
| WO | WO 2006/090931 | 8/2006 |
| WO | WO 2006/137474 | 12/2006 |
| WO | WO 2007/000347 | 1/2007 |
| WO | WO 2007/014335 | 2/2007 |
| WO | WO 2007/015569 | 2/2007 |
| WO | WO 2007/015578 | 2/2007 |
| WO | WO 2007/023768 | 3/2007 |
| WO | WO 2007/040565 | 4/2007 |
| WO | WO 2007/052849 | 5/2007 |
| WO | WO 2007/052850 | 5/2007 |
| WO | WO 2007/061127 | 5/2007 |
| WO | WO 2007/061130 | 5/2007 |
| WO | WO 2007/136103 | 11/2007 |
| WO | WO 2008/023698 | 2/2008 |
| WO | WO 2008/026748 | 3/2008 |
| WO | WO 2008/088088 | 7/2008 |
| WO | WO 2008/093855 | 8/2008 |
| WO | WO 2008/155387 | 12/2008 |
| WO | WO 2009/018238 | 2/2009 |
| WO | WO 2009/060945 | 5/2009 |
| WO | WO 2009/077874 | 6/2009 |
| WO | WO 2009/096377 | 8/2009 |
| WO | WO 2009/140549 | 11/2009 |
| WO | WO 2009/150256 | 12/2009 |
| WO | WO 2010/006225 | 1/2010 |
| WO | WO 2010/048304 | 4/2010 |
| WO | WO 2011/017583 | 2/2011 |
| WO | WO 2011/022335 | 2/2011 |
| WO | WO 2011/162343 | 12/2011 |
| WO | WO 2012/166899 | 12/2012 |

OTHER PUBLICATIONS

Patel et al.; "The effect of excipients on the stability of levothyroxine sodium pentahydrate tablets"; 2003; International Journal of Pharmaceutics; 264: 35-43.*
Amendment and RCE submission documents filed in U.S. Appl. No. 12/039,381, dated Oct. 23, 2013, 13 pages.
Amendment and Response filed in U.S. Appl. No. 11/997,543, dated Dec. 19, 2013, 38 pages.
Amendment filed in BR App. Ser. No. BR112012032462-4, dated Nov. 4, 2013, 21 pages (with English translation).
Amendment filed in EP App. Ser. No. 12793322.4, dated Nov. 28, 2013, 6 pages.
Amendment filed in KR App. Ser. No. 10-2008-7029472, dated Nov. 20, 2013, 81 pages (with English translation).
Amendment filed in KR App. Ser. No. 10-2013-7020616, dated Nov. 22, 2013, 22 pages (with English translation).
International Preliminary Report on Patentability in International App. Ser. No. PCT/JP2012/060279, dated Oct. 23, 2013, 11 pages.
International Preliminary Report on Patentability in International App. Ser. No. PCT/JP2012/062509, dated Nov. 28, 2013, 11 pages.
Notice of Allowance in IL App. Ser. No. 200090, dated Nov. 18, 2013, 5 pages (with English translation).
Notice of Allowance in JP App. Ser. No. P2009-551518, dated Oct. 22, 2013, 5 pages (with English translation).
Notice of Allowance in KR App. Ser. No. 10-2008-7013685, dated Nov. 29, 2013, 3 pages (with English translation).
Notice of Allowance in U.S. Appl. No. 12/439,339, dated Nov. 7, 2013, 64 pages.
Notice of Allowance in U.S. Appl. No. 12/524,754, dated Nov. 22, 2013, 12 pages.
Office Action in CA App. Ser. No. 2652442, dated Oct. 4, 2013, 2 pages.
Office Action in CN App. Ser. No. 200680020317.5, dated Nov. 28, 2013, 8 pages (with English translation).
Office Action in CN App. Ser. No. 201180030568.2, dated Oct. 12, 2013, 11 pages (with English translation.
Office Action in CO App. Ser. No. 12-022608, dated Dec. 17, 2013, 12 pages (with English translation).
Office Action in IL App. Ser. No. 205512, dated Oct. 28, 2013, 5 pages (with English translation).
Office Action in IL App. Ser. No. 207089, dated Nov. 25, 2013, 6 pages (with English translation).
Office Action in IN App. Ser. No. 1571/CHENP/2007, dated Oct. 23, 2013, 2 pages.
Office Action in IN App. Ser. No. 1571/CHENP/2007, Dec. 9, 2013, 2 pages.
Office Action in MX App. Ser. No. MX/a/2010/008187, dated Dec. 5, 2013, 8 pages (with English translation).
Office Action in MX App. Ser. No. MX/a/2012/002011, dated Nov. 21, 2013, 8 pages (with English translation).
Office Action in U.S. Appl. No. 13/238,085, dated Nov. 12, 2013, 74 pages.
Office Action in VN App. Ser. No. 1-2011-03484, dated Dec. 31, 2013, 2 pages (with English translation).
Preliminary Amendment filed in EP App. Ser. No. 12786619.2, dated Nov. 13, 2013, 7 pages.
Preliminary Amendment filed in U.S. Appl. No. 14/117,276, dated Nov. 12, 2013, 11 pages.
Preliminary Amendment filed in U.S. Appl. No. 14/122,339, dated Nov. 26, 2013, 10 pages.
Response filed in CA App. Ser. No. 2652442, dated Jan. 8, 2014, 5 pages.
Response filed in CO App. Ser. No. 12-022608, dated Nov. 13, 2013, 13 pages (with English translation).
Response filed in KR App. Ser. No. 10-2009-7005657, dated Nov. 21, 2013, 46 pages (with English translation).
Response filed in MX App. Ser. No. MX/a/2010/008187, dated Nov. 4, 2013, 21 pages (with English translation).
Response filed in PH App. Ser. No. 1-2011-502441, dated Nov. 4, 2013, 28 pages.

(56) References Cited

OTHER PUBLICATIONS

Submission documents re RCE filed in U.S. Appl. No. 11/997,719, dated Dec. 11, 2013, 10 pages.
Submission documents re RCE filed in U.S. Appl. No. 13/083,338, dated Dec. 2, 2013, 5 pages.
Submission documents re RCE filed in U.S. Appl. No. 13/205,328, dated Dec. 30, 2013, 1 page.
Submission documents re RCE filed in U.S. Appl. No. 13/624,278, dated Dec. 13, 2013, 10 pages.
Voluntary Amendment filed in CA App. Ser. No. 2802644, dated Nov. 22, 2013, 25 pages.
Wang, "Drugs of Today, Everolimus in renal cell carcinoma," Journals on the Web, Aug. 2010, vol. 46, issue 8, 1 page (abstract only).
Amended Claims in BR App. Ser. No. BR112012003592-4, dated Oct. 23, 2014, 12 pages (with English translation).
Amended Drawing in IL App. Ser. No. 217197, dated Oct. 22, 2014, 4 pages (with English translation).
Amended Drawing in PH App. Ser. No. 1-011-502441, dated Oct. 17, 2014, 2 pages.
Amended drawings in EP App. Ser. No. 10809938.3, dated Nov. 11, 2014, 14 pages.
Amended set of Claims in EP App. Ser. No. 11798224.9, dated Sep. 19, 2014, 53 pages.
Amendment and Request for Continued Examiner (RCE) in U.S. Appl. No. 13/083,338, dated Oct. 10, 2014, 5 pages.
Amendment in IN App. Ser. No. 2371/CHENP/2012, dated Oct. 30, 2014, 2 pages.
Amendment in KR App. Ser. No. 10-2010-7011023, dated Oct. 21, 2014, 31 pages (with English translation).
Amendment in KR App. Ser. No. 10-2010-7018835, dated Dec. 12, 2014, 18 pages (with English translation).
Amendment in KR App. Ser. No. 10-2012-7003846, dated Nov. 26, 2014, 20 pages (with English translation).
Amendment in TW App. Ser. No. 100104281, dated Oct. 22, 2014, 8 pages (with English translation).
Amendment in U.S. Appl. No. 11/662,425, dated Sep. 2, 2014, 6 pages.
Anderson et al, "Clinical, Safety, and Economic Evidence in Radioactive Iodine-Refractory Differentiated Thyroid Cancer: A Systematic Literature Review", Thyroid, 23(4):392-407, 2013.
Bajwa et al., "Antimalarials. 1. Heterocyclic Analogs of N-Substituted Naphthalenebisoxazines," J Med Chem., 16(2):134-138, Aug. 9, 1972.
Brose et al, "Sorafenib in radioactive iodine-refractory, locally advanced or metastatic differentiated thyroid cancer: a randomised, double-blind, phase 3 trial", The Lancet, 384:319-328, Jul. 26, 2014.
Burwell, Jr, "The Cleavage of Ethers," Chem Rev., 54(4):615-685, Feb. 26, 1954.
Carey, "Organic Chemistry 4e: Chapter 24: Phenols," McGraw Hill, htip://www.mhhe.com/physsci/chemistry/carey/student/olc/ch24reactionsalethers.html. Accessed Oct. 3, 2014, 2000, 4 pages.
Elisei et al., "Subgroup Analyses of a Phase 3 Multicenter, Double-Blind, Placebo-Controlled Trial of Lenvatinib (E7080) in Patients with 13II-Refractory Differentiated Thyroid Cancer," Poster, No. 1033P, presented at European Society for Medical Oncology 2014 Congress, Sep. 26-30, 2014, 1 page.
Erdem et al, "Correlation of E-cadherin, VEGF, COX-2 expression to prognostic parameters in papillary thyroid carcinoma", Experimental Mole Pathol., 90:312-317, Feb. 16, 2011.
Extended Search Report in EP App. Ser. No. 12786619.2, dated Nov. 25, 2014, 6 pages.
Gild et al, "Multikinase inhibitors: a new option for the treatment of thyroid cancer", Nature Reviews Endocrinol., 7:617-624, Oct. 2011.
Kremer, "Lenvatinib Advisory Board", The presentation document, American Society of Clinical Oncology, Annual meeting 2014, May 31, 2014, 138 pages.
Notice of Allowance in AU App. Ser. No. 2010285740, dated Nov. 19, 2014, 1 page.
Notice of Allowance in CA App. Ser. No. 2771403, dated Oct. 22, 2014, 1 page.
Notice of Allowance in CN App. Ser. No. 201180030568.2, dated Sep. 9, 2014, 4 pages (with English translation).
Notice of Allowance in EP App. Ser. No. 08704376.6, dated Aug. 19, 2014, 62 pages.
Notice of Allowance in IL App. Ser. No. 207089, dated Nov. 10, 2014, 5 pages (with English translation).
Notice of Allowance in JP App. Ser. No. P2009-540099, dated Oct. 21, 2014, 6 pages (with English translation).
Notice of Allowance in KR App. Ser. No. 10-2008-7029472, dated Sep. 16, 2014, 3 pages (with English translation).
Notice of Allowance in KR App. Ser. No. 10-2009-7005657, dated Sep. 19, 2014, 3 pages (with English translation).
Notice of Allowance in U.S. Appl. No. 11/662,425, dated Oct. 21, 2014, 49 pages.
Notice of Allowance in U.S. Appl. No. 11/997,719, dated Dec. 2, 2014, 21 pages.
Notice of Allowance in U.S. Appl. No. 12/524,754, dated Sep. 18, 2014, 35 pages.
Notice of Allowance in U.S. Appl. No. 12/741,682, dated Oct. 6, 2014, 11 pages.
Notice of Allowance in U.S. Appl. No. 13/083,338, dated Dec. 5, 2014, 19 pages.
Notice of Allowance in U.S. Appl. No. 13/624,278, dated Oct. 31, 2014, 14 pages.
Notice of Allowance in U.S. Appl. No. 13/805,826, dated Dec. 17, 2014, 15 pages.
Notice of Allowance in U.S. Appl. No. 14/002,018, dated Oct. 24, 2014, 70 pages.
Notice of Appeal in U.S. Appl. No. 11/662,425, dated Sep. 5, 2014, 11 pages.
Notice of Appeal in U.S. Appl. No. 12/039,381, dated Aug. 29, 2014, 9 pages.
Office Action in AU App. Ser. No. 2010285740, dated Aug. 22, 2014, 3 pages.
Office Action in CA App. Ser. No. 2704000, dated Nov. 4, 2014, 3 pages.
Office Action in CL App. Ser. No. 2012-00412, dated Sep. 3, 2014, 22 pages (with English translation).
Office Action in CN App. Ser. No. 201280010898.X, dated Aug. 11, 2014, 14 pages (with English translation).
Office Action in EP App. Ser. No. 03791389.4, dated Dec. 2, 2014, 5 pages.
Office Action in EP App. Ser. No. 07743994.1, dated Sep. 9, 2014, 8 pages.
Office Action in EP App. Ser. No. 10809938.3, dated Oct. 16, 2014, 5 pages.
Office Action in IL App. Ser. 205512, dated Sep. 22, 2014, 5 pages (with English translation).
Office Action in IL App. Ser. No. 217197, dated Oct. 22, 2014, 4 pages (with English translation).
Office Action in KR App. Ser. No. 10-2010-7011023, dated Sep. 3, 2014, 14 pages (with English translation).
Office Action in KR App. Ser. No. 10-2010-7018835, dated Sep. 30, 2014, 6 pages (with English translation).
Office Action in KR App. Ser. No. 10-2012-7003846, dated Oct. 7, 2014, 7 pages (with English translation).
Office Action in MX App. Ser. No. MX/a/2012/014776, dated Oct. 15, 2014, 15 pages (with English translation).
Office Action in MX App. Ser. No. MX/a/2013/009931, dated Sep. 5, 2014, 15 pages (with English translation).
Office Action in RU App. Ser. No. 2012103471, dated Sep. 16, 2014, 5 pages (with English translation).
Office Action in U.S. Appl. No. 11/662,425, dated Sep. 17, 2014, 3 pages.
Office Action in U.S. Appl. No. 13/805,826, dated Sep. 23, 2014, 25 pages.
Office Action in U.S. Appl. No. 13/923,858, dated Dec. 5, 2014, 67 pages.
Official Notification re Decision on Petition in U.S. Appl. No. 11/997,719, dated Sep. 23, 2014, 1 page.

(56) References Cited

OTHER PUBLICATIONS

Official Notification re Interview Summary in U.S. Appl. No. 13/805,826, dated Dec. 1, 2014, 3 pages.
Official Notification re Interview Summary in U.S. Appl. No. 14/002,018, dated Oct. 6, 2014, 2 pages.
Pacini, "38th Annual Meeting of the European Thyroid Association", European Thyroid Association, Santiago de Compostela, Spain, Aug. 15, 2014, p. 73-p. 226.
Reply to final office action in U.S. Appl. No. 13/805,826, dated Nov. 26, 2014, 7 pages.
Reply to Final Office Action in U.S. Appl. No. 14/002,018, dated Oct. 1, 2014, 6 pages.
Request for Continued Examination (RCE) in U.S. Appl. No. 13/624,278, dated Sep. 24, 2014, 1 page.
Request for Continued Examination (RCE) in U.S. Appl. No. 11/997,719, dated Aug. 29, 2014, 1 page.
Response in EP App. Ser. No. 12774278.1, dated Oct. 13, 2014, 4 pages.
Response to office action in AU App. Ser. No. 2010285740, dated Oct. 28, 2014, 14 pages.
Response to Office Action in CA App. Ser. No. 2771403, dated Sep. 10, 2014, 11 pages.
Response to office action in CN App. Ser. No. 201280010898.X, dated Nov. 25, 2014, 7 pages (with English translation).
Response to office action in IL App. Ser. No. 217197, dated Nov. 26, 2014, 7 pages (with English translation).
Response to office action in RU App. Ser. No. 2012103471, dated Nov. 18, 2014, 17 pages (with English translation).
Robinson et al, "Characterization Of Tumor Size Changes Over Time From The Phase 3 Study Of (E7080) Lenvatinib In Differentiated Cancer Of The Thyroid (Select)", The Poster, No. 1031P, presented at European Society for Medical Oncology 2014 Congress, Sep. 26-30, 2014, 1 page.
Search Report in EP App. Ser. No. 12786619.2, dated Dec. 15, 2014, 6 pages.
Sennino and McDonald, "Controlling escape from angiogenesis inhibitors", Nature Rev Cancer, 12:699-709, Oct. 2012.
Submission Document in CL App. Ser. No. 2012-00412, dated Aug. 12, 2014, 2 pages (with English translation).
Submission Document in MX App. Ser. No. MX/a/2014/010594, dated Sep. 4, 2014, 70 pages (with English translation).
Submission Document in MY App. Ser. No. PI2011700172, dated Nov. 4, 2014, 3 pages.
Submission Document re figures in AR App. Ser. No. P110100513, dated Oct. 22, 2014, 3 pages (with English translation).
Tahara et al, "Comprehensive Analysis of Serum Biomarkers and Tumor Gene Mutations Associated With Clinical Outcomes in the Phase 3 Study of (E7080) Lenvatinib in Differentiated Cancer of the Thyroid (SELECT)", The presentation document, presented at European Society for Medical Oncology 2014 Congress, Sep. 26-30, 2014, 24 pages.
Takahashi et al, "Phase II Study Of Lenvatinib, A Multitargeted Tyrosine Kinase Inhibitor, In Patients With All Histologic Subtypes Of Advanced Thyroid Cancer (Differentiated, Medullary, and Anaplastic)", The Poster, presented at the European Society for Medical Oncology 2014 Congress, Sep. 26-30, 2014, 1 page.
Tamura et al., "Molecular Characterization of Undifferentiated-Type Gastric Carcinoma," Laboratory Investigation, 81(4):593-598, Apr. 2001.
Tohyama et al, "Antitumor Activity of Lenvatinib (E7080): An Angiogenesis Inhibitor That Targets Multiple Receptor Tyrosine Kinases in Preclinical Human Thyroid Cancer Models," J Thyroid Res, 2014:1-13, Sep. 10, 2014.
Voluntary Amendment in ID App. Ser. No. W-00201201031, dated Nov. 5, 2014, 2 pages (with English translation).
Voluntary Amendment in MX App. Ser. No. MX/a/2014/010594, dated Oct. 23, 2014, 4 pages (with English translation).
Wells Jr et al, "Vandetanib in Patients With Locally Advanced or Metastatic Medullary Thyroid Cancer: A Randomized, Double-Blind Phase III Trial", J Clinical Oncol., 30(2):134-141, Jan. 10, 2012, corrections published Aug. 20, 2013, p. 3049.
Wirth et al, "Treatment-Emergent Hypertension And Efficacy In The Phase 3 Study Of (E7080) Lenvatinib In Differentiated Cancer Of The Thyroid (Select)", The Poster, No. 1030P, presented at the European Society for Medical Oncology 2014 Congress, Sep. 26-30, 2014, 1 page.
Zhong et al., "Mechanisms underlying the synergistic effect of SU5416 and cisplatin on cytotoxicity in human ovarian tumor cells," Inter'l J Oncol., 25(2):445-451, 2001.
Amended claims in EP App. Ser. No. 04807580.8, dated Jun. 16, 2014, 7 pages.
Amended Claims in MY App. Ser. No. PI2011700172, dated in Jul. 3, 2014, 15 pages.
Amendment filed in KR App. Ser. No. 10-2008-7029472, dated May 1, 2014, 14 pages (with English translation).
Amendment filed in KR App. Ser. No. 10-2009-7005657, dated May 7, 2014, 15 pages (with English translation).
Besson et al., "PTEN/MMAC1/TEP1 in signal transduction and tumorigenesis," EP J Biochem., 1999, 263:605-611.
Comments re Board of Appeal in EP App. Ser. No. 04807580.8, dated Jul. 7, 2014, 3 pages.
Dankort et al., "Braf V660E cooperates with Pten loss to induce metastic melanoma," Nature Genetics, 2009, 41(5):544-552.
Davies et al., "Mutations of the BRAF gene in human cancer," Nature, Jun. 27, 2002, 417:949-954.
Finn et al., "A multicenter, open-label, phase 3 trial to compare the efficacy and safety of lenvatinib (E7080) versus sorafenib in first-line treatment of subjects with unresectable hepatocellular carinoma," Am Soc Clin Oncol Annual Meeting Abstract, May 31, 2014, 5 pages.
Fujii et al., "Angiogenesis Inhibitor/Kekkan Shinsei Sogaiyaku," Clin Gastroenterol., May 25, 2004, 19:220-227.
Havel et al., "E7080 (lenvatinib) in addition to best supportive care (BSC) versus (BSC) alone in third-line or greater nonsquamous, non-small cell lung cancer (NSCLC)," Am Soc Clin Oncol Annual Meeting Abstract, May 31, 2014, abstract 8043, 4 pages.
Ikota et al., "E7080, a Multi-Tyrosine Kinase Inhibitor, Suppresses the Progression of Malignant Pleural Mesothelioma with Different Proangiogenic Cytokine Production Profiles," Clin Cancer Res., Nov. 24, 2009, 15(23):7229-7237.
International Preliminary Report on Patentability in PCT App. Ser. No. PCT/US2012/040183, dated Apr. 3, 2014, 9 pages.
Matsui et al., "Multi-Kinase Inhibitor E7080 Suppresses Lymph Node and Lung Metastases of Human Mammary Breast Tumor MDA-MB-231 via Inhibition of Vascular Endothelial Growth Factor-Receptor (VEGF-R) 2 and VEGF-R3 Kinase," Clin Cancer Res., 2008, 14:5459-5465.
Matsui et al., "Mechanism of antitumor activity of E7080, a selective VEGFR and FGFR tyrosine kinase inhibitor (TKI), in combination with selective mutant BRAF inhibition," J Clin Oncol., May 20, 2011, 29(15), Suppl., Asco Meeting Abstracts, Part 1, Abstract No. 8567, 2 pages.
Nakagawa et al., "E7050: A dual c-Met and VEGFR-2 tyrosine kinase inhibitor promotes tumor regression and prolongs survival in mouse xengraft models," Cancer Sci., Jan. 2010, 101(1):210-215.
Nakazawa et al., "Maximizing the efficacy of anti-angiogenesis cancer therapy: A multi-targeting strategy by tyrosine kinase inhibitors," AACR Annual Meeting 2014, Presentation Abstract and Poster, Apr. 5-9, 2014, 2 pages.
Nakazawa, "Combination strategy of lenvatinib: Maximizing its anti-angiogenesis efficacy," Tsukuba Res Laboratory, Eisai Co., Ltd., Ibaraki, Japan, Jun. 27, 2014, 10 pages.
Notice of Allowance in CA App. Ser. No. 2652442, dated Apr. 16, 2014, 1 page.
Notice of Allowance in IL App. Ser. No. 195282, dated Aug. 11, 2014, 5 pages (with English translation).
Notice of Allowance in KR App. Ser. No. 10-2009-7017694, dated Jul. 28, 2014, 3 pages (with English translation).
Notice of Allowance in MX App. Ser. No. MX/a/2010/008187, dated Jul. 17, 2014, 3 pages (with English translation).
Notice of Allowance in UA App. Ser. No. a201203132, dated Mar. 21, 2014, 6 pages.

(56) References Cited

OTHER PUBLICATIONS

Notice of Allowance in U.S. Appl. No. 11/997,719, dated Jun. 5, 2014, 14 pages.
Notice of Allowance in U.S. Appl. No. 12/439,339, dated Apr. 1, 2014, 17 pages.
Notice of Allowance in U.S. Appl. No. 12/741,682, dated May 15, 2014, 13 pages.
Notice of Allowance in U.S. Appl. No. 13/083,338, dated Jul. 10, 2014, 22 pages.
Notice of Allowance in U.S. Appl. No. 13/205,328, dated May 8, 2014, 10 pages.
Notice of Allowance in U.S. Appl. No. 13/624,278, dated Jun. 25, 2014, 57 pages.
Notice of Allowance in VN App. Ser. No. 1-2011-03484, dated Apr. 28, 2014, 2 pages.
Office Action in CA App. Ser. No. 2771403, dated Jul. 16, 2014, 3 pages.
Office Action in CN App. Ser. No. 201180030568.2, dated Mar. 24, 2014, 8 pages (with English translation).
Office Action in EP App. Ser. No. 03791389.4, dated Jun. 10, 2014, 4 pages.
Office Action in EP App. Ser. No. 08846814.5, dated Jun. 4, 2014, 4 pages.
Office Action in JP App. Ser. No. P2009-540099, dated Mar. 25, 2014, 6 pages (with English translation).
Office Action in KR App. Ser. No. 10-2008-7029472, dated Mar. 28, 2014, 6 pages (with English translation).
Office Action in KR App. Ser. No. 10-2009-7005657, dated Mar. 28, 2014, 6 pages (with English translation).
Office Action in MX App. Ser. No. MX/a/2010/008187, dated Apr. 28, 2014, 4 pages (with English translation).
Office Action in MX App. Ser. No. MX/a/2012/002011, dated Apr. 28, 2014, 10 pages (with English translation).
Office Action in MX App. Ser. No. MX/a/2012/014776, dated Apr. 4, 2014, 22 pages (with English Translation).
Office Action in RU App. Ser. No. 2012103471, dated May 20, 2014, 5 pages (with English translation).
Office Action in U.S. Appl. No. 11/662,425, dated Jun. 5, 2014, 30 pages.
Office Action in U.S. Appl. No. 12/039,381, dated May 29, 2014, 78 pages.
Office Action in U.S. Appl. No. 12/864,817, dated Aug. 15, 2014, 79 pages.
Office Action in U.S. Appl. No. 13/805,826, dated Apr. 2, 2014, 8 pages.
Office Action in U.S. Appl. No. 13/805,826, dated Jul. 1, 2014, 88 pages.
Office Action in U.S. Appl. No. 13/923,858, dated Apr. 18, 2014, 64 pages.
Office Action in U.S. Appl. No. 14/002,018, dated Apr. 14, 2014, 28 pages.
Office Action in U.S. Appl. No. 14/002,018, dated Jul. 25, 2014, 14 pages.
Office Action in U.S. Appl. No. 14/002,018, dated Jun. 9, 2014, 19 pages.
Official Notification in EP App. Ser. No. 04807580.8, dated Jun. 16, 2014, 1 pages.
Official Notification in EP App. Ser. No. 04807580.8, dated Jun. 27, 2014, 17 pages.
Request for accelerated examination in KR App. Ser. No. 10-2012-7003846, dated Jun. 18, 2014, 29 pages (with English translation).
Response filed in VN App. Ser. No. 1-2011-03484, dated Feb. 28, 2014, 40 pages (with English translation).
Response to Notice of Allowance in U.S. Appl. No. 13/205,328, dated Jul. 8, 2014, 7 pages.
Response to Office Action filed in EP App. Ser. No. 04807580.8, dated May 16, 2014, 13 pages.
Response to Office Action in CA App. Ser. No. 2676796, dated Jun. 27, 2014, 18 pages.
Response to Office Action in CN App. Ser. No. 201180030568.2 filed on May 14, 2014, 10 pages (with English translation).
Response to Office Action in EP App. Ser. No. 03791389.4, dated Jul. 25, 2014, 75 pages.
Response to Office Action in EP App. Ser. No. 08704376.6, dated Apr. 30, 2014, 73 pages.
Response to Office Action in EP App. Ser. No. 08846814.5, dated Jul. 24, 2014, 71 pages.
Response to Office Action in JP App. Ser. No. P2009-540099, dated Apr. 28, 2014, 9 pages (with English Translation).
Response to Office Action in MX App. Ser. No. MX/a/2010/008187, dated Jun. 25, 2014, 5 pages (with English translation).
Response to Office Action in MX App. Ser. No. MX/a/2012/014776, dated Jun. 20, 2014, 16 pages (with English translation).
Response to Office Action in RU App. Ser. No. 2012103471, dated Jul. 21, 2014, 7 pages (with English translation).
Response to Office Action in SG App. Ser. No. 201108602-2, dated May 22, 2014, 37 pages.
Response to Office Action in U.S. Appl. No. 11/662,425, filed May 20, 2014, 8 pages.
Response to Office Action in U.S. Appl. No. 12/039,381, dated Apr. 3, 2014, 7 pages.
Response to Office Action in U.S. Appl. No. 13/805,826, dated Aug. 8, 2014, 9 pages.
Response to Office Action in U.S. Appl. No. 13/923,858, dated Aug. 8, 2014, 24 pages.
Response to Office Action in U.S. Appl. No. 14/002,018, dated Jul. 18, 2014, 8 pages.
Response to Office Action in U.S. Appl. No. 14/002,018, filed May 28, 2014, 7 pages.
Response to Restriction Response in U.S. Appl. No. 13/805,826, dated Jun. 2, 2014, 2 pages.
Schlumberger et al., "A phase 3, multicenter, double-blind, placebo-controlled trial of lenvatinib (E7080) in patients with 131I-refractory differentiated thyroid cancer (SELECT)," Am Soc Clin Oncol., Annual Meeting Abstract LBA6008, 2012, 4 pages.
Search Report in EP App. Ser. No. 09705712.9, dated Aug. 7, 2014, 6 pages.
Search Report in EP App. Ser. No. 12774278.1, dated Aug. 14, 2014, 8 pages.
Shirai et al., "Role of low-substituted hydroxypropylcellulose in dissociation and bioavalability of novel fine granule system for masking bitter taste," Biol. Pharm. Bull, 17(3): 427-431 (1994).
Shumaker et al., "Effect of lenvatinib (E7080) on the QTc interval: results from a thorough QT study in healthy volunteers," Cancer Chemother Pharmacol., published online Mar. 23, 2014, 9 pages.
Sondergaard et al., Differential sensitivity of melanoma cell lines with $BRAF^{V600E}$ mutation to the specific Raf inhibitor PLX4032, J Translational Med., 2010, 8:39, 11 pages.
Submission Document re RCE in U.S. Appl. No. 12/741,682, dated Aug. 14, 2014, 1 page.
Submission Documents re RCE filed in U.S. Appl. No. 12/524,754, dated May 13, 2014, 1 page.
Submission Documents re RCE filed in U.S. Appl. No. 12/741,682, dated May 6, 2014, 1 page.
Submission Documents re RCE filed in U.S. Appl. No. 13/083,338, dated May 6, 2014, 1 page.
Submission documents re RCE in U.S. Appl. No. 13/205,328, dated Apr. 28, 2014, 1 page.
Submission in EP App. Ser. No. 04807580.8, dated Jun. 13, 2014, 18 pages.
Tahara et al., "Lenvatinib in Radioactive Iodine-refractory Differentiated Thyroid Cancer: Results of the Phase 3 trial (SELECT trial),"01-18-1, Abstract and Presentation Document, $12^{th}$ Annual Meeting of Japanese Society of Medical Oncology, Jul. 17, 2014, 21 pages.
Vergote et al., "Prognostic and prediction role of circulating angiopoietin-2 in multiple solid tumors: An analysis of approximately 500 patients treated with lenvatinib across tumor types," Am Soc Clin Oncol Annual Meeting Abstract, May 31, 2014, abstract 11061, 3 pages.

(56) References Cited

OTHER PUBLICATIONS

Wang et al., "KRAS, BRAF, PIK3CA mutations and Pten Expression in Human Colorectal Cancer-Relationship with Metastatic Colorectal Cancer," Ann Oncol., 2010, 21(Supp 6):V164.
Yamori et al., "Current Treatment of Solid Tumors New Approaches of Treatment, Drug Treatment, Kinase Inhibitors/Kokeigan no Saishin Chiryo Chiryo no Aratana Torikumi Yakubutsu Ryoho Kinase Inhibitors," JP J Clin Med., Jun. 1, 2010, 68(6):1059-1066.
Yang et al., "RG7204 (PLX4032), a Selective BRAF V600E Inhibitor, Displays Potent Antitumor Activity in Preclinical Melanoma Models," Cancer Res., 2010, 70(13):5518-5527.
Yokota, "ASCO report: Gastrointestinal Cancer field/ASCO Hokoku Shokakigan Ryoiki," Gan Bunshi Hyoteki Chiryo, 2010, 8(4):271-283.
"Clinical Trial: AMG 706 20040273 Thyroid Cancer Study: Stage 4 Cancer Treatments, Chat w/a Cancer Info Expert About Stage 4 Cancer Treatment Options," accessed from www.CancerCenter.com, 4 pages (2005).
"Arzneimittelwirkungen Lehrbuch der Pharmakologie und Toxikologie," Ernst Mutschler Ed Mutschler E et al., Arzneimittelwirkungen Lehrbuch der Pharmakologie und Toxikologie, Wissenschaftliche Verlagsgesellschaft, Stuttgart, Jan. 1, 1999, p. 1-p. 5, XP007919509 (English translation).
"Chapter 2.2 Loslichkeit, Losungsgeschwindigkeit, Loslichkeitsverbesserung," Rudolf Voigt Ed—Voigt R et al., Pharmazeutische Technologie fuer Studium und Beruf, DT. Apotheker-Verl, Stuttgart; DE, Jan. 1, 2000, p. 40-p. 52, XP008143620 (English translation).
Abuzar et al., "Synthesis of some new 7-chloro-4-substituted quinolines as potential antiparasitic agents," Eur. J. Med. Chem., 21(1):5-8 (1986).
Agarwal et al., "Binding of discoidin domain receptor 2 to collagen I: an atomic force microscopy investigation," Biochemistry, 41(37):11091-11098 (2002).
Amended Claims filed in EP App. Ser. No. 11798224.9, filed Aug. 2, 2013, 35 pages.
Amended Claims filed in KR App. Ser. No. 10-2010-7011023, filed Jul. 17, 2013, 15 pages (with English translation).
Amended Claims filed in RU App. Ser. No. 2013140169, dated Aug. 29, 2013, 17 pages (with English translation).
Amended description filed after receipt of search report for EP Patent App. No. 10809938.3, filed Dec. 8, 2011.
Amended Specification filed in AU App. Ser. No. 2012246490, filed Aug. 2, 2013, 15 pages.
Amendment after Allowance filed on Jan. 4, 2011 for CA App. Ser. No. 2426461.
Amendment and Response to Final Office Action under 37 C.F.R. §1.116 for U.S. Appl. No. 12/092,539, filed Jun. 15, 2011.
Amendment and Response to Final Office Action under 37 C.F.R. §1.116 for U.S. Appl. No. 12/864,817, filed Dec. 5, 2011.
Amendment and Response to Non-Final Office Action for U.S. Appl. No. 11/997,543, filed Aug. 19, 2011.
Amendment and Response to Office Action under 37 C.F.R § 1.111 for U.S. Appl. No. 12/439,339, dated Aug. 22, 2013, 14 pages.
Amendment and Response to Office Action under 37 C.F.R. § 1.111 dated Apr. 2, 2013 for U.S. Appl. No. 13/083,338, 9 pages.
Amendment and Response to Office Action under 37 C.F.R. §1.111 for U.S. Appl. No. 11/997,719, filed Dec. 23, 2010.
Amendment and Response to Office Action under 37 C.F.R. §1.111 for U.S. Appl. No. 12/092,539, filed Mar. 11, 2011.
Amendment and Response to Office Action under 37 C.F.R. §1.111 for U.S. Appl. No. 12/439,339, filed Feb. 7, 2012.
Amendment and Response to Office Action under 37 C.F.R. §1.111 for U.S. Appl. No. 12/524,754, filed Feb. 17, 2012.
Amendment and Response to Office Action under 37 C.F.R. §1.111 for U.S. Appl. No. 12/741,682, filed Jul. 30, 2012.
Amendment and Response to Office Action under 37 C.F.R. §1.111 for U.S. Appl. No. 12/864,817, filed Aug. 9, 2011.
Amendment and Response to Office Action under 37 C.F.R. §1.111 for U.S. Appl. No. 13/205,328, filed Apr. 11, 2012.
Amendment and Response to Office Action under 37 C.F.R. §1.116 for U.S. Appl. No. 11/997,543, filed Jan. 9, 2012.
Amendment and Response to Office Action under 37 C.F.R. §1.116 for U.S. Appl. No. 12/439,339, filed Jul. 30, 2012.
Amendment filed in EP App. Ser. No. 12774278.1, filed Aug. 13, 2013, 12 pages.
Amendment filed in JP App. Ser. No. 2008-532141, filed Jul. 5, 2013, 2 pages (with English translation).
Amendment filed on Apr. 11, 2006 for CN App. Ser. No. 01819710.8 (with English translation).
Amendment filed on Apr. 17, 2002 for TW App. Ser. No. 90125928 (with English translation).
Amendment filed on Apr. 19, 2005 for JP App. Ser. No. 2002-536056 (with English translation).
Amendment filed on Aug. 17, 2004 for ZA App. Ser. No. 2003/3567.
Amendment filed on Aug. 4, 2004 for ZA App. Ser. No. 2003/3567.
Amendment filed on Dec. 12, 2011 for JO Patent App. No. 55/2011 (with English translation).
Amendment filed on Dec. 15, 2011 for VN App. Ser. No. 1-2011-03484 (with English translation).
Amendment filed on Dec. 22, 2011 for ZA App. Ser. No. 2011/08697.
Amendment filed on Feb. 9, 2011 for TW App. Ser. No. 100104281.
Amendment filed on Jan. 11, 2010 for CN App. Ser. No. 200580026468.7 (with English translation).
Amendment filed on Jan. 26, 2010 for CN App. Ser. No. 200710007097.9 (with English translation).
Amendment filed on Jul. 2, 2009 for CN App. Ser. No. 200710007097.9 (with English translation).
Amendment filed on Jun. 22, 2010 for CN App. Ser. No. 200710007097.9 (with English translation).
Amendment filed on Mar. 6, 2006 for KR App. Ser. No. 10-2003-7005506 (with English translation).
Amendment filed on Mar. 7, 2005 for JP App. Ser. No. 2002-536056 (with English translation).
Amendment filed on Mar. 8, 2006 for KR App. Ser. No. 10-2005-7020292 (with English translation).
Amendment filed on May 10, 2012 for JP Patent Application No. 2011-527665.
Amendment filed on May 21, 2009 for JP App. Ser. No. 2005-124034 (with English translation).
Amendment filed on May 28, 2003 for CN App. Ser. No. 01819710.8 (with English translation).
Amendment filed on Nov. 19, 2009 for CN App. Ser. No. 200710007097.9 (with English translation).
Amendment filed on Oct. 25, 2005 for KR App. Ser. No. 10-2003-7005506 (with English translation).
Amendment filed on Oct. 28, 2011 for LB Patent App. No. 9292.
Amendment filed on Oct. 9, 2006 for CN App. Ser. No. 01819710.8 (with English translation).
Amendment filed on Sep. 13, 2005 for CN App. Ser. No. 01819710.8 (with English translation).
Amendment filed on Sep. 23, 2009 for CN App. Ser. No. 200580026468.7 (with English translation).
Amendment, Response to Office Action under 37 C.F.R. § 1.111 and Information Disclosure Statement for U.S. Appl. No. 13/624,278, filed Jun. 28, 2013, 23 pages.
Amendments received before examination for EP App. Ser. No. 01976786.2, dated Sep. 10, 2004.
American Association for Cancer Research, "Redefining The Frontiers of Science," 94th Annual Meeting, vol. 44, 2nd Edition, Washington Convention Center, Washington, DC (Jul. 11-14, 2003).
Anderson et al., "Preparation of Water-soluble Compounds through Salt Formation. The Practice of Medicinal Chemistry," *Technomics*, 347-349 and 355-356 (Sep. 25, 1999).
Anonymous, "Scientific Discussion," EMEA, URL: htttp://www.ema.europa.eu/docs/en_GB/document library/EPARScientific_Discussion/human/000406/WC500022203.pdf, 1-61 (2004) (XP007918143).
Applicant Observation for CN App. Ser. No. 200780017371.9, filed May 29, 2013, 6 pages (with English translation).
Approval of request for amendments for EP App. Ser. No. 04025700.8, dated Mar. 13, 2008.

(56) References Cited

OTHER PUBLICATIONS

Argument and Amendment for JP App. Ser. No. 2008-556208, filed Mar. 21, 2013, 15 pages (with English translation).
Argument and Amendment for JP App. Ser. No. 2008-532141, filed Nov. 29, 2012, 12 pages (with English translation).
Argument and Amendment for JP. App. Ser. No. 2008-516724, filed Nov. 28, 2012, 22 pages (with English translation).
Argument and Amendment for JP. App. Ser. No. 2009-123432, dated Jun. 12, 2012, 12 pages (with English translation).
Argument and Amendment for JP. App. Ser. No. 2009-529019, dated Jul. 3, 2012, 14 pages (with English translation).
Argument Brief filed on Mar. 6, 2006 for KR App. Ser. No. 10-2003-7005506 (with English translation).
Argument Brief filed on Mar. 8, 2006 for KR App. Ser. No. 10-2005-7020292 (with English translation).
Argument Brief filed on Nov. 24, 2011 for KR App. Ser. No. 10-2007-7001347 (with English translation).
Argument filed on Apr. 19, 2005 for JP App. Ser. No. 2002-536056 (with English translation).
Argument filed on Mar. 23, 2009 for JP App. Ser. No. 2005-124034 (with English translation).
Argument filed on May 21, 2009 for JP App. Ser. No. 2005-124034 (with English translation).
Asu no Shinyaku ("The New Drugs of Tomorrow"), editing/printing by Technomics, Inc., 81-83 (Dec. 2006) (English translation), 14 pages.
Australian Office Action for App. Ser. No. 2008205847, issued on Apr. 11, 2012.
Australian Office Action for App. Ser. No. 2008211952, issued on Apr. 3, 2012.
Baker et al., "Blockade of vascular endothelial growth factor receptor and epidermal growth factor receptor signaling for therapy of metastatic human pancreatic cancer," Cancer Res., 62:1996-2003 (2002).
Bastin et al., "Salt Selection and Optimisation Procedures for Pharmaceutical New Chemical Entities," Organic Process Research & Development, 4(5):427-435 (2000) (XP002228592).
Bellone et al., "Growth Stimulation of Colorectal Carcinoma Cells via the c-kit Receptor is Inhibited by TGF-β-1," Journal of Cellular Physiology, 172:1-11 (1997).
Benjamin et al., "Selective ablation of immature blood vessels in established human tumors follows vascular endothelial growth factor withdrawal," J. Clin. Invest., 103(2):159-165 (1999).
Berdel et al., "Recombinant Human Stem Cell Factor Stimulates Growth of a Human Glioblastoma Cell Line Expressing c-kit Protooncogene," Cancer Res., 52:3498-3502 (1992).
Berge et al., "Pharmaceutical Salts," Journal of Pharmaceutical Sciences, 66(1):1-19 (Jan. 1977) (XP002550655).
Bergers et al., "Benefits of targeting both pericytes and endothelial cells in the tumor vasculature with kinase inhibitors," J. Clin. Invest., 111(9):1287-1295 (2003).
Bernex et al., "Spatial and temporal patterns of c-kit-expressing cells in WlacZ/+ and WlacZ/WlacZ mouse embryos", Development 122:3023-3033 (1996).
Blume-Jensen et al., "Activation of the Human c-kit Product by Ligand-Induced Dimerization Mediates Circular Actin Reorganization and Chemotaxis," The EMBO Journal, 10(13):4121-4128 (1991).
Boissan et al., "c-Kit and c-kit mutations in mastocytosis and other hematological diseases," J. Leukocyte Biol., 67:135-148 (2000).
Brief communication to applicant for EP App. Ser. No. 01976786.2, dated Sep. 9, 2005.
Bruns et al., "Effect of the vascular endothelial growth factor receptor-2 antibody DC101 plus gemcitabine on growth, metastasis and angiogenesis of human pancreatic cancer growing orthotopically in nude mice," J. Cancer, 102:101-108 (2002).
Bussolino et al., "Role of Soluble Mediators in Angiogenesis," Eur. J. Cancer, 32A(14):2401-2412 (1996).

Cairns et al., "New antiallergic pyrano[3,2g]quinoline-2,8-dicarboxylic acids with potential for the topical treatment of asthma," J. Med. Chem., 28(12):1832-1842 (1985).
Canadian Office Action for App. Ser. No. 2426461, dated Dec. 6, 2007.
Canadian Office Action for App. Ser. No. 2426461, dated Feb. 10, 2010.
Canadian Office Action for App. Ser. No. 2426461, dated May 8, 2009.
Canadian Office Action for App. Ser. No. 2426461, dated Nov. 20, 2008.
CancerCare, "Types of Lung Cancer," Cancer Care, Inc. [online] [retrieved on Nov. 12, 2009]. Retrieved from the Internet: www.lungcancer.org/reading/types.php?printable=true (2009).
Cappellen et al., "Frequent activating mutations of FGFR3 in human bladder and cervix carcinomas," Nat. Genet., 23:18-20 (1999).
Carlomagno et al., "BAY 43/9006 inhibition of oncogenic RET mutants," J. Natl. Cancer Inst., 98(5):326-34 (2006).
Carlomagno et al., "ZD6474, an orally available inhibitor of KDR tyrosine kinase activity, efficiently blocks oncogenic RET kinases," Cancer Res., 62:7284-7290 (2002).
Chen et al., "FGFR3 as a therapeutic target of the small molecule inhibitor PKC412 in hematopoietic malignancies," Oncogene, 24:8259-8267 (2005).
Chesi et al., "Activated fibroblast growth factor receptor 3 is an oncogene that contributes to tumor progression in multiple myeloma," Blood, 97:729-736 (2001).
Chesi et al., "Frequent translocation t(4;14)(p16.3;q32.3) in multiple myeloma is associated with increased expression and activating mutations of fibroblast growth factor receptor 3," Nat. Genet., 16:260-264 (1997).
Chikahisa et al, "TSU-68 KDR/flk-1 inhibitor, can modulate the anti-tumor activity of paclitaxel by the induction of endothelial cell and tumor cell apoptosis," 61st Annual Meeting of the Japanese Cancer Association, 2002, 61(1374):443, 5 total pages (with English translation).
Chinese Office Action for App. Ser. No. 200710007097.9, issued on Mar. 6, 2009.
Chinese Office Action for App. Ser. No. 200780017371.9, issued on Mar. 7, 2012, with English translation.
Chinese Office Action for App. Ser. No. 200880002425.9, issued on Mar. 7, 2012, with English translation.
Chinese Office Action for App. Ser. No. 200880003336.6, issued on May 24, 2011, with English translation.
Chinese Office Action for App. Ser. No. 200880115011.7, issued on Feb. 20, 2012, with English translation.
Chinese Office Action for App. Ser. No. 201080030508.6, issued on Nov. 30, 2012.
Ciardiello et al., "ZD1839 (IRESSA), an EGFR-selective tyrosine kinase inhibitor, enhances taxane activity in bcl-2 overexpressing, multidrug-resistant MCF-7 ADR human breast cancer cells," Int. J. Cancer, 98:463-469 (2002).
Clark et al., "Safety and Pharmacokinetics of the Dual Action Raf Kinase and Vascular Endothelial Growth Factor Receptor Inhibitor, BAY43-9006, in Patients with Advanced Refractory Solid Tumors ," Clin. Cancer Res., 11:5472-5480 (2005).
ClinicalTrials.gov, "A Study of E7080 Alone, and in Combination With Everolimus in Subjects With Unresectable Advanced or Metastatic Renal Cell Carcinoma Following One Prior Vascular Endothelial Growth Factor (VEGF)-Targeted Treatment," National Institutes of Health, Food and Drug Administration, National Library of Medicine, [online] [retrieved on Sep. 27, 2010]. Retrieved from the Internet: http://clinicaltrials.gov/ct2/show/NCT01136733, (May 26, 2010).
Cohen et al., "Expression of Stem Cell Factor and c-kit in Human Neuroblastoma," Blood, 84(10):3465-3472 (1994).
Communication about intention to grant a European patent for EP App. Ser. No. 01976786.2, dated Sep. 4, 2006.
Communication about intention to grant a European patent for EP App. Ser. No. 04025700.8, dated Oct. 15, 2007.
Communication about intention to grant a European patent for EP App. Ser. No. 06023078.6, dated Jul. 18, 2008.

(56) References Cited

OTHER PUBLICATIONS

Communication from the Examining Division for EP App. Ser. No. 01976786.2, dated Aug. 17, 2005.
Communication from the Examining Division for EP App. Ser. No. 01976786.2, dated Mar. 21, 2006.
Communication from the Examining Division for EP App. Ser. No. 01976786.2, dated Sep. 19, 2005.
Communication from the Examining Division for EP App. Ser. No. 04025700.8, dated Apr. 10, 2006.
Communication from the Examining Division for EP App. Ser. No. 04025700.8, dated Oct. 23, 2006.
Communication from the Examining Division for EP App. Ser. No. 05783232.1, dated Feb. 7, 2008.
Communication from the Examining Division for EP App. Ser. No. 06023078.6, dated Aug. 2, 2007.
Communication from the Examining Division for EP App. Ser. No. 06023078.6, dated Sep. 26, 2007.
Communication regarding the expiry of opposition period for EP App. Ser. No. 01976786.2, dated Jan. 4, 2008.
Communication regarding the expiry of opposition period for EP App. Ser. No. 04025700.8, dated May 7, 2009.
Communication regarding the expiry of opposition period for EP App. Ser. No. 05783232.1, dated Feb. 19, 2010.
Communication regarding the expiry of opposition period for EP App. Ser. No. 06023078.6, dated Nov. 4, 2009.
Communication under Rule 71(3) EPC dated Nov. 20, 2011, for Application No. 05783232.1.
Continuation Patent Application, Preliminary Amendment and Information Disclosure Statement for U.S. Appl. No. 13/923,858, filed Jun. 21, 2013, 97 pages.
Croom et al., "Imatinib mesylate," *Drugs*, 63(5):513-522 (2003).
Da Silva et al., "A novel germ-line point mutation in RET exon 8 (Gly(533)Cys) in a large kindred with familial medullary thyroid carcinoma," *J. Clin. Endocrinol. Metab.*, 88:5438-5443 (2003).
De Lange et al., "Phase II trial of cisplatin and gemcitabine in patients with advanced gastric cancer," Annals of Oncology, 15:484-488 (2004).
Decision of Final Rejection issued in CN App. Ser. No. 200780017371.9, dated Jul. 3, 2013, 16 pages (with English translation).
Decision to grant a European patent for EP App. Ser. No. 01976786.2, dated Feb. 1, 2007.
Decision to grant a European patent for EP App. Ser. No. 04025700.8, dated Jun. 5, 2008.
Decision to grant a European patent for EP App. Ser. No. 05783232.1, dated Mar. 19, 2009.
Decision to grant a European patent for EP App. Ser. No. 06023078.6, dated Dec. 4, 2008.
Deficiencies in sequence listing for EP App. Ser. No. 06023078.6, dated Dec. 5, 2006.
Demand for Appeal Trial filed in JP App. Ser. No. 2008-532141, filed Jul. 5, 2013, 10 pages (with English translation).
Deplanque et al., "Anti-Angiogenic Agents: Clinical Trial Design and Therapies in Development," *European Journal of Cancer*, 36:1713-1724 (2000).
Dermer, "Another Anniversary for the War on Cancer," *Bio/Technology*, 12:320 (1994).
Di Raimondo et al., "Antiogenic Factors in multiple myeloma: higher levels in bone than in peripheral blood," *Haematologica*, 85:800-805 (2000).
DiLorenzo et al., "Targeted Therapy in the Treatment of Metastatic Renal Cell Cancer," Oncology, 77(suppl 1):122-131 (2009).
Elisei et al., "Identification of a novel point mutation in the RET gene (Ala883Thr), which is associated with medullary thyroid carcinoma phenotype only in homozygous condition," J. Clin. Endocrinol. Metab., 89:5823-5827 (2004).
Erber et al., "Combined inhibition of VEGF and PDGF signaling enforces tumor vessel regression by interfering with pericyte-mediated endothelial cell survival mechanisms," *FASEB J.*, 18(2):338-340 (2004).

European Office Action for App. Ser. No. 04719054.1, issued on Oct. 30, 2009.
European Office Action for App. Ser. No. 04807580.8, issued on Apr. 18, 2011.
European Office Action for App. Ser. No. 04807580.8, issued on Oct. 25, 2011.
European Office Action for App. Ser. No. 04818213.3, issued on Feb. 2, 2012.
European Office Action for App. Ser. No. 07743994.1, issued on Oct. 10, 2012.
European Search Report directed at application No. 06768437.3, issued on Oct. 11, 2010.
European Search Report directed at application No. 06782407.8, issued on Jul. 23, 2010.
European Search Report directed at application No. 06832529.9, issued on Jul. 29, 2009.
European Search Report directed at application No. 06833681.7, issued on Nov. 24, 2010.
European Search Report directed at application No. 07743994.1, issued on May 4, 2010.
European Search Report directed at application No. 07806561.2, issued on Jan. 19, 2011.
European Search Report directed at application No. 10015141.4, issued on Sep. 9, 2011.
European Search Report for App. Ser. No. 03791389.4, issued on Jul. 7, 2011.
European Search Report for App. Ser. No. 04025700.8, dated Jan. 13, 2005.
European Search Report for App. Ser. No. 04719054.1, issued on Apr. 17, 2009.
European Search Report for App. Ser. No. 04818213.3, issued on Jul. 30, 2007.
European Search Report for App. Ser. No. 05783232.1, issued on Sep. 7, 2007.
European Search Report for App. Ser. No. 06023078.6, issued on Mar. 16, 2007.
European Search Report for App. Ser. No. 06767145.3, issued on May 23, 2011.
European Search Report for App. Ser. No. 10809938.3, issued on Jan. 2, 2013.
Examination Report dated Feb. 18, 2005 for NZ App. Ser. No. 525324.
Examination Report dated Feb. 21, 2008 for AU App. Ser. No. 2006203099.
Examination Report dated Jan. 30, 2013 for AU App. Ser. No. 2009210098, 10 pages.
Examination Report dated Mar. 26, 2008 for AU App. Ser. No. 20062:i6039.
Examination Report dated May 4, 2006 for AU App. Ser. No. 2001295986.
Examination Report dated Nov. 24, 2012 for AU App. Ser. No. 2008325608.
Examination Report dated Oct. 13, 2003 for NZ App. Ser. No. 525324.
Examination Report dated Sep. 2, 2004 for NZ App. Ser. No. 525324.
Examination Report dated Sep. 20, 2005 for AU App. Ser. No. 2001295986.
Explanation of Circumstances Concerning Accelerated Examination filed May 10, 2012 for JP Patent Application No. 2011-527665, 21 pages (with English Translation).
Folkman et al., "Angiogenesis," *The Journal of Biological Chemistry*, 267(16):10931-10934 (1992).
Folkman et al., "Seminars in Medicine of the Beth Israel Hospital, Boston: Clinical Applications of Research on Angiogenesis," *The New England Journal of Medicine*, 333(26):1757-1763 (1995).
Folkman et al., "What is the Evidence That Tumors are Angiogenesis Dependent?," *Journal of the National Cancer Institute*, 82(1):4-6 (1990).
Forbes et al., "Dissolution kinetics and solubilities ofp-aminosalicylic acid and its salts," *International Journal of Pharmaceutics*, 126:199-208 (1995).

(56) References Cited

OTHER PUBLICATIONS

Formality Requirement dated Jun. 18, 2003 for PH App. Ser. No. 1-2003-500266.
Freshney, R. Ian, "Culture of Animal Cells, A Manual of Basic Technique," *Alan R. Liss, New York*, 29-32 (1983).
Frings, "New Molecular Targeted Therapeutic Drugs Clinical Results of Bevacizumab in Non-Small Cell Lung Cancer (NSCLC)", *Jap. J. Lung Cancer*, Jun. 2006, 46(3):277-281 (with English Translation).
Funahashi et al., "P-2123, Lenvatinib treatment of differentiated thyroid cancer (DTC): Analysis to identify biomarkers associated with response," The 71$^{st}$ Annual Meeting of the Japanese Cancer Association, Sep. 19-21, 2012, p. 339.
Furitsu et al., "Identification of Mutations in the Coding Sequence of the Proto-Oncogene c-kit in a Human Mast Cell Leukemia Cell Line Causing Ligand-Independent Activation of c-kit Product," *J. Clin. Invest.*, 92:1736-1744 (1993).
Furitsu et al., "Stable medicinal compositions of quinolinecarboxamide derivative," Database Caplus Chemical Abstracts Service, Columbus, OH, US (2006) (XP002520305).
Furuta et al., "Synthesis and Biological Evaluation of Selective Inhibitors of PDGF Receptor Auto Phosphorylation," #64, *American Chemical Society, 226$^{th}$ ACS National Meeting*, New York, NY (Sep. 7-11, 2003).
Gall-Istok et al., "Notes on the Synthesis of 4-Amino-6,7-Di-Sec-Butoxyquinoline, -6,7-Methylene-Dioxyquinoline and its N-Alkylaminoacetyl Derivatives," *Acta Chimica Hungarica*, 112(2):241-247 (1983).
Gardner et al., "In Vitro Activity Sorghum-Selective Fluorophenyl Urea Herbicides," *Pesticide Biochemistry and Physiology*, 24(3):285-297 (1985).
Gatzemeier et al., "Phase III comparative study of high-dose cisplatin versus a combination of paclitaxel and cisplatin in patients with advanced non-small-cell lung cancer," *J. Clin. Oncol.*, 18(19):3390-3399 (2000).
Giles, "The vascular endothelial growth factor (VEGF) signaling pathway: a therapeutic target in patients with hematologic malignancies," Oncologist, 6(suppl 5):32-39 (2001).
Golkar et al., "Mastocytosis," *Lancet*, 349:1379-1385 (1997).
Gould, "Salt Selection for Basic Drugs," *International Journal of Pharmaceutics*, 33:201-217, (1986) (XP025813036).
Gura, "Cancer Models Systems for Identifying new drugs are often faulty," Science, 278:1041-1042 (1997).
Haleblian,"Characterization of habits and crystalline modification of solids and their pharmaceutical applications," *J. Pharm. Sci.*, 64(8):1269-1288 (1975).
Haller, "Chemotherapy for advanced pancreatic cancer," *Int. J. Radiation Oncol. Biol. Phys.*, 56:16- 23 (2003).
Hamel et al., "The Road Less Travelled: c-kit and Stem Cell Factor," Journal of Neuro-Oncology, 35:327-333 (1997).
Hattori et al., "Immunohistochemical detection of K-sam protein in stomach cancer," *Clin. Cancer Res.*, 2(8):1373-1381 (1996).
Hayamo et al., "Pericytes in experimental MDA-MB231 tumor angiogenesis," *Histochemistry and Cell Biology*, 117(6):527-534, Abstract (Jun. 2002).
Hayek et al., "An In Vivo Model for Study of the Angiogenic Effects of Basic Fibroblast Growth Factor," *Biochemical and Biophysical Research Communications*, 147(2):876-880 (1987).
Hearing Notice issued May 4, 2012, in India Patent Application No. 383/CHENP/2008.
Heinrich et al , "Inhibition of c-kit receptor tyrosine kinase activity by STI 571, a selective tyrosine kinase inhibitor," Blood, 96(3):925-932 (2000) (XP001097629).
Hennequin et al., "Novel 4-Anilinoquinazolines with C-7 Basic Side Chains: Design and Structure Activity Relationship of a Series of Potent, Orally Active, VEGF Receptor Tyrosine Kinase Inhibitors," J. Med. Chem., 45:1300-1312 (2002).
Hibi et al., "Coexpression of the Stem Cell Factor and the c-kit Genes in Small-Cell Lung Cancer," Oncogene, 6:2291-2296 (1991).
Hines et al., "Coexpression of the c-kit and Stem Cell Factor Genes in Breast Carcinomas," *Cell Growth & Differentiation*, 6:769-779 (1995).
Hogaboam et al., "Novel Role of Transmembrane SCF for Mast Cell Activation and Eotaxin Production in Mast Cell-Fibroblast Interactions," *J. Immunol.*, 160:6166-6171 (1998).
Hurwitz et al., "Bevacizumab plus irinotecan, fluorouracil, and leucovorin for metastatic colorectal cancer," N. Engl. J. Med., 350(23):2335-2342 (2004).
Ikeda et al., "Changes in Phenotype and Proliferative Potential of Human Acute Myeloblastic Leukemia Cells in Culture with Stem Cell Factor," *Experimental Hematology*, 21:1686-1694 (1993).
Ikeda et al., "Expression and Functional Role of the Proto-Oncogene c-kit in Acute Myeloblastic Leukemia Cells," *Blood*, 78(11):2962-2968 (1991).
Inai et al., "Inhibition of vascular endothelial growth factor (VEGF) signaling in cancer causes loss of endothelial fenestrations, regression of tumor vessels, and appearance of basement membrane ghosts," *American Journal of Pathology*, 165:35-52 (2004).
Indian Office Action for App. Ser. No. 1571/CHENP/2007, issued on Oct. 30, 2012.
Indian Patent Application No. 2572/CHENP/2006 filed Jul. 13, 2006.
Information about decision on request for EP App. Ser. No. 06023078.6, dated Mar. 21, 2007.
Inoue et al., "Molecular Target Therapy Targeting Angiogenesis Pathways," *The Nishinihon Journal of Urology*, 66:425-432 (2004).
International Preliminary Report on Patentability and Written Opition of the International Searching Authroity for App. Ser. No. PCT/JP2006/312487, issued on Dec. 24, 2007.
International Preliminary Report on Patentability for App. Ser. No. PCT/JP01/09221, dated Jan. 8, 2003.
International Preliminary Report on Patentability for App. Ser. No. PCT/JP2004/003087, issued on Feb. 13, 2006.
International Preliminary Report on Patentability for App. Ser. No. PCT/JP2010/063804, issued on Mar. 13, 2012.
International Preliminary Report on Patentability for App. Ser. No. PCT/JP2011/064430, dated Jan. 24, 2013, 6 pages.
International Search Report for App. Ser. No. PCT/JP01/09221, issued on Jan. 15, 2002.
International Search Report for App. Ser. No. PCT/JP2004/003087, issued on Jul. 13, 2004.
International Search Report for App. Ser. No. PCT/JP2006/315698, issued on Oct. 17, 2006.
International Search Report for App. Ser. No. PCT/JP2006/322514, issued on Jan. 23, 2007.
International Search Report for App. Ser. No. PCT/JP2006/323881, issued on Jan. 23, 2007.
International Search Report for App. Ser. No. PCT/JP2007/060560, issued on Sep. 11, 2007.
International Search Report for App. Ser. No. PCT/JP2007/063525, issued on Sep. 4, 2007.
International Search Report for App. Ser. No. PCT/JP2007/067088, issued on Nov. 20, 2007.
International Search Report for App. Ser. No. PCT/JP2008/051024, issued on Apr. 1, 2008.
International Search Report for App. Ser. No. PCT/JP2008/051697, issued on Mar. 4, 2008.
International Search Report for App. Ser. No. PCT/JP2008/070321, issued on Jun. 20, 2009.
International Search Report for App. Ser. No. PCT/JP2009/051244, issued on Mar. 24, 2009.
International Search Report for App. Ser. No. PCT/JP2010/063804, issued on Sep. 14, 2010.
Invitation to declare maintenance of the application for EP App. Ser. No. 01976786.2, dated Jul. 12, 2004.
Invitation to declare maintenance of the application for EP App. Ser. No. 05783232.1, dated Sep. 25, 2007.
Invitation to declare maintenance of the application for EP App. Ser. No. 06023078.6, dated May 2, 2007.
Israeli Office Action for App. Ser. No. 155447, issued on Oct. 16, 2007 (with English translation).

(56) References Cited

OTHER PUBLICATIONS

Israeli Office Action for App. Ser. No. 189677, issued on Feb. 18, 2009 (with English translation).
Israeli Office Action for App. Ser. No. 195282, issued on Feb. 5, 2012 (with English translation).
Israeli Office Action for App. Ser. No. 199907, issued on Apr. 22, 2012 (with English translation).
Itoh et al., "Preferential alternative splicing in cancer generates a K-sam messenger RNA with higher transforming activity," *Cancer Res.*, 54:3237-3241 (1994).
Jakeman et al., "Developmental Expression of Binding Sites and Messenger Ribonucleic Acid for Vascular Endothelial Growth Factor Suggests a Role for This Protein in Vasculogenesis and Angiogenesis," *Endocrinology*, 133(2):848-859 (1993).
Japanese Allowance for App. Ser. No. P2005-515330, issued on Apr. 21, 2009.
Japanese Allowance for App. Ser. No. P2005-516605, issued on Dec. 7, 2010.
Japanese Office Action dated Apr. 11, 2005 for App. Ser. No. 2002-536056 (with English translation).
Japanese Office Action for App. Ser. No. P2005-516605, issued on Jun. 1, 2010.
Japanese Office Action for App. Ser. No. P2008-516724, issued on Oct. 9, 2012 (with English translation).
Jhiang, "The RET proto-oncogene inn human cancers," *Oncogene*, 19:5590-5597 (2000).
Jiang, "ZD6474: an Agent That Selectively Targets Both VEGFR Tyrosine Kinase and EGFR Tyrosine Kinase", Jap. J. Lung Cancer, Jun. 2006, 46(3):283-288 (with English translation).
Jimenez et al., "Pheochromocytoma and medullary thyroid carcinoma: a new genotype-phenotype correlation of the RET protooncogene 891 germline mutation," *J. Clin. Endocrinol. Metab.*, 89:4142-4145 (2004).
Johnson et al., "Paclitaxel plus carboplatin in advanced non-small-cell lung cancer: a phase II trial," *J. Clin. Oncol.*, 14(7):2054-2060 (1996).
Jung et al., "Effects of combination anti-vascular endothelial growth factor receptor and anti-epidermal growth factor receptor therapies on the growth of gastric cancer in a nude mouse model," *Eur. J. Cancer*, 38:1133-1140 (2002).
Juurikivi et al., "Inhibition of c-kit tyrosine kinase by imatinib mesylate induces apoptosis in mast cells in rheumatoid synovia: a potential approach to the treatment of arthritis," *Ann Rheum. Dis.*, 64:1126-1131 (2005).
Kanai et al., "Current status and future perspective of molecular targeted therapy for hepatocellular carcinoma," *Journal of the Japanese Society of Gastroenterology*, 106:1727-1735 (2009) (English translation).
Kanakura et al., "Expression, Function and Activation of the Proto-Oncogene c-kit Product in Human Leukemia Cells," *Leukemia and Lymphorma*, 10:35-41 (1993).
Kashuk et al., "Phenotype-genotype correlation in Hirschsprung disease is illuminated by comparative analysis of the RET protein sequence," *PNAS*, 102(25):8949-8954 (2005).
Kawano et al., "Presentation Abstract, Abstract Number; 1619, Combination of VEGFR inhibitor lenvatinib (E7080) and Met/EphB4inhibitor golvatinib (E7050) overcomes VEGFR inhibitor—resistant tumor vascular", Annual Meeting 2013, Walter E. Washington Convention Center, Washington, D.C., Apr. 6-10, 2013, 1 page.
Kay et al., "Eosinophils and Eosinophil-Associated Cytokines in Allergic Inflammation," *Int. Arch. Allergy Immunol.*, 113:196-199 (1997).
Kelly et al., "Randomized phase III trial of paclitaxel plus carboplatin versus vinorelbine plus cisplatin in the treatment of patients with advanced non—small-cell lung cancer: a Southwest Oncology Group trial," *J. Clin. Oncol.*, 19(13):3210-3218 (2001).

Kim et al., "A phase II study of irinotecan plus cisplatin for patients with advanced stage IIIB or IV NSCLC previously treated with nonplatinum-based chemotherapy," *Cancer*, 107(4):799-805 (2006).
Kim et al., "An orally administered multitarget tyrosine kinase inhibitor, SU11248, is a novel potent inhibitor of thyroid oncogenic RET/papillary thyroid cancer kinases," *J. Clin. Endocrinol. Metlab.*, 91(10):4070-4076 (2006).
Kitamura et al., "Regulation of Development, Survival and Neoplastic Growth of Mast Cells through the c-kit Receptor," *Int. Arch Allergy Immunol.*, 107:54-56 (1995).
Kitteringham et al., "A Simple Method for the Synthesis of Unsymmetrical Ureas," *Synthetic Communications*, 30(11):1937-1943 (2000).
Kleespies et al., "Tyrosine kinase inhibitors and gemcitabine: New treatment options in pancreatic cancer,?" *Drug Resistance Updates*, 9:1-18 (2006).
Ko, "Stomach Cancer," Cancer Supportive Care.com [published online Feb. 2003], [retrieved on Dec. 28, 2011]. Retrieved from the Internet: http://web.archive.org/web/20030224212825/http://www.cancersupportivecare.com/stomach.html.
Kolibaba et al., "Protein Tyrosine Kinases and Cancer," *Biochimica et Biophysica Acta*, 1333:F217- F248 (1997).
Korean Office Action for App. Ser. No. 10-2003-7005506, issued on Jan. 5, 2006 (with English translation).
Korean Office Action for App. Ser. No. 10-2005-7020292, issued on Dec. 8, 2005 (with English translation).
Korean Office Action for App. Ser. No. 10-2006-7013993, issued on Jul. 31, 2007 (with English translation).
Korean Office Action for App. Ser. No. 10-2007-7001347, issued on Apr. 27, 2012 (with English translation).
Kotva et al., "Substances with Antineoplastic Activity, LIII. N-(ξ-(4-Pyrrolo[2,3-d]Pyrimidinylthio) Valery]} Amino Acids and Analogous Derivatives of Di-and Triglycine," Collection Czechoslov. Chem. Commun., 38:1438-1444 (1973).
Koyama et al, "Anti-tumor effect of E7080, a novel angiogenesis inhibitor," Folia Pharmacol. Japan., 2008, 132: 100-104 (with English translation).
Lasota et al., "Mutations in Exons 9 and 13 of KIT Gene Are Rare Events in Gastrointestinal Stromal Tumors," American Journal of Pathology, 157(4):1091-1095 (2000).
Lennartsson et al., The Stem Cell Factor Receptor/c-Kit as a Drug Target in Cancer, *Current Cancer Drug Target*, 6:561-571 (2006).
Lesueur et al., "Polymorphisms in RET and its coreceptors and ligands as genetic modifiers of multiple endocrine neoplasia type 2A," *Cancer Res.*, 66:1177-1180 (2006).
Lev et al., "A Specific Combination of Substrates is Involved in Signal Transduction by the Kit-Encoded Receptor," *The EMBO Journal*, 10(3):647-654 (1991).
Li et al., "Abrogation of c-kit/Steel factor-dependent tumorigenesis by kinase defective mutants of the c-kit receptor: c-kit kinase defective mutants as candidate tools for cancer gene therapy," *Cancer Res.*, 56:4343-4346 (1996) (XP002522473).
Lin et al., "The vascular endothelial growth factor receptor tyrosine kinase inhibitor PTK787/ZK222584 inhibits growth and migration of multiple myeloma cells in the bone marrow microenvironment," *Cancer Res.*, 62(17):5019-5026 (2002).
Longley et al., "Altered Metabolism of Mast-Cell Growth Factor (c-kit Ligand) in Cutaneous Mastocytosis," *The New England Journal of Medicine*, 328(18):1302-1307 (1993).
Longley et al., "Classes of c-KIT activating mutations: proposed mechanisms of action and implications for disease classification and therapy," *Leuk. Res.*, 25:571-576 (2001).
Longley et al., "Somatic c-KIT Activating Mutation in Urticaria Pigmentosa and Aggressive Mastocytosis: Establishment of Clonality in a Human Mast Cell Neoplasm," *Nature Genetics*, 12:312-314 (1996).
Lukacs et al., "Stem Cell Factor (c-kit Ligand) Influences Eosinophil Recruitment and Histamine Levels in Allergic Airway Inflammation," *J. Immunol.*, 156:3945-3951 (1996).
Maintenance of the application for EP App. Ser. No. 01976786.2, dated Sep. 6, 2004.

(56) References Cited

OTHER PUBLICATIONS

Maintenance of the application for EP App. Ser. No. 05783232.1, dated Nov. 9, 2007.
Matsui et al., "E7080 (ER-203492-00), a Novel VEGF Receptor ) Tyrosine Kinase Inhibitor-I. Characterization as an Angiogenesis Inhibitor," Abstract # 51, *AACR*, Washington, USA (Jul. 11-14, 2003).
Matsui et al., "E7080, a novel inhibitor that targets multiple kinases, has potent antitumor activities against stem cell factor producing human small cell lung cancer H146, based on angionenesis inhibition," *Int. J Cancer*, 122:664-671 (2008).
Matsui et al., "E7080, a novel multi-receptor Tyrosine Kinase Inhibitor, inhibited in vitro / in vivo VEGF- and SCF-driven angiogenesis SCLC cell line," Abstract #146, *EORTC-NCI-AACR*, Geneva, Switzerland (Sep. 28-Oct. 1, 2004).
Matsui et al., "E7080, a novel multi-targeted tyrosine kinase inhibitor, exhibits anti-angiogenic activity via inhibition of KIT signaling in a small cell lung cancer xenograft model," *Eur. J. Cancer*, 2(8):47 (2004).
Matsui et al., "Quantitative analysis of the profile of tumor vessels may be useful as predictive biomarkers for E7080," Abstract #4631, *98th AACR annual meeting*, Los Angeles, CA, (Apr. 14-18, 2007).
Matsui et al., "VEGFRs inhibitor E7080 inhibits lymph node metastasis of human breast carcinoma, by preventing murine lymphatic endothelial cells from lymphangiogenesis," Abstract #PD12-8, *18th EORTC-NCI-AACR Symposium on "Molecular Targets and Cancer Therapeutics,"* Prague, Czech Republic (Nov. 7-10, 2006).
Matsui, "Extracellular matrix of linitis plastica as a possible new therapeutic target," Surgical Treatment, Sep. 2003, 89(3):301-306 (with English translation).
McCarty et al., "ZD6474, a vascular endothelial growth factor receptor tyrosine kinase inhibitor with additional activity against epidermal growth factor receptor tyrosine kinase, inhibits orthotopic growth and angiogenesis of gastric cancer," *Mol. Cancer Ther.*, 3(9):1041-1048 (2004).
McCulloch et al., "Astragalus-based Chinese herbs and platinum-based chemotherapy for advanced non-small-cell lung cancer: meta-analysis of randomized trials," *J. Clin. Oncol.*, 24(3):419-430 (2006).
Meltzer, "The Pharmacological Basis for the Treatment of Perennial Allergic Rhinitis and Non-Allergic Rhinitis with Topical Corticosteroids," *Allergy*, 52:33-40 (1997).
Mendel et al., "In vivo antitumor activity of SU11248, a novel tyrosine kinase inhibitor targeting vascular endothelial growth factor and platelet-derived growth factor receptors: determination of a pharmacokinetic/pharmacodynamic relationship," *Clin. Cancer Res.*, 9:327-337 (2003).
Metcalfe et al., "Lineage Commitment in the Progeny of Murine Hematopoietic Preprogenitor Cells: Influence of Thrombopoietin and Interleukin 5," *Proc. Nat'l Acad. Sci. USA*, 95:6408-6412 (1998).
Metcalfe et al., "Mast cells," *Physiol. Rev.*, 77(4):1033-1079 (1997).
Metcalfe, "Classification and Diagnosis of Mastocytosis: Current Status," *J. Invest. Dermatol.*, 96:2S-4S (1991).
Micke et al., "Characterization of c-kit expression in small cell lung cancer: prognostic and therapeutic implications," *Clin. Cancer Res.*, 9:188-194 (2003).
Miller et al., "Paclitaxel plus bevacizumab versus paclitaxel alone for metastatic breast cancer," *N. Engl. J. Med.*, 357(26):2666-2676 (2007).
Miyazaki et al., "Synthesis, Structure and Biological Activity Relationship of E7080 and its Derivatives as Novel and Potent Antiangiogenic Protein Tyrosine Kinase Inhibitors Including the VEGF Receptors, FGFR1 Receptor and PDGF Receptor," AIMECS03, Kyoto, Japan (Oct. 14-17, 2003).
Mologni et al., "Inhibition of RET tyrosine kinase by SU5416," *J. Mol. Endocrinol.*, 37(2):199-212 (2006).
Morgan et al., "Dynamic contrast-enhanced magnetic resonance imaging as a biomarker for the pharmacological response of PTK787/Zk 222584, an inhibitor of the vascular endothelial growth factor receptor tyrosine kinases, in patients with advanced colorectal cancer and liver metastases: results from two phase I studies," *J. Clin. Oncol.*, 21(21):3955-3964 (2003).
Morikawa et al., "Angiogenesis and Pericytes, " *The Cell*, 37(4):164-168 (2005) (English translation).
Morris et al., "An Integrated Approach to the Selection of optimal Salt Form for a New Drug Candidate," *International Journal of Pharmaceutics*, 105:209-217 (1994) (XP023724810).
Myers et al., "The Preparation and SAR of 4-(Anilino), 4-(Phenoxy), and 4-(Thiophenoxy)-Quinazolines: Inhibitors of p561ck and EGF-R Tyrosine Kinase Activity," *Bioorgan. & Med. Chem. Letters*, 7:417-420 (1997).
Naclerio et al., "Rhinitis and Inhalant Allergens," *JAMA*, 278(22):1842-1848 (1997).
Nagata et al., "Elevated Expression of the Proto-Oncogene c-kit in Patients with Mastocytosis," *Leukemia*, 12:175-181 (1998).
Nakamura et al., "E7080 (ER-203492-00), a Novel VEGF Receptor Tyrosine Kinase Inhibitor-II. Effects on Growth of Human Tumor Xenografts and Life Span of Mice in Colon 38 Orthotopic Transplantation Model," Abstract #52, *AACR*, Toronto, Canada (Apr. 5-9, 2003).
Naruse et al., "Antitumor activity of the selective epidermal growth factor receptor-tyrosine kinase inhibitor (EGFR-TKI) Iressa (ZD1839) in an EGFR-expressing multidrug-resistant cell line in vitro and in vivo," *Int. J. Cancer*, 98:310-315 (2002).
Naski et al., "Graded activation of fibroblast growth factor receptor 3 by mutations causing achondroplasia and thanatophoric dysplasia," *Nat. Genet.*, 13:233-237 (1996).
Natali et al., "Breast Cancer is Associated with Loss of the c-kit Oncogene Product," *Int. J. Cancer*, 52:713-717 (1992).
NCBI GenBank Accession No. NM_000222, Coffey et al. (Feb. 11, 2008).
Nishio et al, "Phase 1 study of lenvatinib combined with carboplatin and paclitaxel in patients with non-small-cell lung cancer", British Journal of Cancer, 2013, 109:538-544.
Nocka et al., "Expression of c-kit gene products in known cellular targets of W mutations in normal and W mutant mice—evidence for an impaired c-kit kinase in mutant mice," *Cold Spring Harbor Laboratory Press*, 3:816-826 (1989) (XP002522472).
Noriyuki et al., "Anti-tumor effect of E7080, a novel angiogenesis inhibitor," Database BIOSIS [Online] Biosciences Information Service, Philadelphia, PA, US: Database accession No. PREV200800475929, Aug. 2008, XP002677323.
Notice of Acceptance dated Aug. 10, 2004 for ZA Patent App. No. 2003/3567.
Notice of Acceptance dated Aug. 3, 2006 for AU App. Ser. No. 2001295986.
Notice of Acceptance dated May 13, 2008 for AU App. Ser. No. 2006236039.
Notice of Acceptance for AU App. Ser. No. 2009210098, dated Jun. 4, 2013, 3 pages.
Notice of Acceptance of Complete Specification dated Mar. 4, 2005 for NZ App. Ser. No. 525324.
Notice of Allowability dated Nov. 28, 2007 for PH App. Ser. No. 1-2003-500266.
Notice of Allowance dated Apr. 19, 2005 for RU App. Ser. No. 2003114740 (with English translation).
Notice of Allowance dated Apr. 24, 2012 for U.S. Appl. No. 12/524,754.
Notice of Allowance dated Apr. 29, 2010 for AU App. Ser. No. 2005283422.
Notice of Allowance dated Aug. 7, 2012 for Japanese App. Ser. No. P2007-529565 (with English translation).
Notice of Allowance dated Dec. 15, 2006 for CN App. Ser. No. 01819710.8.
Notice of Allowance dated Dec. 26, 2007 for IL App. Ser. No. 155447 (with English translation).
Notice of Allowance dated Feb. 15, 2013 for NZ App. Ser. No. 598291, 1 page.
Notice of Allowance dated Feb. 27, 2009 for U.S. Appl. No. 11/293,785.
Notice of Allowance dated Feb. 5, 2010 for CN App. Ser. No. 200580026468.7 (with English translation).

(56) References Cited

OTHER PUBLICATIONS

Notice of Allowance dated Jul. 17, 2012 for JP App. Ser. No. P2011-527665 (with English translation).
Notice of Allowance dated Jul. 21, 2009 for JP App. Ser. No. 2005-124034 (with English translation).
Notice of Allowance dated Jun. 13, 2006 for U.S. Appl. No. 10/420,466.
Notice of Allowance dated Jun. 20, 2012 for EP App. Ser. No. 06782407.8.
Notice of Allowance dated Jun. 25, 2012 for EP App. Ser. No. 07806561.2.
Notice of Allowance dated Jun. 3, 2008 for U.S. Appl. No. 11/293,785.
Notice of Allowance dated Mar. 16, 2007 for U.S. Appl. No. 10/420,466.
Notice of Allowance dated Mar. 22, 2012 for U.S. Appl. No. 12/986,638.
Notice of Allowance dated Mar. 8, 2013 for CA App. Ser. No. 2627598, 1 page.
Notice of Allowance dated May 18, 2009 for U.S. Appl. No. 11/293,785.
Notice of Allowance dated May 6, 2013 for EP App. Ser. No. 04818213.3, 22 pages.
Notice of Allowance dated Nov. 14, 2011 for IL App. Ser. No. 181697 (with English translation).
Notice of Allowance dated Nov. 19, 2008 for U.S. Appl. No. 11/293,785.
Notice of Allowance dated Nov. 2, 2012 for EP App. Ser. No. 06782407.8.
Notice of Allowance dated Nov. 2, 2012 for EP App. Ser. No. 07806561.2.
Notice of Allowance dated Oct. 14, 2010 for CA App. Ser. No. 2426461.
Notice of Allowance dated Oct. 17, 2011 for CA App. Ser. No. 2579810.
Notice of Allowance dated Oct. 18, 2006 for MX App. Ser. No. PA/a/2003/003362 (with English translation).
Notice of Allowance dated Oct. 20, 2008 for TW App. Ser. No. 90125928 (with English translation).
Notice of Allowance dated Oct. 31, 2008 for NO App. Ser. No. 20031731 (with English translation).
Notice of Allowance dated Oct. 9, 2010 for CN App. Ser. No. 200710007097.9 (with English translation).
Notice of Allowance dated Sep. 12, 2005 for U.S. Appl. No. 10/420,466.
Notice of Allowance dated Sep. 20, 2011 for JP App. Ser. No. 2006-535174.
Notice of Allowance dated Sep. 25, 2012 for U.S. Appl. No. 12/986,638.
Notice of Allowance dated Sep. 4, 2012 in JP App. Ser. No. P2009-123432 (with English translation).
Notice of Allowance for CN App. Ser. No. 200980103218.7, dated May 27, 2013, 4 pages (with English translation).
Notice of Allowance for JP App. Ser. No. 2008-516724, dated Jan. 22, 2013, 4 pages, with English translation.
Notice of Allowance for U.S. Appl. No. 12/524,754, dated Jan. 18, 2013, 9 pages.
Notice of Allowance for U.S. Appl. No. 12/741,682, dated Feb. 19, 2013, 65 pages.
Notice of Allowance for U.S. Appl. No. 12/741,682, dated Jun. 19, 2013, 10 pages.
Notice of Allowance for U.S. Appl. No. 12/524,754 dated Oct. 9, 2012.
Notice of Allowance for U.S. Appl. No. 13/083,338, dated Jun. 4, 2013, 57 pages.
Notice of Allowance for U.S. Appl. No. 13/205,328, dated Jun. 10, 2013, 58 pages.
Notice of Allowance issued in CN App. Ser. No. 201080030508.6, dated Jul. 4, 2013, 4 pages (with English translation).
Notice of Allowance issued in EP App. Ser. No. 10015141.4, dated Jul. 1, 2013, 40 pages.
Notice of Allowance issued in IL App. Ser. No. 175363, dated Aug. 13, 2013, 2 pages (with English translation).
Notice of Allowance issued in JP App. Ser. No. P2008-556208, dated Jul. 9, 2013, 4 pages (with English translation).
Notice of Allowance issued in U.S. Appl. No. 12/524,754, dated Jul. 19, 2013, 11 pages.
Notice of decision for patent dated Apr. 17, 2006 for KR App. Ser. No. 10-2005-7020292, (with English translation).
Notice of decision for patent dated Jun. 12, 2006 for KR App. Ser. No. 10-2003-7005506 (with English translation).
Notice of Reasons for Rejection issued in JP App. Ser. No. P2009-540099, dated Jul. 2, 2013, 7 pages (with English translation).
Notice Prior to Examination dated Jun. 29, 2008 for IL App. Ser. No. 189677 (with English translation).
Notice Prior to Examination dated Mar. 9, 2009 for IL App. Ser. No. 181697 (with English translation).
Notification dated Apr. 25, 2008 for Ph App. Ser. No. 1-2003-500266.
Notification of Defects for IL App. Ser. No. 195282, dated Apr. 10, 2013, 4 pages (with English Translation).
Notification of Non-Compliant Amendment filed on Jan. 13, 2005 for U.S. Appl. No. 10/420,466.
Nugiel et al., "Synthesis and evaluation of indenopyrazoles as cyclin-dependent kinase inhibitors. 2. Probing the indeno ring substituent pattern," *J. Med. Chem.*, 45(24):5224-5232 (2002).
Ocqueteau et al., Expression of the CD117 antigen (C-Kit) on normal and myelomatous plasma cells, Br. J. Haematol., 95:489-493 (1996).
Office Action dated Apr. 11, 2013 for IL App. Ser. No. 217197, 4 pages (with English translation).
Office Action dated Apr. 16, 2013 for CA App. Ser. No. 2652442, 2 pages.
Office Action dated Apr. 27, 2010 for CN App. Ser. No. 200710007097.9 (with English translation).
Office Action dated Apr. 28, 2009 for JP App. Ser. No. 2005-124034 (with English translation).
Office Action dated Apr. 8, 2013 for U.S. Appl. No. 11/997,719, 55 pages.
Office Action dated Apr. 9, 2013 for CN App. Ser. No. 201080030508.6, 6 pages (with English translation).
Office Action dated Aug. 11, 2006 for CN App. Ser. No. 01819710.8 (with English translation).
Office Action dated Aug. 3, 2012 for CN App. Ser. No. 200680020317.5 (with English translation).
Office Action dated Aug. 8, 2003 for PH App. Ser. No. 1-2003-500266.
Office Action dated Dec. 20, 2010 for IL App. Ser. No. 181697 (with English translation).
Office Action dated Dec. 25, 2009 for CN App. Ser. No. 200710007097.9 (with English translation).
Office Action dated Feb. 10, 2006 for CN App. Ser. No. 01819710.8 (with English translation).
Office Action dated Jan. 27, 2009 for JP App. Ser. No. 2005-124034 (with English translation).
Office Action dated Jul. 15, 2011 for CA App. Ser. No. 2579810.
Office Action dated Jul. 21, 2006 for PH App. Ser. No. 1-2003-500266.
Office Action dated Jul. 24, 2009 for CN App. Ser. No. 200710007096.4 (with English translation).
Office Action dated Jul. 27, 2005 for KR App. Ser. No. 10-2003-7005506 (with English translation).
Office Action dated Jun. 26, 2009 for CN App. Ser. No. 200580026468.7 (with English translation).
Office Action dated Jun. 27, 2007 for PH App. Ser. No. 1-2003-500266.
Office Action dated Jun. 5, 2012 for JP App. Ser. No. 2009-123432 (with English translation).
Office Action dated Jun. 7, 2006 for MX App. Ser. No. PA/a/2003/003362 (with English translation).
Office Action dated Mar. 14, 2013 for CN App. Ser. No. 200780017371.9, 9 pages (with English translation).

(56) References Cited

OTHER PUBLICATIONS

Office Action dated Mar. 21, 2007 for PH App. Ser. No. 1-2003-500266.
Office Action dated Mar. 29, 2013 for U.S. Appl. No. 13/624,278, 73 pages.
Office Action dated Mar. 6, 2009 for Cn App. Ser. No. 200710007097.9 (with English translation).
Office Action dated Mar. 7, 2007 for NO App. Ser. No. 20031731 (with English translation).
Office Action dated May 13, 2005 for CN App. Ser. No. 01819710.8 (with English translation).
Office Action dated May 16, 2008 for NO App. Ser. No. 20031731 (with English translation).
Office Action dated Nov. 13, 2012 for JP App. Ser. No. P2008-532141 (with English translation).
Office Action dated Nov. 20, 2009 for CN App. Ser. No. 200580026468.7 (with English translation).
Office Action dated Nov. 26, 2007 for MX App. Ser. No. PA/a/2005/013764 (with English translation).
Office Action dated Oct. 15, 2012 for IL App. Ser. No. 200090 (with English translation).
Office Action dated Oct. 4, 2005 for MX App. Ser. No. PA/a/2003/003362 (with English translation).
Office Action dated Oct. 4, 2007 for NO App. Ser. No. 20031731 (with English translation).
Office Action dated Sep. 11, 2009 for CN App. Ser. No. 200710007097.9 (with English translation).
Office Action dated Sep. 19, 2012 for CA App. Ser. No. 2627598.
Office Action dated Sep. 28, 2011 for KR App. Ser. No. 10-2007-7001347 (with English translation).
Office Action dated Sep. 28, 2012 for CN App. Ser. No. 200780017371.9 (with English translation).
Office Action dated Sep. 29, 2012 for CN App. Ser. No. 200980103218.7 (with English translation).
Office Action dated Sep. 5, 2008 for NO App. Ser. No. 20031731 (with English translation).
Office Action dated Sep. 5, 2012 for CN App. Ser. No. 200880003336.6 (with English translation).
Office Action dated Sep. 5, 2012 for CN App. Ser. No. 200880115011.7 (with English translation).
Office Action dated Sep. 7, 2007 for PH App. Ser. No. 1-2003-500266.
Office Action for EP App. Ser. No. 08846814.5, dated Apr. 16, 2013, 5 pages.
Office Action for IL App. Ser. No. 175363, dated Jan. 2, 2013, 2 pages, with English translation.
Office Action for IL App. Ser. No. 200090, dated Jul. 24, 2013, 5 pages (with English translation).
Office Action for IL App. Ser. No. 205512, dated Dec. 20, 2012, 8 pages, with English translation.
Office Action for IL App. Ser. No. 207089, dated Jan. 6, 2013, 5 pages (with English translation).
Office Action for JP App. Ser. No. 2008-556208, dated Jan. 22, 2013, 8 pages, with English translation.
Office Action for JP App. Ser. No. P2008-532141, dated May 21, 2013, 4 pages (with English translation).
Office Action for JP App. Ser. No. P2009-551518, dated Jun. 18, 2013, 5 pages (with English translation).
Office Action for KR App. Ser. No. 10-2008-7013685, dated May 20, 2013, 10 pages (with English translation).
Office Action for U.S. Appl. No. 12/039,381, dated Sep. 12, 2013, 15 pages.
Office Action for U.S. Appl. No. 13/083,338, dated Jan. 3, 2013, 9 pages.
Office Action for U.S. Appl. No. 13/238,085, dated Sep. 6, 2013, 10 pages.
Office Action for U.S. Appl. No. 12/439,339, dated May 23, 2013, 15 pages.
Office Action issued in MX App. Ser. No. MX/a/2012/002011, dated Jul. 17, 2013, 6 pages (with English translation).
Office Action issued Jan. 7, 2011, in U.S. Appl. No. 12/092,539.
Office Communication dated Sep. 13, 2004 for U.S. Appl. No. 10/420,466.
Office Letter Confirmation of Amendment After Allowance dated Jan. 11, 2011 for CA App. Ser. No. 2426461.
Office Letter re Notice of Allowance dated May 25, 2012 for ZA App. Ser. No. 201108697.
Official Letter and Notice of Allowance for AU App. Ser. No. 2008211952, dated Jul. 10, 2012.
Official Letter and Notice of Allowance for AU App. Ser. No. 2008325608, dated Feb. 27, 2013, 7 pages.
Official Letter re Grant of Request for Correction of Specification for SG App. Ser. No. 201108602-2, dated Aug. 8, 2012.
Ohe et al., "Randomized phase III study of cisplatin plus irinotecan versus carboplatin plus paclitaxel, cisplatin plus gemcitabine, and cisplatin plus vinorelbine for advanced non-small-cell lung cancer: Four-Arm Cooperative Study in Japan," *Ann Oncol.*, 18(2):317-323 (2007).
Okayama et al., "Activation of Eosinophils with Cytokines Produced by Lung Mast Cells," *Int Arch Allergy Immunol.*, 114(suppl 1):75-77 (1997).
Okayama et al., "Human Lung Mast Cells are Enriched in the Capacity to Produce Granulocyte-Macrophage Colony-Stimulating Factor in Response to IgE-Dependent Stimulation," *Eur. J. Immunol.*, 28:708-715 (1998).
Okura et al., "Effects of monoclonal anti-c-kit antibody (ACK2) on melanocytes in newborn mice," *J. Invest. Dermatol.*, 105(3):322-328 (1995).
Olaso et al., "DDR2 receptor promotes MMP-2-mediated proliferation and invasion by hepatic stellate cells," *J. Clin. Invest.*, 108(9):1369-1378 (2001).
Ozols et al., "Phase III trial of carboplatin and paclitaxel compared with cisplatin and paclitaxel in patients with optimally resected stage III ovarian cancer: a Gynecologic Oncology Group study," *J. Clin. Oncol.*, 21(17):3194-3200 (2003).
Pakistani Office Action for App. Ser. No. 94/2011, issued on May 9, 2012.
Partial European Search Report for App. Ser. No. 01976786.2, dated Apr. 6, 2004.
Paterson et al., "Preclinical studies of fibroblast growth factor receptor 3 as a therapeutic target in multiple myeloma," *British Journal of Haematology*, 124:595-603 (2004).
Paz et al., "Development of angiogenesis inhibitors to vascular endothelial growth factor receptor 2. Current status and future perspective," *Frontiers in Bioscience*, 10:1415-1439 (May 1, 2005).
Plowright et al., "Ectopic expression of fibroblast growth factor receptor 3 promotes myeloma cell proliferation and prevents apoptosis," Blood, 95:992-998 (2000).
Polverino et al, "AMG 706, an Oral, Multikinase Inhibitor that Selectively Targets Vascular Endothelial Growth Factor, Platelet—Derived Growth Factor, and Kit Receptors, Potently inhibits Angiogenesis and Induces Regression in Tumor Xenografts," Cancer Research, 66(17):8715-8721 (2006).
Preliminary Amendment and Response to Restriction Requirement in U.S. Appl. No. 12/439,339, filed Aug. 10, 2011.
Preliminary Amendment and Response to Restriction Requirement in U.S. Appl. No. 13/083,338, filed Apr. 30, 2012.
Preliminary Amendment dated Apr. 26, 2013 for U.S. Appl. No. 13/870,507, 10 pages.
Preliminary Amendment filed on Apr. 18, 2003 for U.S. Appl. No. 10/420,466.
Preliminary Amendment filed on Dec. 2, 2005 for U.S. Appl. No. 10/420,466.
Preliminary Amendment filed on Feb. 3, 2006 for U.S. Appl. No. 11/293,785.
Preliminary Amendment filed on May 23, 2003 for KR App. Ser. No. 10-2003-7005506 (with English translation).
Preliminary Amendment filed on Oct. 27, 2003 for U.S. Appl. No. 10/420,517.
Pritzker, "Cancer Biomarkers: Easier Said Than Done," *Clinical Chemistry*, 48(8):1147-1150 (2002).
Reasons for Reexamination dated Sep. 11, 2012 for CN App. Ser. No. 200680020317.5 (with English translation).

(56) References Cited

OTHER PUBLICATIONS

Reexamination filed on May 25, 2004 for TW App. Ser. No. 90125928 (with English translation).
Reexamination filed on Nov. 25, 2004 for TW App. Ser. No. 90125928 (with English translation).
Registered dated Feb. 24, 2009 for PH App. Ser. No. 1-2003-500266.
Rejection dated Apr. 26, 2004 for TW App. Ser. No. 90125928 (with English translation).
Reply to communication from the Examining Division for EP App. Ser. 06023078.6, dated Feb. 4, 2008.
Reply to communication from the Examining Division for EP App. Ser. 06023078.6, dated Sep. 11, 2007.
Reply to communication from the Examining Division for EP App. Ser. No. 01976786.2, dated Jan. 25, 2006.
Reply to communication from the Examining Division for EP App. Ser. No. 01976786.2, dated Jul. 19, 2006.
Reply to communication from the Examining Division for EP App. Ser. No. 04025700.8, dated Feb. 15, 2007.
Reply to communication from the Examining Division for EP App. Ser. No. 04025700.8, dated Jan. 26, 2007.
Reply to communication from the Examining Division for EP App. Ser. No. 04025700.8, dated Sep. 12, 2006.
Reply to Examination Report dated Feb. 8, 2013 for EP App. Ser. No. 07743994.1, 4 pages.
Reply to official communication for EP App. Ser. No. 05783232.1, dated Apr. 30, 2008.
Reply to the invitation to remedy deficiencies for EP App. Ser. No. 06023078.6, dated Jan. 11, 2007.
Request for amendment of the text intended for grant and translation of claims for EP App. Ser. No. 04025700.8, dated Feb. 1, 2008.
Request for amendment of the text intended for grant and translation of claims for EP App. Ser. No. 06023078.6, dated Nov. 5, 2008.
Request for Continued Examination (Rce) transmittal for U.S. Appl. No. 12/864,817, filed Dec. 22, 2011.
Request for correction of errors in filed documents for EP App. Ser. No. 06023078.6, dated Feb. 13, 2007.
Request for Substantive Examination for ID App. Ser. No. W-00201201031, filed Jun. 3, 2013, 6 pages (with English translation).
Request for Substantive Examination for UA App. Ser. No. a201203132, filed Apr. 15, 2013, 16 pages (with English translation).
Request for Voluntary Amendments filed May 10, 2012, in Ukraine Patent Application No. A 2012 03132, with English Abstract.
Request to Amend Complete Specification dated Feb. 15, 2013 for AU App. Ser. No. 2008325608, 23 pages.
Request to Amend Complete Specification dated May 9, 2013 for AU App. Ser. No. 2009210098, 22 pages.
Response and Amended Claims filed in EP App. Ser. No. 08846814.5, filed Aug. 1, 2013, 14 pages.
Response and Amended Claims filed in EP App. Ser. No. 10809938.3, filed Jul. 19, 2013, 7 pages.
Response filed in IL App. Ser. No. 195282, filed Jul. 11, 2013, 13 pages (with English translation).
Response filed on Apr. 11, 2006 for CN App. Ser. No. 01819710.8 (with English translation).
Response filed on Apr. 17, 2007 for PH App. Ser. No. 1-2003-500266.
Response filed on Apr. 27, 2006 for AU App. Ser. No. 2001295986.
Response filed on Aug. 13, 2009 for CA App. Ser. No. 2426461.
Response filed on Aug. 14, 2006 for PH App. Ser. No. 1-2003-500266.
Response filed on Aug. 18, 2008 for NO App. Ser. No. 20031731 (with English translation).
Response filed on Aug. 21, 2006 for MX App. Ser. No. PA/a/2003/003362 (with English translation).
Response filed on Aug. 26, 2004 for NZ App. Ser. No. 525324.
Response filed on Aug. 5, 2003 for PH App. Ser. No. 1-2003-500266.
Response filed on Dec. 11, 2007 for TW App. Ser. No. 90125928 (with English translation).
Response filed on Dec. 15, 2005 for MX App. Ser. No. PA/a/2003/003362 (with English translation).
Response filed on Dec. 4, 2007 for IL App. Ser. No. 155447 (with English translation).
Response filed on Feb. 23, 2009 for CA App. Ser. No. 2426461.
Response filed on Feb. 26, 2008 for U.S. Appl. No. 11/293,785.
Response filed on Jan. 11, 2010 for CN App. Ser. No. 200580026468.7 (with English translation).
Response filed on Jan. 21, 2005 for NZ App. Ser. No. 525324.
Response filed on Jan. 26, 2010 for CN App. Ser. No. 200710007097.9 (with English translation).
Response filed on Jul. 1, 2005 for U.S. Appl. No. 10/420,466.
Response filed on Jul. 2, 2009 for CN App. Ser. No. 200710007097.9 (with English translation).
Response filed on Jul. 26, 2006 for AU App. Ser. No. 2001295986.
Response filed on Jul. 31, 2007 for PH App. Ser. No. 1-2003-500266.
Response filed on Jun. 22, 2010 for CN App. Ser. No. 200710007097.9 (with English translation).
Response filed on Mar. 17, 2005 for RU App. Ser. No. 2003114740 (with English translation).
Response filed on May 13, 2009 for IL App. Ser. No. 189677 (with English translation).
Response filed on May 16, 2008 for CA App. Ser. No. 2426461.
Response filed on May 20, 2010 for CA App. Ser. No. 2426461.
Response filed on May 7, 2008 for NO App. Ser. No. 20031731 (with English translation).
Response filed on May 8, 2008 for AU App. Ser. No. 2006236039.
Response filed on Nov. 19, 2009 for CN App. Ser. No. 200710007097.9 (with English translation).
Response filed on Nov. 30, 2004 for RU App. Ser. No. 2003114740 (with English translation).
Response filed on Oct. 13, 2008 for NO App. Ser. No. 20031731 (with English translation).
Response filed on Oct. 15, 2007 for PH App. Ser. No. 1-2003-500266.
Response filed on Oct. 8, 2004 for U.S. Appl. No. 10/420,466.
Response filed on Oct. 9, 2006 for CN App. Ser. No. 01819710.8 (with English translation).
Response filed on Sep. 10, 2007 for NO App. Ser. No. 20031731 (with English translation).
Response filed on Sep. 13, 2005 for CN App. Ser. No. 01819710.8 (with English translation).
Response filed on Sep. 15, 2003 for PH App. Ser. No. 1-2003-500266.
Response filed on Sep. 21, 2011 for CA App. Ser. No. 2579810.
Response filed on Sep. 8, 2003 for PH App. Ser. No. 1-2003-500266.
Response to Notice of Allowability filed on Dec. 13, 2007 for PH App. Ser. No. 1-2003- 500266.
Response to Notice Prior to Examination filed in IL App. Ser. No. 217197, filed Jul. 31, 2013, 9 pages (with English translation).
Response to Notice Prior to Examination filed on Apr. 22, 2009 for IL App. Ser. No. 181697 (with English translation).
Response to Notice Prior to Examination filed on Jan. 11, 2009 for IL App. Ser. No. 189677 (with English translation).
Response to Office Action dated Feb. 7, 2013 for CN App. Ser. No. 201080030508.6, 17 pages (with English translation).
Response to Office Action dated Jul. 5, 2012 for CN App. Ser. No. 200880115011.7 (with English translation).
Response to Office Action dated Nov. 30, 2012 for CN App. Ser. No. 200780017371.9, 4 pages (with English translation).
Response to Office Action filed on Jan. 25,2013 for CA App. Ser. No. 2627598, 9 pages.
Response to Office Action filed on Jul. 11, 2012 for CN App. Ser. No. 200880003336.6 (with English translation).
Response to Office Action filed on May 29, 2012 for RU App. Ser. No. 2012103471 (with English translation).
Response to Office Action for Australian App. Ser. No. 2006309551, filed on Mar. 28, 2012.

(56) References Cited

OTHER PUBLICATIONS

Response to Office Action for Israeli App. Ser. No. 205512, filed on Mar. 11, 2012 (with English translation).
Response to Office Action for Israeli App. Ser. No. 207089, filed on Mar. 11, 2012, with English translation.
Response to Office Action for MX App. Ser. No. MX/a/2012/002011, dated Aug. 29, 2013, 12 pages (with English translation).
Response to Office Action for U.S. Appl. No. 13/322,961, dated Jan. 25, 2013, 22 pages.
Response to Office Action for U.S. Appl. No. 10/420,466 dated Jun. 29, 2005.
Response to Office Action under 37 C.F.R. §1.111 for U.S. Appl. No. 12/523,495, filed Dec. 7, 2011.
Response to Office Action under 37 C.F.R. §1.111 for U.S. Appl. No. 13/083,338, filed Sep. 6, 2012.
Response to Office Action under 37 C.F.R.S 1.111 and Information Disclosure Statement for U.S. Appl. No. 11/997,719, filed Jul.3, 2013, 26 pages.
Response to Restriction Requirement for U.S. Appl. No. 11/997,543, filed Mar. 22, 2011.
Response to Restriction Requirement for U.S. Appl. No. 12/301,353, filed Nov. 23, 2010.
Response to Restriction Requirement for U.S. Appl. No. 12/524,754, filed Dec. 1, 2011.
Restriction Requirement for U.S. Appl. No. 11/997,543, dated Feb. 23, 2011.
Restriction Requirement for U.S. Appl. No. 12/092,539, dated Oct. 29, 2010.
Restriction Requirement for U.S. Appl. No. 12/301,353, dated Oct. 29, 2010.
Restriction Requirement for U.S. Appl. No. 12/439,339, dated Jul. 29, 2011.
Restriction Requirement for U.S. Appl. No. 12/524,754, dated Nov. 3, 2011.
Russian Office Action dated Apr. 11, 2012 for App. Ser. No. 2012103471, (with English translation).
Russian Office Action dated Jan. 19, 2005 for App. Ser. No. 2003114740 (with English translation).
Russian Office Action dated Jun. 29, 2004 for App. Ser. No. 2003114740 (with English translation).
Salmon et al., "Anti-angiogenic treatment of gastrointestinal malignancies," *Cancer Invest.*, 23(8):712-726 (2005).
Sandler et al., "Phase III trial of gemcitabine plus cisplatin versus cisplatin alone in patients with locally advanced or metastatic non-small-cell lung cancer," *J. Clin. Oncol.*, 18(1):122-130 (2000).
Santoro et al., "Drug insight: Small-molecule inhibitors of protein kinases in the treatment of thyroid cancer," *Nat. Clin. Pract. Endocrinol. Metab.*, 2(1):42-52 (2006).
Santoro et al., "Minireview: RET: normal and abnormal functions," *Endocrinology*, 145:5448-5451 (2004).
Santoro et al., "Molecular Mechanisms of RET Activation in Human Cancer," *Ann. N.Y. Academy of Sciences*, 963:116-121 (2002).
Scheijen et al., "Tryosine Kinase Oncogenes in Normal Hematopoiesis and Hematological Disease," *Oncogene*, 21:3314-3333 (2002).
Schlumberger et al., "A Phase 2 Trial of the Multi-Targeted Kinase Inhibitor Lenvatinib (E7080) in Advanced Medullary Thyroid Cancer (MTC)," 2012 ASCO Annual Meeting, Poster Presentation, Jun. 1-5, 2012.
Second Preliminary Amendment and Response to Restriction Requirement for U.S. Appl. No. 12/092,539, filed Nov. 22, 2010.
Sekido et al., "Preferential Expression of c-kit Protooncogene Transcripts in Small Cell Lung Cancer," *Cancer Res.*, 51:2416-2418 (1991).
Shiang et al., "Mutations in the transmembrane domain of FGFR3 cause the most common genetic form of dwarfism, achondroplasia," *Cell.*, 78:335-342 (1994).
Shimizu et al., "Orally active anti-proliferation agents: novel diphenylamine derivatives as FGF-R2 autophosphorylation inhibitors," *Bioorganic and Medicinal Chemistry Letters*, 14(4):875-879 (2004).
Siegel et al., "Sorafenib: Where Do We Go from Here?," *Hepatology*, 52:360-369 (2010).
Sihto et al., "KIT and platelet-derived growth factor receptor alpha tyrosine kinase gene mutations and KIT amplifications in human solid tumors," Journal of Clinical Oncology, 23(1):49-57 (2005).
Spacey et al., "Indolocarbazoles, Potent and Selective Inhibitors of Platelet-Derived Growth Factor Receptor Autophosphorylation," *Biochemical Pharmacology*, 55:261-271 (1998).
Strohmeyer et al., "Expression of the hst-1 and c-kit Protoonocogenes in Human Testicular Germ Cell Tumors," *Cancer Res.*, 51:1811-1816 (1991).
Submission Document(s) Before the Patent Office for IL App. Ser. No. 200090, dated Dec. 23, 2012, 16 pages, with English translation.
Submission Document Before the Patent Office dated Apr. 22, 2013 for IL App. Ser. No. 207089, 7 pages (with English translation).
Submission Document Before the Patent Office dated Mar. 14, 2013 for IL App. Ser. No. 205512, 12 pages (with English translation).
Submission Document Before the Patent Office for CL App. Ser. No. 2012-00412, dated Aug. 31, 2012, 6 pages (with English translation).
Submission Document Before the Patent Office for EP App. Ser. No. 03791389.4, dated Dec. 20, 2012, 4 pages.
Submission Document Before the Patent Office for EP App. Ser. No. 08846814.5, dated Jan. 3, 2013, 102 pages.
Submission Document Before the Patent Office for EP App. Ser. No. 8704376.6, dated Jan. 2, 2013, 22 pages.
Submission Document Before the Patent Office re Observation dated Feb. 16, 2013 for CN App. Ser. No. 200980103218.7, 8 pages (with English translation).
Submission Documents Before the Patent Office for CN App. Ser. No. 201080030508.6, dated May 27, 2013, 7 pages (with English translation).
Submission Documents Before the Patent Office for KR App. Ser. No. 10-2009-7017694, dated Jan. 18, 2013, 22 pages, with English translation.
Submission Documents Before the Patent Office for U.S. Appl. No. 12/741,682, dated May 17, 2013, 16 pages.
Submission Documents re New Claim Set Before the Patent Office for AR App. Ser. No. P110100513, dated Aug. 27, 2013, 8 pages (with English translation).
Submission Documents re Preliminary Amendment Before the Patent Office U.S. Appl. No. 14/002,018, dated Aug. 28, 2013, 9 pages.
Submission Documents re Rce Before the Patent Office for U.S. Appl. No. 13/083,338, dated Aug. 28, 2013, 20 pages.
Submission Documents re Rce Before the Patent Office for U.S. Appl. No. 12/524,754, dated Apr. 15, 2013, 17 pages.
Submission of Amendments and Complete Specification dated Apr. 10, 2013 for in App. Ser. No. 1571/CHENP/2007, 15 pages.
Submission of Document Before the Patent Office re Request for Voluntary Amendments dated Jan. 30, 2013 for NZ App. Ser. No. 598291, 8 pages.
Submission of Document re Claims filed in Response to Second Office Action for CN App. Ser. No. 200880115011.7, filed on Nov. 20, 2012.
Submission of Document re Request for Examination in CO App. Ser. No. 12-022608, submitted on Jun. 12, 2012.
Submission of Documents before the Patent Office for CN App. Ser. No. 200980103218.7, dated Mar. 13, 2013, 6 pages (with English translation).
Submission of Documents before the Patent Office for CN App. Ser. No. 200880115011.7, dated Apr. 11, 2013, 10 pages (with English translation).
Submission of Documents Before the Patent Office for IL App. Ser. No. 175363, dated Feb. 27, 2013, 23 pages.
Submission of Documents re Amendment in UA App. Ser. No. a2012 03132, submitted on May 22, 2012.

(56) References Cited

OTHER PUBLICATIONS

Submission of Documents re Claim 3 and Figure 3 for KR App. Ser. No. 10-2009-7005657, filed on Jul. 13, 2012.
Submission of Reference Materials in KR App. Ser. No. 10-2008-7013685, filed Jul. 5, 2013, 43 pages, (with English translation).
Supplementary European Search Report for App. Ser. No. 01976786.2, dated Jul. 6, 2004.
Supplementary European Search Report for App. Ser. No. 08 70 4376, dated Jun. 14, 2012.
Supplementary European Search Report issued Jul. 5, 2012, in European Patent Application No. 08846814.5.
Takahashi et al., "A case of inoperable scirrhous gastric cancer that responded remarkably to a combination of Ts-1+paclitaxel and showed complete loss of ascites," *Japanese Journal of Cancer and Chemotherapy*, 31(7):1093-1095 (2004).
Takeda et al., "AZD2171 shows potent anti-tumor activity against gastric cancer expressing variant K-Sam/FGFR2," Abstract #3785, *Proceeding of the American Association for Cancer Research*, 47:890 (2006).
Tan et al., "Randomized study of vinorelbine—gemcitabine versus vinorelbine—carboplatin in patients with advanced non-small cell lung cancer," *Lung Cancer*, 49(2):233-240 (2005).
Taniguchi et al., "Effect of c-kit Mutation on Prognosis of Gastrointestinal Stromal Tumors," *Cancer Res.*, 59:4297-4300 (1999).
Third Office Action dated Feb. 25, 2013 for CN App. Ser. No. 200880115011.7, 6 pages (with English translation).
Thomas et al., "The Eosinophil and its Role in Asthma," *Gen. Pharmac.*, 27(4)593-597 (1996).
Tian et al., "Activating c-kit Gene Mutations in Human Germ Cell Tumors," *American Journal of Pathology*, 154(6):1643-1647 (1999).
Tohyama et al., "P-3111, Preclinical effect of lenvatinib on human thyroid cancer targeting angiogenesis and receptor tyrosine kinase signaling," the 71$^{st}$ Annual Meeting of the Japanese Cancer Association, Sep. 19-21, 2012, p. 502.
Tonary et al., "Lack of expression of c-KIT in ovarian cancers is associated with poor prognosis," *Int. J. Cancer*, 89:242-250 (2000).
Tong et al., "Vascular normalization by vascular endothelial growth factor receptor 2 blockade induces a pressure gradient across the vasculature and improves drug penetration in tumors," *Cancer Res.*, 64:3731-3736 (2004).
Transmittal of Information Disclosure Statement, Terminal Disclaimer, Request for Continued Examination, and Response to Office Action under 37 C.F.R. §1.116 for U.S. Appl. No. 11/997,719, filed Jul. 6, 2011.
Traxler et al., "AEE788; A dual family epidermal growth factor receptor/ErbB2 and vascular endothelial growth factor receptor tyrosine kinase inhibitor with antitumor and antiangiogenic activity," *Cancer Res.*, 64:4931-4941 (2004).
Trudel et al., "CHIR-258, a novel, multitargeted tyrosine kinase inhibitor for the potential treatment of t(4;14) multiple myeloma," *Blood*, 105:2941-2948 (2005).
Trudel et al., "Inhibition of fibroblast growth factor receptor 3 induces differentiation and apoptosis in t(4;14) myeloma," *Blood*, 103:3521-3528 (2004).
Turner et al., "Fibroblast growth factor signaling: from development to cancer," *Nature Reviews, Cancer*, 10:116-129 (2010).
U.S. Notice of Allowance for U.S. Appl. No. 12/244,227, dated Oct. 22, 2010.
U.S. Office Action for U.S. Appl. No. 10/420,466, issued on Apr. 13, 2005.
U.S. Office Action for U.S. Appl. No. 10/577,531, issued on Sep. 23, 2008.
U.S. Office Action for U.S. Appl. No. 10/797,903, issued on Aug. 20, 2009.
U.S. Office Action for U.S. Appl. No. 10/797,903, issued on Dec. 11, 2007.
U.S. Office Action for U.S. Appl. No. 10/797,903, issued on Sep. 1, 2010.
U.S. Office Action for U.S. Appl. No. 11/293,785, issued on Sep. 4, 2007.
U.S. Office Action for U.S. Appl. No. 11/347,749, issued on Feb. 9, 2009.
U.S. Office Action for U.S. Appl. No. 11/997,543, issued on Feb. 23, 2011.
U.S. Office Action for U.S. Appl. No. 11/997,543, issued on May 19, 2011.
U.S. Office Action for U.S. Appl. No. 11/997,543, issued on Nov. 9, 2011.
U.S. Office Action for U.S. Appl. No. 11/997,719, issued on Apr. 6, 2011.
U.S. Office Action for U.S. Appl. No. 11/997,719, issued on Sep. 3, 2010.
U.S. Office Action for U.S. Appl. No. 12/092,539, issued on Jun. 28, 2011.
U.S. Office Action for U.S. Appl. No. 12/092,539, issued on May 9, 2011.
U.S. Office Action for U.S. Appl. No. 12/094,492, issued on Mar. 24, 2011.
U.S. Office Action for U.S. Appl. No. 12/400,562, issued on Mar. 31, 2010.
U.S. Office Action for U.S. Appl. No. 12/439,339, issued on Mar. 30, 2012.
U.S. Office Action for U.S. Appl. No. 12/439,339, issued on Nov. 14, 2011.
U.S. Office Action for U.S. Appl. No. 12/523,495, issued on Dec. 27, 2011.
U.S. Office Action for U.S. Appl. No. 12/523,495, issued on Sep. 27, 2011.
U.S. Office Action for U.S. Appl. No. 12/524,754, issued on Dec. 19, 2011.
U.S. Office Action for U.S. Appl. No. 12/741,682, issued on Apr. 30, 2012.
U.S. Office Action for U.S. Appl. No. 12/864,817, issued on Dec. 16, 2011.
U.S. Office Action for U.S. Appl. No. 12/864,817, issued on May 19, 2011.
U.S. Office Action for U.S. Appl. No. 12/864,817, issued on Nov. 3, 2011.
U.S. Office Action for U.S. Appl. No. 13/083,338, issued on Apr. 12, 2012.
U.S. Office Action for U.S. Appl. No. 13/083,338, issued on Jun. 8, 2012.
U.S. Office Action for U.S. Appl. No. 13/205,328, issued on Jan. 12, 2012.
U.S. Office Action for U.S. Appl. No. 13/205,328, issued on May 1, 2012.
U.S. Office Action for U.S. Appl. No. 13/322,961, issued on Sep. 25, 2012.
Ueda et al., "Deletion of the carboxyl-terminal exons of K-sam/FGFR2 by short homology-mediated recombination, generating preferential expression of specific messenger RNAs," Cancer Res., 59(24):6080-6086 (1999).
US Response to Notice of Non-Compliant Amendment dated Jan. 18, 2005 for U.S. Appl. No. 10/420,466.
van Oers et al., "A simple and fast method for the simultaneous detection of nine fibroblast growth factor receptor 3 mutations in bladder cancer and voided urine," *Clin. Cancer Res.*, 11:7743-7748 (2005).
Vippagunta et al., "Crystalline solids," *Advanced Drug Delivery Reviews*, 48:3-26 (2001).
Vogel et al., "Sensing extracellular matrix: an update on discoidin domain receptor function," *Cell Signaling*, 18:1108-1116 (2006).
Voluntary Amendment filed in CA App. Ser. No. 2704000, filed Aug. 6, 2013, 6 pages.
Voluntary Amendment filed on Aug. 11, 2010 for CN App. Ser. No. 200710007097.9 (with English translation).
Voluntary Amendment filed on Aug. 19, 2010 for CA App. Ser. No. 2426461.
Voluntary Amendment filed on Aug. 30, 2006 for AU App. Ser. No. 2006203099.

(56) References Cited

OTHER PUBLICATIONS

Voluntary Amendment filed on Feb. 21, 2007 for AU App. Ser. No. 2006203099.
Voluntary Amendment filed on Feb. 27, 2007 for AU App. Ser. No. 2006236039.
Voluntary Amendment filed on Feb. 9, 2010 for AU App. Ser. No. 2005283422.
Voluntary Amendment filed on Jul. 6, 2010 for AU App. Ser. No. 2005283422.
Voluntary Amendment filed on Sep. 10, 2010 for HU App. Ser. No. P0302603 (with English translation).
Voluntary Amendment for Thailand App. Ser. No. 1201000221, filed on Feb. 17, 2012.
Wakeling et al., "ZD1839 (Iressa): an orally active inhibitor of epidermal growth factor signaling with potential for cancer therapy," *Cancer Res.*, 62(20)5749-5754 (2002).
Wakui, "Chemotherapy of scirrhous gastric cancer," *Japanese Journal of Cancer and Chemotherapy*, 21(14):2398-2406 (1994) (English abstract).
Wang et al., "A Convenient Set of Bidentate Pyridine Ligands for Combinatorial Synthesis," *Tetrahedron Lett.*, 40:4779-1478 (1999).
Wang et al., "Phase II study of gemcitabine and carboplatin in patients with advanced non-smallcell lung cancer," *Cancer Chemother Pharmacol.*, 60(4):601-607 (2007).
Wang et al., "The Expression of the Proto-Oncogene C-Kit in the Blast Cells of Acute Myeloblastic Leukemia," *Leukemia*, 3(10):699-702 (1989).
Wedge et al., "AZD2171: a highly potent, orally bioavailable, vascular endothelial growth factor receptor-2 tyrosine kinase inhibitor for the treatment of cancer," *Cancer Res.*, 65(10):4389-4400 (2005).
Wells et al., "Targeting the RET Pathway in Thyroid Cancer," *Clin. Cancer Res.*, 15:7119-7123 (2009).
Willett et al., "Direct evidence that the VEGF-specific antibody bevacizumab has antivascular effects in human rectal cancer," Nat. Med., 10(2):145-1147 (2004).
Wozniak et al., "Randomized trial comparing cisplatin with cisplatin plus vinorelbine in the treatment of advanced non-small-cell lung cancer: a Southwest Oncology Group study," *J. Clin. Oncol.*, 16(7):2459-2465 (1998).
Written Amendment filed on Jun. 16, 2009 for JP App. Ser. No. 2009-123432 (with English translation).
Written Amendment filed on Sep. 21, 2011 for JP App. Ser. No. 2011-527665 (with English translation).
Written Statement filed on Jun. 16, 2009 for JP App. Ser. No. 2009-123432 (with English translation).
Written Statement filed on Sep. 21, 2011 for JP App. Ser. No. 2011-527665 (with English translation).
Yamada et al., "New technique for staining," *Monthly Medical Technology Supplementary Volume* (Apr. 1999) (with English translation).
Yamamoto et al., "E7080 (ER-203492-00), a Novel VEGF Receptor Tyrosine Kinase Inhibitor-III. Significant prolongation of life span in mice transplanted with human ovarian carcinoma based on inhibition of VEGF signaling," Abstract #50, *AACR*, Toronto, Canada (Apr. 5-9, 2003).
Yamamoto et al., "E7080 a novel multitargeted tyrosine kinase inhibitor, has direct anti-tumor activity via inhibition of KIT signaling in small cell lung cancer," Abstract #4636, *AACR*, Orlando, FL, (Mar. 27-31, 2004).
Yamamoto et al., "E7080, an oral multi-targeted tyrosine kinase inhibitor, has direct anti-tumor efficacy via inhibition of KIT signaling in gastrointestinal stromal tumor (GIST)," Abstract #4038, *97th Annual Meeting AACR*, Washington, DC. (Apr. 1-5, 2006).
Yamamoto et al., "E7080, an oral multi-targeted tyrosine kinase inhibitor, has direct anti-tumor efficacy via inhibition of Kit signaling in small cell lung cancer," *Proceedings of the American Association for Cancer Research*,45:1070-1071 (Mar. 2004).
Yanagihara et al., "Development and biological analysis of peritoneal metastasis mouse models for human scirrhous stomach cancer," *Cancer Sci.*, 96(6):323-332 (2005).
Yu, "Amorphous Pharmaceutical Solids:Preparation Characterization and Stabilization," *Advanced Drug Delivery Reviews*, 48:27-42 (2001) (XP009065056).
Zhang et al., "Overexpression of Platelet-Derived Growth Factor Receptor a in Endothelial Cells of Hepatocellular Carcinoma Associated with High Metastatic Potential," *Clin. Cancer Res.*, 11(24):8557-8563 (2005).
Zhou et al., "Correlation Research on VEGF Testing in Primary Gastric Cancer and Clinical Pathology Factor," *Journal of Practical Oncology*, 20(2):103-105 (Apr. 25, 2006) with English translation.
Zhu et al., "Fibroblast growth factor receptor 3 inhibition by short hairpin RNAs leads to apoptosis in multiple myeloma," *Mol. Cancer Ther.*, 4(5):787-798 (2005).
Zhu et al., "Inhibition of human leukemia in an animal model with human antibodies directed against vascular endothelial growth factor receptor 2. Correlation between antibody affinity and biological activity," *Leukemia*, 17:604-611 (2003).
Zieger et al., "Role of activating fibroblast growth factor receptor 3 mutations in the development of bladder tumors," *Clin. Cancer Res.*, 11:7709-7719 (2005).
Almarsson et al., "High-Throughput Surveys of Crystal Form Diversity of Highly Polymorphic Pharmaceutical Compounds," Crystal Growth & Design, Sep. 10, 2003, 3(6):927-933.
Amendment filed in KR App. Ser. No. 10-2009-7017694, dated Feb. 28, 2014, 7 pages.
Appeal for Reversal in CO App. Ser. No. 12-022608, dated Jan. 28, 2014, 17 pages (with English translation).
Argument filed in KR App. Ser. No. 10-2009-7017694, dated Feb. 28, 2014, 48 pages.
Notice of Allowance in U.S. Appl. No. 12/524,754, dated Feb. 13, 2014, 18 pages.
Notice of Allowance in U.S. Appl. No. 12/741,682, dated Feb. 7, 2014, 11 pages.
Notice of Allowance in U.S. Appl. No. 13/083,338, dated Feb. 6, 2014, 15 pages.
Notice of Allowance in U.S. Appl. No. 13/205,328, dated Jan. 30, 2014, 11 pages.
Office Action in CA App. Ser. No. 2676796, dated Dec. 30, 2013, 5 pages.
Office Action in CN App. Ser. No. 200680020317.5, dated Mar. 4, 2014, 13 pages (with English translation).
Office Action in EP App. Ser. No. 04807580.8, dated Mar. 18, 2014, 12 pages.
Office Action in EP App. Ser. No. 08704376.6, dated Feb. 24, 2014, 4 pages.
Office Action in KR App. Ser. No. 10-2009-7017694, dated Jan. 29, 2014, 26 pages (with English translation).
Office Action in PH App. Ser. No. 1-2011-502441, dated Feb. 19, 2014, 2 pages.
Office Action in U.S. Appl. No. 11/662,425, dated Feb. 27, 2014, 152 pages.
Office Action in U.S. Appl. No. 11/997,543, dated Mar. 11, 2014, 20 pages.
Office Action in U.S. Appl. No. 12/039,381, dated Jan. 9, 2014, 16 pages.
O'Reilly et al., "Hydrolysis of tert-Butyl Methyl Ether (MTBE) in Dilute Aqueous Acid," Environ. Sci. Technol., 2001, 35:3954-3961.
Patel et al., "The effect of excipients on the stability of levothyroxine sodium pentahydrate tablets," Int'l J Pharm., 2003, 264:35-43.
Response filed in PH App. Ser. No. 1-2011-502441, dated Feb. 28, 2014, 4 pages.
Response to Office Action in CN App. Ser. No. 200680020317.5 filed on Jan. 9, 2014, 7 pages (with English translation).
Response to Office Action in CN App. Ser. No. 201180030568.2 filed on Jan. 13, 2014, 46 pages (with English translation).
Response to Office Action in MX App. Ser. No. MX/a/2010/008187, dated Feb. 17, 2014, 7 pages (with English translation).
Response to Office Action in MX App. Ser. No. MX/a/2012/002011 filed on Jan. 16, 2014, 20 pages (with English translation).

(56) References Cited

OTHER PUBLICATIONS

Response to the Office Action issued for in App. Ser. No. 6415/CHENP/2008 filed on Jan. 17, 2014, 16 pages.
Search Report in EP App. Ser. No. 11798224.9, dated Mar. 21, 2014, 1 page.
Search Report in EP App. Ser. No. 11798224.9, dated Mar. 4, 2014, 6 pages.
Stahl and Wermuth, "Handbook of Pharmaceutical Salts: Properties, selection, and use," 2002, pp. 117-122.
Submission documents re RCE filed in U.S. Appl. No. 12/741,682, dated Jan. 17, 2014, 1 page.
Submission documents re RCE in U.S. Appl. No. 12/439,339, dated Jan. 27, 2014, 1 page.
Submission documents re RCE in U.S. Appl. No. 12/524,754, filed Feb. 3, 2014, 1 page.
Winkler et al., "Kinetics of vascular normalization by VEGFR2 blockade governs brain tumor response to radiation: Role of oxygenation, angiopoietin-1, and matrix metalloproteinases," Cancer Cell, Dec. 2004, 6:553-563.
Written Submission regarding hearing in IN App. Ser. No. 1571/CHENP/2007 filed on Jan. 23, 2014, 8 pages.
Zhang et al., "Synergic antiproliferative effect of DNA methyltransferase inhibitor in combination with anticancer drugs in gastric carcinoma," Cancer Sci., Sep. 2006, 97(9):938-944.
Amendment filed in U.S. Appl. No. 13/805,826, dated Sep. 9, 2013, 14 pages.
Amendment filed on Aug. 13, 2013 in JP App. Ser. No. P2009-540099, 8 pages (with English translation).
Amendment filed on Aug. 29, 2013 in CN App. Ser. No. 201280010898.X, 24 pages (with English translation).
Amendment filed on Aug. 6, 2013, for JP App. Ser. No. 2009-551518, 6 pages (with English translation).
Amendment filed on Oct. 1, 2013 in in App. Ser. No. 10502/CHENP/2012, 10 pages.
Amendment filed on Sep. 23, 2013 in AU App. Ser. No. 2011270165, 35 pages.
Amendment for IN App. Ser. No. 7026/CHENP/2013, dated Sep. 5, 2013, 8 pages.
Amendment in Canadian App. Ser. No. 2828946, dated Aug. 30, 2013, 14 pages.
Amendment in Israeli App. Ser. No. 200090, dated Oct. 2, 2013, 10 pages (with English translation).
Amendment in Korean App. Ser. No. 10-2012-7033886, dated Sep. 27, 2013, 34 pages (with English translation).
Amendment in Mexican App. Ser. No. MX/a/2012/014776, dated Oct. 21, 2013, 5 pages.
Amendment in Russian App. Ser. No. 2012158142, dated Oct. 17, 2013, 48 pages (with English translation).
Argument filed on Aug. 13, 2013 in JP App. Ser. No. 2009-540099, 10 pages (with English translation).
Argument filed on Aug. 6, 2013 for JP Patent Application No. 2009-551518, 18 pages (with English translation).
Colombian Office Action for App. Ser. No. 12-022608, dated Oct. 7, 2013, 10 pages (with English translation).
Ezzat et al., "Dual Inhibition of RET and FGFR4 Retains Medullary Thyroid Cancer Cell Growth," Clinical Cancer Research, Feb. 2005, 11:1336-1341.
Indian Office Action in App. Ser. No. 6415/CHENP/2008, dated Oct. 3, 2013, 2 pages.
Korean Office Action for App. Ser. No. 10-2009-7005657, issued on Sep. 30, 2013, 27 pages (with English translation).
Korean Office Action in KR App. Ser. No. 10-2008-7029472, dated Sep. 30, 2013, 27 pages (with English translation).
Mexican Office Action in App. Ser. No. MX/a/2010/008187, dated Aug. 21, 2013, 6 pages (with English translation).
Notice of Allowance for JP App. Ser. No. P2008-532141, dated Sep. 10, 2013, 5 pages (with English translation).
Notice of Allowance for U.S. Appl. No. 11/997,719, dated Sep. 13, 2013, 20 pages.
Notice of Allowance for U.S. Appl. No. 13/083,338, dated Sep. 26, 2013, 28 pages.
Notice of Allowance for U.S. Appl. No. 13/205,328, dated Oct. 3, 2013, 11 pages.
Notice of Allowance in EP App. Ser. No. 04818213.3, dated Sep. 19, 2013, 2 pages.
Notice of Allowance in U.S. Appl. No. 12/741,682, dated Oct. 21, 2013, 12 pages.
Notice of Allowance in U.S. Appl. No. 13/624,278, dated Sep. 16, 2013, 20 pages.
Notice of Allowance issued in CN App. Ser. No. 200880115011.7, dated Aug. 5, 2013, 4 pages (with English translation).
Office Action for PH App. Ser. No. 1-2011-502441 on Oct. 1, 2013, 1 page.
Request for Examination in CA App. Ser. No. 2713930, dated Oct. 21, 2013, 8 pages.
Request for Re-Examination in CN App. Ser. No. 200780017371.9, dated Oct. 11, 2013, 9 pages (with English translation).
Response and Amendment for CA App. Ser. No. 2652442, dated Sep. 5, 2013, 17 pages.
Response filed in IN App. Ser. No. 1571/CHENP/2007, dated Oct. 30, 2013, 9 pages.
Response to Restriction Requirement in U.S. Appl. No. 13/238,085, dated Oct. 4, 2013, 3 pages.
Sattler et al., "Targeting c-Kit mutations: basic science to novel therapies," Leukemia Research, 2004, 28S1:S11-S20.
St. Bernard et al., "Fibroblast Growth Factor Receptors as Molecular Targets in Thyroid Carcinoma," Endocrinology, Mar. 2005, 146(3):1145-1153.
Submission Document Before the Patent Office re RCE in U.S. Appl. No. 13/205,328, dated Sep. 10, 2013, 12 pages.
Submission Document re Petition on Oct. 2, 2013 in CL App. Ser. No. 2012-00412, 22 pages (with English translation).
Submission Document re RCE and Information Disclosure Statement on Sep. 19, 2013 in U.S. Appl. No. 12/741,682, 19 pages.
Submission Document re RCE and Information Disclosure Statement on Oct. 18, 2013 in U.S. Appl. No. 12/524,754, 17 pages.
US Office Action for U.S. Appl. No. 11/997,543, dated Sep. 30, 2013, 88 pages.
Agnieszka et al., "Emergence of potential biomarkers of" response to anti-angiogenic anti-tumor agents,"" International Journal of Cancer, Sep. 2010, 127(6): 1251-1258.
Application for Patent Term Adjustment in U.S. Appl. No. 12/439,339, dated Dec. 18, 2014, 8 pages.
Asano et al , "Inhibition of Tumor Growth and Metastasis by an Immunoneutralizing Monoclonal Antibody to Human Vascular Endothelial Growth Factor/Vascular Permeability Factor121," Cancer Research., 55, 5296-5301, 1995.
Correction Request in CO App. Ser. No. 12-022608, dated Dec. 24, 2014, 3 pages (with English translation).
Dietrich, "BRAF Inhibition in Refractory Hairy-Cell Leukemia," N Eng J Med., 366(21):2038-2040 (May 24, 2012).
Glen "Pre-clinical investigation and clinical development of E7080, a multi-targeted tyrosine inhibitor: implications for melanoma," Ph.D. thesis submitted to the Faculty of Medicine, Division of Cancer Sciences and Molecular Pathology, University of Glasgow, Aug. 2010, 2 pages (abstract only).
Goede, "Identification of serum angiopoietin-2 as a biomarker—for clinical outcome of colorectal cancer patients treated with bevacizumab-containing therapy," British Journal of Cancer, Oct. 2010, 103(9):1407-1414.
Helfrich et al., "Angiopoietin-2 Levels Are Associated with Disease—Progression in Metastatic Malignant Melanoma," Clinical Cancer Research, Feb. 2009, 15(4):1384-1392.
Kumar et al., "Survival and failure outcomes in primary thyroid lymphomas: A single centre experience of combined modality approach," Journal of Thyroid Research, vol. 2013, Jun. 18, 2013, 6 pages.
Marchetti et al., "Clinical Features and Outcome of Patients with Non-Small-Cell Lung Cancer Harboring Braf Mutations," J Clin Oncol., 29(26):3574-3579 (Aug. 8, 2011).
Notice of Allowance in EP App. Ser. No. 04807580.8, dated Dec. 15, 2014, 103 pages.

(56) References Cited

OTHER PUBLICATIONS

Notice of Allowance in EP App. Ser. No. 07743994.1, dated May 8, 2015, 51 pages.
Notice of Allowance in EP App. Ser. No. 08846814.5, dated Jan. 8, 2015, 36 pages.
Notice of Allowance in IL App. Ser. No. 205512, dated Feb. 15, 2015, 5 pages (with English translation).
Notice of Allowance in KR App. Ser. No. 10-2010-7011023, dated Mar. 24, 2015, 3 pages (with English translation).
Notice of Allowance in KR App. Ser. No. 10-2010-7018835, dated Jan. 20, 2015, 3 pages (with English translation).
Notice of Allowance in KR App. Ser. No. 10-2012-7003846, dated Feb. 3, 2015, 3 pages.
Notice of Allowance in MX App. Ser. No. MX/a/2012/014776, dated Mar. 18, 2015, 3 pages (with English translation).
Notice of Allowance in RU App. Ser. No. 2012103471, dated Dec. 19, 2014, 12 pages (with English translation).
Notice of Allowance in RU App. Ser. No. 2012158142, dated May 5, 2015, 15 pages (with English translation).
Office Action in CA App. Ser. No. 2676796, dated Jan. 29, 2015, 5 pages.
Office Action in CA App. Ser. No. 2704000, dated Mar. 27 ,2015, 3 pages.
Office Action in CA App. Ser. No. 2713930, dated Jan. 30, 2015, 5 pages.
Office Action in CL App. Ser. No. 2012-00412, dated Jan. 28, 2015, 17 pages (with English translation).
Office Action in CN App. Ser. No. 200780017371.9, dated Dec. 11, 2014, 9 pages (with English translation).
Office Action in CN App. Ser. No. 200780017371.9, dated May 15, 2015, 17 pages (with English translation).
Office Action in CN App. Ser. No. 201280010898.X, dated Mar. 30, 2015, 13 pages (with English translation).
Office Action in EP App. Ser. No. 12774278.1, dated Mar. 9, 2015, 6 pages.
Office Action in EP Application No. 10809938.3, dated Feb. 10, 2015, 4 pages.
Office Action in HU App. Ser. No. P0302603, dated Apr. 7, 2015, 4 pages (with English translation).
Office Action in IL App. Ser. No. 223695, dated Feb. 16, 2015, 5 pages (with English translation).
Office Action in JP App. Ser. No. P2012-521531, dated Mar. 3, 2015, 6 pages (with English translation).
Office Action in MX App. Ser. No. MX/a/2013/009931, dated Apr. 9, 2015, 3 pages (with English translation).
Office Action in NO App. Ser. No. 20063383, dated Apr. 15, 2015, 2 pages (with English translation).
Office Action in PH App. Ser. No. Jan. 2011-502441, dated May 8, 2015, 2 pages.
Office Action in RU App. Ser. No. 2012158142, dated Feb. 12, 2015, 21 pages (with English translation).
Office Action in TW App. Ser. No. 100104281, dated Dec. 9, 2014, 13 pages (with English translation).
Office Action in U.S. Appl. No. 12/039,381, dated Feb. 26, 2015, 13 pages.
Official Notification in CA App. Ser. No. 2771403, dated Dec. 16, 2014, 1 page.
Official Notification in CO App. Ser. No. 12-022608, dated Jan. 6, 2015, 8 pages (with English translation).
Park, "Serum Angiopoietin-2 as a Clinical Market for Lung Cancer," Chest, Jul. 2007, 132(1):200.
Payment of Final Fee and Amendment after Allowance in CA App. Ser. No. 2771403, dated Nov. 24, 2014, 3 pages.
Ren, "Advances in Medical Therapy of Melanoma," Journal of Practical Oncology, No. 2., vol. 25, Dec. 31, 2010, pp. 137-140.
Reply to Notice of Allowance in U.S. Appl. No. 11/662,425, dated Jan. 20, 2015, 5 pages.
Response in Reexamination and Invalidation Procedure in CN App. Ser. No. 200780017371.9, dated Jan. 19, 2015, 8 pages (with English translation).
Response to Communication in EP App. Ser. 07743994.1, dated Dec. 22, 2014, 62 pages.
Response to Examiner's Report in CL App. Ser. No. 2012-00412, dated Mar. 30, 2015, 16 pages (with English translation).
Response to Examiner's Substantive Report in CL App. Ser. No. 2012-00412, dated Nov. 28, 2014, 39 pages (with English translation).
Response to Office Action in CA App. Ser. No. 2704000, dated Dec. 19, 2014, 13 pages.
Response to Office Action in EP App. Ser. No. 10809938.3, dated Apr. 13, 2015, 12 pages.
Response to office action in EP App. Ser. No. 12786619.2, dated May 12, 2015, 99 pages.
Response to Office Action in MX App. Ser. No. MX/a/2012/014776, dated Jan. 7, 2015, 20 pages (with English translation).
Response to Office Action in MX App. Ser. No. MX/a/2013/009931, dated Dec. 9, 2014, 24 pages (with English translation).
Response to Office Action in RU App. Ser. No. 2012158142, dated Apr. 13, 2015, 11 pages (with English translation).
Response to Office Action in U.S. Appl. No. 13/923,858, filed Apr. 1, 2015, 12 pages.
Schlumberger et al., "Lenvatinib versus Placebo in Radioiodine-Refractory Thyroid Cancer," N Engl J Med., 372(7):621-630, Feb. 12, 2015.
Search Report in EP App. Ser. No. 12793322.4, dated May 26, 2015, 9 pages.
Sharma et al., "Thyroid Cancer," Feb. 18, 2015, pp. 1-16.
Stjepanovic and Capdevila, "Multikinase inhibitors in the treatment of thyroid cancer: specific role of lenvatinib," Biologics: Targets and Therapy, 8:129-139, Aug. 2014.
Submission Document in EP App. Ser. No. 09705712.9, dated Feb. 24, 2015, 196 pages.
Submission Document in PH App Ser. No. 1-2011-502441, dated May 22, 2015, 25 pages.
Submission Documents in EG App. Ser. No. PCT 283/2012, dated Jan. 18, 2015, 26 pages (with English translation).
Submission Documents in TW App. Ser. No. 100104281, dated Mar. 9, 2015, 12 pages (with English translation).
Submission of Claims in IL App. Ser. No. 223695, dated Jan. 17, 2015, 16 pages.
Vianna et al., "The histological rarity of thyroid cancer," Brazilian Journal of Otorhinolaryngology, 2012 78(4):48-51.
Yamada et al., "Phase 1 Dose-Escalation Study and Biomarker Analysis of E7080 in Patients with Advanced Solid Tumors," (with supplementary data), Clinical Cancer Research, Mar. 2011, 17(8):2528-2537.
Yamamoto et al., "Lenvatinib, an angiogenesis inhibitor targeting VEGFR/FGFR, shows broad antitumor activity in human tumor xenograft models associated with microvessel density and pericyte coverage," Vascular Cell, 6(18):1-13, 2014.
Zurita et al., "A cytokine and angiogenic factor (CAF) analysis in plasma for selection of sorafenib therapy in patients with metastatic renal cell carcinoma," Annals of oncology, Apr. 2011, 23(1):46-52.
Zurita et al., "Circulating biomarkers for vascular-endothelial growth factor inhibitors in renal cell carcinoma," Cancer, May 2009, 115(S10):2346-2354.
Amendment in Israeli Application No. 217197, dated Dec. 24, 2015, 5 pages, with English translation.
Australian Notice of Allowance in Application No. 2011270165, dated Dec. 14, 2015, 3 pages.
Australian Office Action in Application No. 2011270165, dated Nov. 6, 2015, 3 pages.
Australian Office Action in Application No. 2012246490, dated Apr. 20, 2016, 3 pages.
Australian Office Action in Application No. 2012246490, dated Feb. 5, 2016, 3 pages.
Australian Second Statement of Proposed Amendments in Application No. 2011270165, dated Dec. 4, 2015, 5 pages.
Australian Voluntary Amendment Submitted in Application No. 2010285740, dated Nov. 20, 2015, 11 pages.
Brazilian Office Action in Application No. PI0418200-6, dated Jun. 16, 2015, 1 page.

(56) References Cited

OTHER PUBLICATIONS

Canadian Notice of Allowance in Application No. 2676796, dated Oct. 8, 2015, 1 page.
Canadian Office Action in Application No. 2704000, dated Jan. 14, 2015, 3 pages.
Canadian Office Action in Application No. 2704000, dated Jul. 14, 2015, 3 pages.
Canadian Office Action in Application No. 2713930, dated Mar. 7, 2016, 5 pages.
Canadian Office Action in Application No. 2713930, dated Sep. 15, 2015, 3 pages.
Canadian Office Action in Application No. 2802644, dated Oct. 23, 2015, 6 pages.
Canadian Office Action in Application No. 2828496, dated Nov. 30, 2015, 4 pages.
Canadian Response to Office Action in Application No. 2802644, dated Apr. 18, 2016, 9 pages.
Canadian Submission Documents in Application No. 2713930, dated Jun. 22, 2015, 8 pages.
Chinese Notice of Allowance in Application No. 201280010898.X, dated Sep. 2, 2015, 4 pages.
Chinese Submission Documents in Application No. 201280010898.X, dated Jun. 15, 2015, 12 pages.
Chinese Voluntary Amendment in Application No. 201510031628.2, dated Oct. 10, 2015, 5 pages, with English translation.
European Notice of Allowance in Application No. 10809938.3, dated Jan. 8, 2016, 2 pages.
European Notice of Allowance in Application No. 10809938.3, dated Sep. 3, 2015, 30 pages.
European Notice of Allowance in Application No. 11798224.9, dated Sep. 29, 2015, 37 pages.
European Notice of Allowance in Application No. 12774278.1, dated Jun. 29, 2015, 34 pages.
European Office Action in Application No. 12786619.2, dated Dec. 8, 2015, 4 pages.
European Search Report in Application No. 12793322.4, dated Sep. 10, 2015, 13 pages.
Herbst and Khuri et al., "Mode of action of docetaxel—a basis for combination with novel anticancer agents," Cancer Treat Rev, 29:407-415, 2003.
Hungarian Amendment to the Specification in Application No. P0302603, dated Jul. 7, 2015, 45 pages, with English translation.
Hungarian Notice of Allowance in Application No. P0302603, dated Aug. 19, 2015, 4 pages, with English translation.
Hungarian Office Action in Application No. P0302603, dated Nov. 26, 2015, 4 pages.
Indonesian Office Action in Application No. W-00201201031, dated Mar. 14, 2016, 4 pages, with English translation.
International Preliminary Report on Patentability in Application No. PCT/JP2013/084052, dated Jul. 2, 2015, 7 pages.
International Search Report and Written Opinion in Application No. PCT/JP2014/063134, dated Sep. 9, 2014, 8 pages.
Israeli Office Action in Application No. 217197, dated Oct. 25, 2015, 4 pages.
Israeli Office Action in Application No. 223695, dated Aug. 25, 2015, 6 pages, with English translation.
Israeli Office Action in Application No. 227558, dated Aug. 2, 2015, 5 pages, with English translation.
Israeli Office Action in Application No. 227558, dated Mar. 13, 2016, 5 pages, with English translation.
Israeli Office Action in Application No. 238463, dated Oct. 28, 2015, 5 pages, with English translation.
Israeli Submission Documents in Application No. 223695, dated Dec. 24, 2015, 6 pages, with English translation.
Israeli Submission Documents in Application No. 223695, dated May 4, 2015, 4 pages, with English translation.
Israeli Submission Documents in Application No. 227558, dated Nov. 30, 2015, 3 pages.
Japanese Notice of Allowance in Application No. P2011-206481, dated Aug. 4, 2015, 7 pages, with English translation.
Japanese Office Action in Application No. P2011-206481, dated Jun. 2, 2015, 7 pages, with English translation.
Japanese Office Action in Application No. P2012-521531, dated Sep. 29, 2015, 4 pages, with English tmnslation.
Japanese Office Action in Application No. P2013-510994, dated Jul. 28, 2015, 5 pages, with English tmnslation.
Japanese Office Action in Application No. P2013-510994, dated Jun. 9, 2015, 6 pages, with English translation.
Japanese Office Action in Application No. P2014-513691, dated Mar. 8, 2016, 6 pages, with English tmnslation.
Kato et al., "Effects of lenvatinib on tumor-associated macrophages enhance antitumor activity of PD-1 signal Inhibitors," Poster A92, Nov. 6, 2015, 1 page.
Kato et al., "Effects of lenvatinib on tumor-associated macrophages enhance antitumor activity of PD-1 signal Inhibitors," Molecular Targets and Cancer Therapeutics, Abstract A92, Nov. 6, 2015, 1 page.
Kharkyevitch, "Farmakologiya," Third addition, and revised supplemented, Moscow, "Meditsina," 1987, partial translation, 5 pages.
Korean Request for Examination in Application No. 10-2012-7033886, dated Aug. 26, 2015, 12 pages, with English translation.
Macedonian Notice of Allowance in Application No. P/2015/231, dated Oct. 13, 2015, 2 pages, with English translation.
Mexican Notice of Allowance in Application No. MX/a/2013/009931, dated Jun. 29, 2015, 3 pages, with English translation.
Mexican Office Action in Application No. MX/a/2014/010594, dated Oct. 13, 2015, 8 pages, with English translation.
Mexican Submission Documents in Application No. MX/a/2014/010594, dated Oct. 8, 2015, 10 pages, with English translation.
Mexican Submission Documents in Application No. MX/a/2014/010594, dated Sep. 24, 2015, 2 pages, with English translation.
Norwegian Office Action in Application No. 20063383, dated Mar. 15, 2016, 6 pages, with Translation.
Norwegian Submission Documents in Application No. 20063383, dated Jun. 19, 2015, 8 pages.
Noy et al., "Tumor-Associated Macrophages: From Mechanisms to Therapy," Immunity 41:49-61, Jul. 17, 2014.
Oya, "mTOR inhibitors," Nippon Rinsho, 68(6):1067-1072, Jun. 1, 2010, with English abstract.
Peruvian Office Action in Application No. 2081-2011, dated Mar. 23, 2016, 12 pages, with English translation.
Response to Canadian Office Action in Application No. 2704000, dated Dec. 24, 2015, 11 pages.
Response to Canadian Office Action in Application No. 2828946, dated Feb. 5, 2016, 6 pages.
Russian Office Action in Application No. 2013140169, dated Nov. 6, 2015, 10 pages, with English translation.
Russian Office Action in Application No. 2015148193, dated Jan. 27, 2016, 4 pages, with English translation.
Schlumberger et al., "Lenvatinib versus Placebo in Radioiodine-Refractory Thyroid Cancer (with supplementary material)," The New England Journal of Medicine 2015; 372, Feb. 12, 2015, p. 621-630.
Tahara et al., "Presentation slides at European Society for Medical Oncology (ESMO) 2014 Congress (held in Madrid, Spain on Sep. 26-30, 2014)," Sep. 27, 2014, 18 pages.
Tahara et al., "The abstract of presentation slides at European Society for Medical Oncology (ESMO) 2014 Congress (held in Madrid, Spain on Sep. 26-30, 2014)," Sep. 27, 2014, 6 pages.
Taiwanese Notice of Allowance in Application No. 100104281, dated Jun. 9, 2015, 4 pages, with English translation.
Thailand Request for Examination in Application No. 0401005163, dated Aug. 21, 2015, 29 pages, with English translation.
U.S. Certificate of Correction in U.S. Appl. No. 12/524,754, dated Aug. 11, 2015, 1 page.
U.S. Certificate of Correction in U.S. Appl. No. 12/741,682, dated Aug. 4, 2015, 2 pages.
U.S. Certificate of Correction in U.S. Appl. No. 13/624,278, dated Aug. 18, 2015, 1 page.
U.S. Notice of Allowance in U.S. Appl. No. 14/438,366, dated Dec. 18, 2015, 5 pages.

(56) References Cited

OTHER PUBLICATIONS

U.S. Notice of Allowance in U.S. Appl. No. 14/438,366, dated Feb. 12, 2016, 7 pages.
U.S. Notice of Appeal and Pre-Appeal Brief in U.S. Appl. No. 13/923,858, dated Nov. 25, 2015, 8 pages.
U.S. Office Action in U.S. Appl. No. 12/039,381, dated Oct. 7, 2015, 22 pages.
U.S. Office Action in U.S. Appl. No. 13/923,858, dated Jan. 7, 2016, 2 pages.
U.S. Office Action in U.S. Appl. No. 13/923,858, dated Jul. 29, 2015, 15 pages.
U.S. Office Action in U.S. Appl. No. 14/438,366, dated Sep. 28, 2015, 8 pages.
U.S. Preliminary Amendment in U.S. Appl. No. 14/122,339, dated Aug. 27, 2015, 7 pages.
U.S. Response to Office Action in U.S. Appl. No. 12/039,381, dated Dec. 22, 2015, 10 pages.

* cited by examiner

PHARMACEUTICAL COMPOSITIONS OF 4-(3-CHLORO-4-(CYCLOPROPYLAMINO-CARBONYL)AMINOPHENOXY)-7-METHOXY-6-QUINOLINECARBOXAMIDE

The present application is a continuation of U.S. application Ser. No. 11/662,425, filed Apr. 4, 2008, which is a U.S. National Phase of PCT/JP2005/016941, filed Sep. 14, 2005, which claims the benefit of Japanese Application No. 2004-272625, filed on Sep. 17, 2004, the disclosures of which are hereby incorporated herein by reference in their entirety.

TECHNICAL FIELD

The present invention relates to pharmaceutical compositions.

BACKGROUND ART

Nitrogen-containing aromatic ring derivatives disclosed in Patent Document 1 have actions in vitro such as 1) the inhibition of infiltrating tube formation by vascular endothelial cells induced by an angiogenic factor mixture solution; 2) the inhibition of tube formation by vascular endothelial cells induced specifically by a single angiogenic factor; 3) the inhibition of angiogenic factor receptor kinase; and 4) the inhibition of cancer cell growth, and hence are extremely useful as angiogenic inhibitors and the like.

[Patent Document 1]: WO 02/32872

DISCLOSURE OF THE INVENTION

Problems to be Solved by the Invention

The present inventors have found that while studying on formulating the above nitrogen-containing aromatic ring derivatives, pharmaceutical compositions containing the above nitrogen-containing aromatic ring derivatives as active ingredients are sometimes rendered unstable. Specifically, of the nitrogen-containing aromatic ring derivatives disclosed in Patent Document 1, this holds true for the nitrogen-containing aromatic ring derivatives having a structure wherein the quinoline skeleton is linked to another heterocyclic group through an ether bond. In particular, in pharmaceutical compositions, such nitrogen-containing aromatic ring derivatives are readily decomposed under humidified and heated storage conditions; and moreover, gelation readily occurs on the surface of the pharmaceutical compositions, so that when the pharmaceutical compositions are stored under humidified conditions, delayed dissolution of the active ingredients may occur due to moisture absorption.

Accordingly, an object of the present invention is to provide a stable pharmaceutical composition comprising a nitrogen-containing aromatic ring derivative, wherein under humidified and heated storage conditions, the decomposition of the above derivative is sufficiently reduced, or the gelation on the surface of the pharmaceutical composition is sufficiently inhibited.

Means for Solving the Problems

To attain the above object, the present invention provides the pharmaceutical composition described below.

The pharmaceutical composition comprising:
an active ingredient consisting of 4-(3-chloro-4-(cyclopropylaminocarbonyl)aminophenoxy)-7-methoxy-6-quinolinecarboxamide represented by Formula (1) described below, salt thereof, or solvate of the foregoing; and
(i) a compound, a 5% (w/w) aqueous solution or suspension of which has a pH of 8 or more; and/or
(ii) silicic acid, salt thereof, or solvate of the foregoing.

[Formula 1]

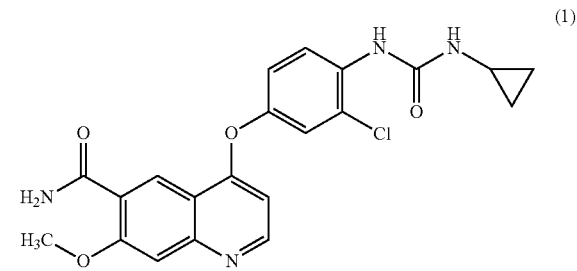

(1)

In such pharmaceutical composition, the decomposition of the compound represented by Formula (1), an active ingredient, under humidified and heated storage conditions is sufficiently reduced. Moreover, the gelation on the surface of the pharmaceutical composition is inhibited, and thereby the problem of delayed dissolution of the active ingredient after the pharmaceutical composition has been kept under humidified storage conditions is solved. Therefore, difficulties during a disintegration test or a dissolution test caused by the surface gelation of the pharmaceutical composition are eliminated, and humidity and the like do not affect the pharmaceutical composition so that the quality of the pharmaceutical composition can be ensured for a long time.

It is considered that under humidified and heated storage conditions, the suppression of the decomposition is brought about mainly by (i) the compound whose pH of a 5% (w/w) aqueous solution or suspension thereof is 8 or more, whereas the inhibition of the gelation is brought about mainly by (ii) silicic acid, salt thereof, or solvate of the foregoing. Therefore, according to requirements for the pharmaceutical composition, (i) or (ii) can be added alone or in combination thereto.

Further, it is considered that the decomposition of 4-(3-chloro-4-(cyclopropylaminocarbonyl)aminophenoxy)-7-methoxy-6-quinolinecarboxamide (hereinafter, also referred to as the "medicament X"), salt thereof, or solvate of the foregoing under humidified and heated storage conditions proceed based on the following mechanism (hereinafter, also the decomposed product having a quinoline skeleton is referred to as the "decomposed product A" and the decomposed product having 3-chloro-4-(cyclopropylaminocarbonyl)amino group as the "decomposed product B").

[Formula 2]

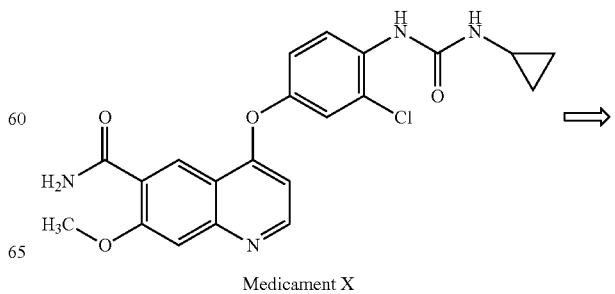

Medicament X

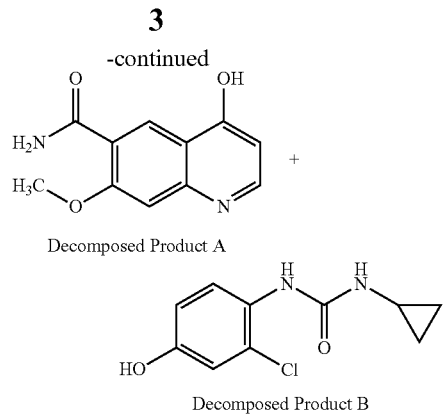

Decomposed Product A

Decomposed Product B

According to these findings, a process for improving stability of the pharmaceutical composition and a process for inhibiting gelation thereof are provided. Specifically, provided are a process for improving stability of the pharmaceutical composition comprising an active ingredient consisting of the compound represented by Formula (1) described above, salt thereof, or solvate of the foregoing by the process of adding the compound whose pH of a 5% (w/w) aqueous solution or suspension thereof is 8 or more, and a process for inhibiting gelation of the pharmaceutical composition comprising an active ingredient consisting of the compound represented by Formula (1) described above, salt thereof, or solvate of the foregoing by the process of adding silicic acid, salt thereof, or solvate of the foregoing.

In the present invention, (i) the compound whose pH of a 5% (w/w) aqueous solution or suspension thereof is 8 or more is preferably one ore more selected from the group consisting of magnesium oxide, calcium oxide, sodium carbonate, disodium hydrogenphosphate, sodium citrate, dipotassium hydrogenphosphate, sodium acetate, sodium hydrogencarbonate, and sodium hydroxide; and (ii) silicic acid, salt thereof, or solvate of the foregoing is preferably one or more selected from the group consisting of light anhydrous silicic acid, silicon dioxide hydrate, calcium silicate, magnesium silicate, magnesium aluminosilicate, magnesium aluminometasilicate, magnesium aluminum silicate, synthetic aluminum silicate, and hydrous silicic dioxide.

Effect of the Invention

Provided is the highly stable pharmaceutical composition comprising a nitrogen-containing aromatic ring derivative, wherein under humidified and heated storage conditions, the decomposition of the above derivative is sufficiently reduced, or the gelation on the surface of the pharmaceutical composition is sufficiently inhibited.

BEST MODE FOR CARRYING OUT THE INVENTION

Figure 1:
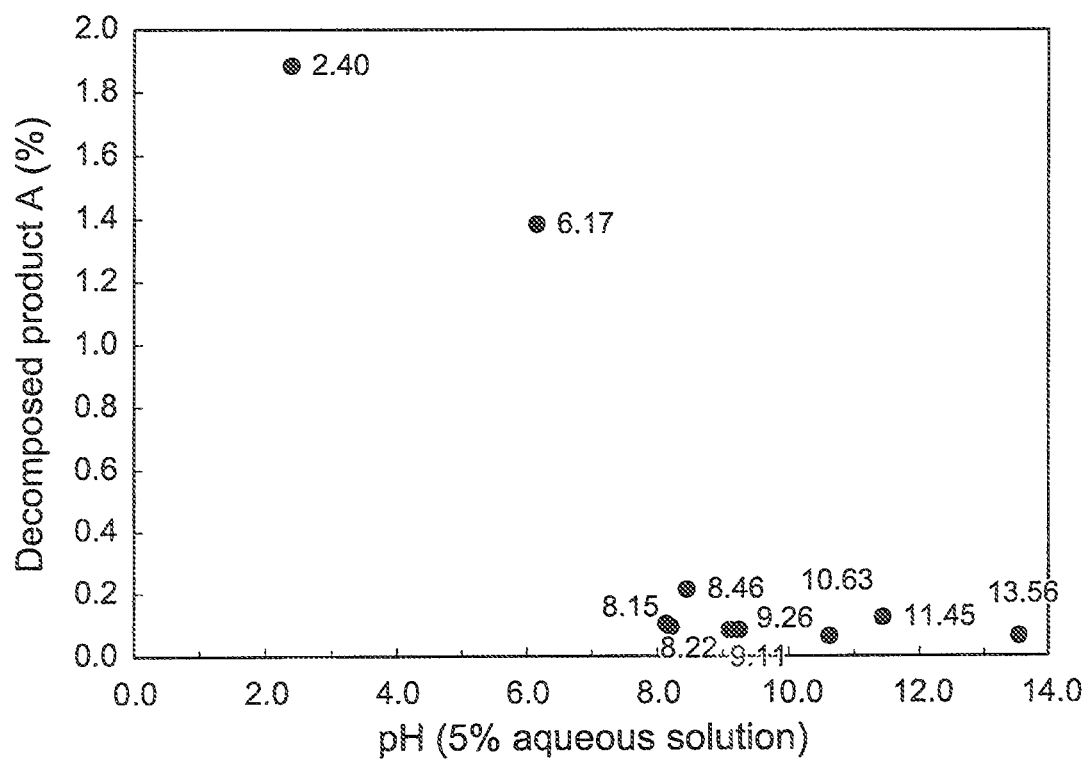
FIG. 1 illustrates the relationship between pH and the decomposed product A.

An embodiment of the present invention is explained in detail in the following paragraphs. Herein, the expression "having a diffraction peak at a diffraction angle (2θ±0.2°) of X°" means to have a diffraction peak at a diffraction angle (2θ) of from (X−0.2)° to (X+0.2)°. In general, a diffraction angle (2θ) in a powder X-ray diffraction has an error within a range of ±0.2°, and hence it should be understood that the values of the diffraction angles may include numerals on the order of ±0.2°. Accordingly, the present invention encompasses not only crystals having completely matching diffraction angles of the peaks in a powder X-ray diffraction, but also crystals having matching diffraction angles of the peaks within the errors of about ±0.2°.

(Active Ingredient)

The pharmaceutical composition in accordance with the present invention comprises the compound represented by Formula (1), salt thereof, or solvate of the foregoing as an active ingredient. The active ingredient represented by Formula (1) may be the polymorphic crystals (A') or the polymorphic crystals (B') described below.

As the polymorphic crystals (A'), the polymorphic crystals (A') of 4-(3-chloro-4-(cyclopropylaminocarbonyl) aminophenoxy)-7-methoxy-6-quinolinecarboxamide having a diffraction peak at a diffraction angle (2θ±0.2°) of 15.75° in a powder X-ray diffraction can be employed. This polymorphic crystals (A') may also have diffraction peaks at diffraction angles (2θ±0.2°) of 9.98° and 11.01° in a powder X-ray diffraction.

In an infrared spectrum (potassium bromide), these polymorphic crystals (A') may preferably have absorbance at $3452.3±2.5$ $cm^{-1}$ and also at $1712.2±1.0$ $cm^{-1}$.

As the polymorphic crystals (B'), the polymorphic crystals (B') of 4-(3-chloro-4-(cyclopropylaminocarbonyl) aminophenoxy)-7-methoxy-6-quinolinecarboxamide having a diffraction peak at a diffraction angle (2θ±0.2°) of 21.75° in a powder X-ray diffraction can be employed. This polymorphic crystals (B') may also have diffraction peaks at diffraction angles (2θ±0.2°) of 12.43° and 16.56° in a powder X-ray diffraction.

In an infrared spectrum (potassium bromide), these polymorphic crystals (B'), active ingredients, may preferably have absorbance at $1557.6±1.0$ $cm^{-1}$ and also at $1464.4±1.0$ $cm^{-1}$.

It is particularly preferred that the active ingredient represented by Formula (1) is salts, solvates, or crystals of these described below.

In particular, a suitable active ingredient is crystals of hydrochloride, hydrobromide, p-toluenesulfonate, sulfate, methanesulfonate, or ethanesulfonate of 4-(3-chloro-4-(cyclopropylaminocarbonyl)aminophenoxy)-7-methoxy-6-quinolinecarboxamide or of solvate thereof.

Specifically, crystals of methanesulfonate of 4-(3-chloro-4-(cyclopropylaminocarbonyl)aminophenoxy)-7-methoxy-6-quinolinecarboxamide or solvate thereof; crystals of ethanesulfonate of 4-(3-chloro-4-(cyclopropylaminocarbonyl) aminophenoxy)-7-methoxy-6-quinolinecarboxamide or solvate thereof; crystals of methanesulfonate of 4-(3-chloro-4-(cyclopropylaminocarbonyl)aminophenoxy)-7-methoxy-6-quinolinecarboxamide; crystals of hydrate of methanesulfonate of 4-(3-chloro-4-(cyclopropylaminocarbonyl)

aminophenoxy)-7-methoxy-6-quinolinecarboxamide; crystals of dimethyl sulfoxide solvate of methanesulfonate of 4-(3-chloro-4-(cyclopropylaminocarbonyl)aminophenoxy)-7-methoxy-6-quinolinecarboxamide; crystals of acetic acid solvate of methanesulfonate of 4-(3-chloro-4-(cyclopropylaminocarbonyl)aminophenoxy)-7-methoxy-6-quinolinecarboxamide; crystals of ethanesulfonate of 4-(3-chloro-4-(cyclopropylaminocarbonyl)aminophenoxy)-7-methoxy-6-quinolinecarboxamide; and crystals of dimethyl sulfoxide solvate of ethanesulfonate of 4-(3-chloro-4-(cyclopropylaminocarbonyl)aminophenoxy)-7-methoxy-6-quinolinecarboxamide are suitable.

The crystals of methanesulfonate of 4-(3-chloro-4-(cyclopropylaminocarbonyl)aminophenoxy)-7-methoxy-6-quinolinecarboxamide are preferably the crystals (A), the crystals (B), or the crystals (C) described below.

Specifically, the crystals (A) having diffraction peaks at diffraction angles (2θ±0.2°) of 9.65° and 18.37° in a powder X-ray diffraction; the crystals (B) having diffraction peaks at diffraction angles (2θ±0.2°) of 5.72° and 13.84° in a powder X-ray diffraction; and the crystals (C) having diffraction peaks at diffraction angles (2θ±0.2°) of 14.20° and 17.59° in a powder X-ray diffraction are preferred.

Further, the crystals of hydrate of methanesulfonate of 4-(3-chloro-4-(cyclopropylaminocarbonyl)aminophenoxy)-7-methoxy-6-quinolinecarboxamide are preferably the crystals (F) having diffraction peaks at diffraction angles (2θ±0.2°) of 8.02° and 18.14° in a powder X-ray diffraction; and the crystals of acetic acid solvate of methanesulfonate of 4-(3-chloro-4-(cyclopropylaminocarbonyl)aminophenoxy)-7-methoxy-6-quinolinecarboxamide are preferably the crystals (I) having diffraction peaks at diffraction angles (2θ±0.2°) of 9.36° and 12.40° in a powder X-ray diffraction.

Moreover, the crystals of ethanesulfonate of 4-(3-chloro-4-(cyclopropylaminocarbonyl)aminophenoxy)-7-methoxy-6-quinolinecarboxamide are preferably the crystals (α) having diffraction peaks at diffraction angles (2θ±0.2°) of 15.70° and 17.18° in a powder X-ray diffraction; and the crystals of ethanesulfonate of 4-(3-chloro-4-(cyclopropylaminocarbonyl)aminophenoxy)-7-methoxy-6-quinolinecarboxamide are preferably the crystals (β) having diffraction peaks at diffraction angles (2θ±0.2°) of 6.48° and 9.58° in a powder X-ray diffraction.

(Process for Preparing the Active Ingredient)

As for the process for preparing the compound represented by Formula (1), the description in WO 02/32872 can be used as a reference. The processes for preparing the polymorphic crystals (A') and the polymorphic crystals (B') are described in the following paragraphs.

The polymorphic crystals (A') can be obtained by a preparation process described below: 4-(3-chloro-4-(cyclopropylaminocarbonyl)aminophenoxy)-7-methoxy-6-quinolinecarboxamide is dissolved in an organic solvent, a good solvent (for example, dimethyl sulfoxide, dimethylimidazolidine, 1-methyl-2-pyrrolidinone, N,N-dimethylformamide, N,N-dimethylacetamide, acetic acid, sulfolane, etc.), and then thereto a poor solvent (for example, water, acetone, acetonitrile, ethyl acetate, isopropyl acetate, methanol, ethanol, n-propanol, isopropanol, or a mixture thereof, etc.) is admixed rapidly (for example, within 10 min.).

The polymorphic crystals (A') can be obtained by another preparation process described below: 4-(3-chloro-4-(cyclopropylaminocarbonyl)aminophenoxy)-7-methoxy-6-quinolinecarboxamide is dissolved while stirring in an organic solvent, a good solvent (for example, dimethyl sulfoxide, dimethylimidazolidine, 1-methyl-2-pyrrolidinone, N,N-dimethylformamide, N,N-dimethylacetamide, acetic acid, sulfolane, etc.), and then thereto a poor solvent (for example, water, acetone, acetonitrile, ethyl acetate, isopropyl acetate, methanol, ethanol, n-propanol, isopropanol, or a mixture thereof, etc.) is admixed so that the resultant crystals precipitate when the stirring is stopped.

The polymorphic crystals (A') can be obtained by still another preparation process described below: 7-methoxy-4-chloroquinoline-6-carboxamide and 1-(2-chloro-4-hydroxyphenyl)-3-cyclopropylurea are reacted in the presence of a base (for example, potassium t-butoxide, cesium carbonate, potassium carbonate, etc.) in an organic solvent that works a good solvent for 4-(3-chloro-4-(cyclopropylaminocarbonyl)aminophenoxy)-7-methoxy-6-quinolinecarboxamide (for example, dimethyl sulfoxide (DMSO), dimethylimidazolidinone, 1-methyl-2-pyrrolidinone, N,N-dimethylformamide, N,N-dimethylacetamide, sulfolane, etc.), and then thereto a poor solvent is admixed rapidly (for example, within 10 min.).

More specifically, for example, to a mixture of 1-(2-chloro-4-hydroxyphenyl)-3-cyclopropylurea, 7-methoxy-4-chloroquinoline-6-carboxamide (one equivalent or more based on 1-(2-chloro-4-hydroxyphenyl)-3-cyclopropylurea), and potassium t-butoxide (one equivalent or more based on 1-(2-chloro-4-hydroxyphenyl)-3-cyclopropylurea), DMSO in a volume 5 to 10 times based on 1-(2-chloro-4-hydroxyphenyl)-3-cyclopropylurea is added at room temperature, and then the mixture is heated to from 55 to 75° C. while stirring for 20 hr. or longer to allow the reaction to proceed. To this reaction mixture, while heating at from 60 to 65° C. and stirring, a poor solvent (20 to 50% acetone in water or 20 to 50% 2-propanol in water) in a volume 15 times based on 1-(2-chloro-4-hydroxyphenyl)-3-cyclopropylurea is introduced within 8 min. so that crystals can appear. Further, it is preferred to add the seed crystals when the poor solvent is introduced to allow the crystals to appear. The polymorphic crystals (A') can be obtained by stirring the resulting reaction mixture, in which the crystals appeared, at the temperature ranging from room temperature to 40° C. generated by heating for 3 hr. or longer to collect the crystals by filtration.

The polymorphic crystals (B') can be obtained by a preparation process described below: 4-(3-chloro-4-(cyclopropylaminocarbonyl)aminophenoxy)-7-methoxy-6-quinolinecarboxamide is dissolved in an organic solvent, a good solvent (for example, DMSO, dimethylimidazolidine, 1-methyl-2-pyrrolidinone, N,N-dimethylformamide, N,N-dimethylacetamide, acetic acid, sulfolane, etc.), and then thereto a poor solvent (for example, water, acetone, acetonitrile, ethyl acetate, isopropyl acetate, methanol, ethanol, n-propanol, isopropanol, or a mixture thereof, etc.) is admixed slowly (for example, for 1 hr. or longer). When the poor solvent is admixed slowly, crystals appeared, but when stirring is stopped, the resultant crystals spreads all over the solvent.

More specifically, for example, to 4-(3-chloro-4-(cyclopropylaminocarbonyl)aminophenoxy)-7-methoxy-6-quinolinecarboxamide, a good solvent (DMSO or 1-methyl-2-pyrrolidinone) in a volume from 4 to 5 times based on 4-(3-chloro-4-(cyclopropylaminocarbonyl)aminophenoxy)-7-methoxy-6-quinolinecarboxamide is added, and then the mixture is heated to 80° C. or higher while stirring to dissolve the solute. To this mixture, while heating at from 65 to 85° C. and stirring, a poor solvent (isopropyl acetate, ethyl acetate, methanol, or isopropanol) in a volume from 10 to 20 times based on 4-(3-chloro-4-(cyclopropylaminocarbonyl)aminophenoxy)-7-methoxy-6-quinolinecarboxamide is introduced over 30 min. or longer so that crystals can appear.

Further, it is preferred to add the seed crystals when the poor solvent is introduced to allow the crystals to appear. The polymorphic crystals (B') can be obtained by stirring the resulting reaction mixture, in which the crystals appeared, while heating at 70° C. or higher for 30 min. or longer, and further by stirring at room temperature to collect the crystals by filtration.

The polymorphic crystals (B') can be obtained by another preparation process described below: 4-(3-chloro-4-(cyclopropylaminocarbonyl)aminophenoxy)-7-methoxy-6-quinolinecarboxamide is dissolved while stirring in an organic solvent, a good solvent (for example, DMSO, dimethylimidazolidine, 1-methyl-2-pyrrolidinone, N,N-dimethylformamide, N,N-dimethylacetamide, acetic acid, sulfolane, etc.), and then a poor solvent (for example, water, acetone, acetonitrile, ethyl acetate, isopropyl acetate, methanol, ethanol, n-propanol, isopropanol, or a mixture thereof, etc.) is admixed so that when stirring is stopped, the resultant crystals spreads all over the solvent.

The polymorphic crystals (B') can be obtained by still another preparation process described below: 7-methoxy-4-chloroquinoline-6-carboxamide and 1-(2-chloro-4-hydroxyphenyl)-3-cyclopropylurea are reacted in the presence of a base (for example, potassium t-butoxide, cesium carbonate, potassium carbonate, etc.) in an organic solvent that works a good solvent for 4-(3-chloro-4-(cyclopropylaminocarbonyl)aminophenoxy)-7-methoxy-6-quinolinecarboxamide (for example, DMSO, dimethylimidazolidinone, 1-methyl-2-pyrrolidinone, N,N-dimethylformamide, N,N-dimethylacetamide, sulfolane, etc.), and then thereto a poor solvent (for example, water, acetone, acetonitrile, ethyl acetate, isopropyl acetate, methanol, ethanol, n-propanol, isopropanol, or a mixture thereof, etc.) is admixed slowly (for example, for 30 min. or longer).

More specifically, for example, to a mixture of 1-(2-chloro-4-hydroxyphenyl)-3-cyclopropylurea, 7-methoxy-4-chloro-quinoline-6-carboxamide (one equivalent or more based on 1-(2-chloro-4-hydroxyphenyl)-3-cyclopropylurea), and potassium t-butoxide (one equivalent or more based on 1-(2-chloro-4-hydroxyphenyl)-3-cyclopropylurea), DMSO in a volume from 5 to 10 times based on 1-(2-chloro-4-hydroxyphenyl)-3-cyclopropylurea is added at room temperature, and then the mixture is heated to from 55 to 75° C. while stirring for 20 hr. or longer to allow the reaction to proceed. To this reaction mixture, while heating at from 60 to 65° C. and stirring, a poor solvent (33% acetone in water) in a volume 15 times based on 1-(2-chloro-4-hydroxyphenyl)-3-cyclopropylurea is introduced over 2 hr. or longer so that crystals can appear. The polymorphic crystals (B') can be obtained by stirring the resulting reaction mixture, in which the crystals appeared, while heating at 40° C. for 3 hr. or longer to collect the crystals by filtration.

The polymorphic crystals (B') can be obtained by still another preparation process described below: the polymorphic crystals (A') of 4-(3-chloro-4-(cyclopropylaminocarbonyl)aminophenoxy)-7-methoxy-6-quinolinecarboxamide having a diffraction peak at a diffraction angle (2θ±0.2°) of 15.75° in a powder X-ray diffraction is suspended and heated in a mixed solution of an organic solvent which is a good solvent for the above polymorphic crystals and a poor solvent for the above polymorphic crystals. It is preferred that the polymorphic crystals (A') used for this purpose also has diffraction peaks at diffraction angles (2θ±0.2°) of 9.98° and 11.01°.

The polymorphic crystals (B') can be obtained by still another preparation process described below: the polymorphic crystals (A') of 4-(3-chloro-4-(cyclopropylaminocarbonyl)aminophenoxy)-7-methoxy-6-quinolinecarboxamide having absorbance at a wavenumber of 3452.3±2.5 cm$^{-1}$ in an infrared absorption spectrum (potassium bromide) is suspended and heated in a mixed solution of a good solvent for the above polymorphic crystals and a poor solvent for the above polymorphic crystals. It is preferred that the polymorphic crystals (A') used for this purpose has absorbance at a wavenumber of 3452.3±2.5 cm$^{-1}$ (and also at 1712.2±1.0 cm$^{-1}$) in an infrared absorption spectrum (potassium bromide).

The crystals of hydrochloride or hydrobromide of 4-(3-chloro-4-(cyclopropylaminocarbonyl)aminophenoxy)-7-methoxy-6-quinolinecarboxamide; the crystals of p-toluenesulfonate or sulfate of the same; the crystals (A) of the same; the crystals (B) of the same; the crystals (C) of the same; the crystals of dimethyl sulfoxide solvate of methanesulfonate of the same; the crystals (F) of the same; the crystals (I) of the same; the crystals (α) of the same; the crystals (β) of the same; and the crystals of dimethyl sulfoxide solvate of ethanesulfonate of the same can be obtained by preparation processes described in the following paragraphs.

The crystals of hydrochloride or hydrobromide can be obtained by mixing the carboxamide and a solvent to dissolve the carboxamide therein, to which hydrochloric acid or hydrobromic acid is then added. More specifically, for example, the carboxamide and the solvent are mixed to dissolve the carboxamide therein by heating, and then thereto hydrochloric acid or hydrobromic acid is added followed by gradually cooling the resulting mixture to room temperature so that the crystals of hydrochloride or hydrobromide can be prepared. As a solvent, an alcohol such as methanol, ethanol, 1-propanol, and 2-propanol can be used, and ethanol is preferred. Further, water may be optionally added to the alcohol. There is no particular restriction on the amount of the solvent, but the solvent preferably from 10 to 30 times, more preferably 20 times, as much as the solute is used. As for the amount of hydrochloric acid or hydrobromic acid, from 1.0 to 1.5 equivalents, preferably 1.1 equivalents, based on the solute can be used. There is no particular restriction on the heating temperature, but the heating temperature is preferably from 60° C. to the reflux temperature, and more preferably the reflux temperature. For cooling, it may take from 10 min. to 24 hr. to cool down gradually from the heating temperature to room temperature.

The crystals of a p-toluenesulfonate or sulfate can be obtained by mixing the carboxamide, a solvent, and p-toluenesulfonic acid or sulfuric acid to dissolve the carboxamide therein. More specifically, for example, the carboxamide, the solvent, and p-toluenesulfonic acid or sulfuric acid are mixed to dissolve the carboxamide therein by heating followed by gradually cooling the resulting mixture to room temperature so that the crystals of p-toluenesulfonate or sulfate can be prepared. As a solvent, for example, dimethyl sulfoxide, N,N-dimethylformamide, N,N-dimethylacetamide, etc., can be used, and dimethyl sulfoxide is preferred. There is no particular restriction on the amount of the solvent, but the solvent preferably from 10 to 30 times, more preferably 20 times, as much as the solute is used. As for the amount of p-toluenesulfonic acid or sulfuric acid, from 1.0 to 1.5 equivalents, preferably 1.2 equivalents, based on the solute can be used. There is no particular restriction on the heating temperature, but the heating temperature is preferably from 60° C. to the reflux temperature, more preferably from 70 to 100° C., and still more preferably 80° C. For cooling, it may take from 10 min. to 24 hr. to cool down gradually from the heating temperature to room temperature.

The crystals (A) can be obtained by a preparation process comprising mixing 4-(3-chloro-4-(cyclopropylaminocarbonyl)aminophenoxy)-7-methoxy-6-quinolinecarboxamide, a solvent, and methanesulfonic acid to dissolve. More specifically, for example, the carboxamide, the solvent, and methanesulfonic acid are mixed to dissolve the carboxamide therein by heating followed by gradually cooling the resulting mixture to room temperature so that the crystals (A) of methanesulfonate can be prepared. As a solvent, for example, methanol, ethanol, 2-propanol, etc., can be used, and methanol is preferred. There is no particular restriction on the amount of the solvent, but the solvent preferably from 10 to 30 times, more preferably 20 times, as much as the solute is used. As for the amount of methanesulfonic acid, from 1.0 to 1.5 equivalents, preferably 1.2 equivalents, based on the solute can be used. There is no particular restriction on the heating temperature, but the heating temperature is preferably from 60° C. to the reflux temperature, and more preferably from 70 to 80° C. For cooling, it may take from 1 to 24 hr., preferably from 3 to 12 hr., to cool down gradually from the heating temperature to room temperature.

The crystals (A) can be also obtained by a preparation process comprising mixing 4-(3-chloro-4-(cyclopropylaminocarbonyl)aminophenoxy)-7-methoxy-6-quinolinecarboxamide, acetic acid, and methanesulfonic acid to dissolve. More specifically, for example, the carboxamide, acetic acid, and methanesulfonic acid are mixed to dissolve the carboxamide therein by heating, and then thereto a poor solvent is added followed by gradually cooling the resulting mixture to room temperature so that the crystals (A) of methanesulfonate can be prepared. Further, it is preferred to add the seed crystals (A) of methanesulfonate with the poor solvent. There is no particular restriction on the amount of acetic acid, but acetic acid preferably from 5 to 20 times, more preferably 10 times, as much as the solute is used. As for the amount of methanesulfonic acid, from 1.0 to 2.5 equivalents, preferably from 1.4 to 2.2 equivalents, based on the solute can be used. As a poor solvent, for example, methanol, ethanol, etc., can be used, and ethanol is preferred. There is no particular restriction on the amount of the poor solvent, but the poor solvent preferably from 10 to 30 times, more preferably 20 times, as much as the solute is used. Further, the poor solvent can be added at once, or divided into from 2 to 4 parts, preferably 2 parts, for addition. In such case, the amount ratio of the first addition and the second addition is from 1:1 to 3:1, and preferably 3:2. There is no particular restriction on the heating temperature, but the heating temperature is preferably from 50° C. to the reflux temperature, and more preferably 50° C. For cooling, it may take from 10 min. to 6 hr., preferably from 1 to 2 hr., to cool down gradually from the heating temperature to room temperature.

The crystals (B) can be obtained by a preparation process comprising drying (for example, by drying under aeration) the crystals (I) of acetic acid solvate of methanesulfonate of 4-(3-chloro-4-(cyclopropylaminocarbonyl)aminophenoxy)-7-methoxy-6-quinolinecarboxamide to remove acetic acid.

The crystals (C) can be obtained by a preparation process comprising heating crystals of dimethyl sulfoxide solvate of methanesulfonate of 4-(3-chloro-4-(cyclopropylaminocarbonyl)aminophenoxy)-7-methoxy-6-quinolinecarboxamide (and preferably cooling down gradually to room temperature). This preparation process can be conducted either in the presence of or in the absence of a solvent. When a solvent is used, as the solvent, for example, ethyl acetate, isopropyl acetate, n-butyl acetate, etc., can be used, and n-butyl acetate is preferred. There is no particular restriction on the heating temperature, but the heating temperature is preferably from 70° C. to the reflux temperature, and more preferably the reflux temperature.

The crystals (C) can be also obtained by a preparation process comprising mixing the crystals (I) of acetic acid solvate of methanesulfonate of 4-(3-chloro-4-(cyclopropylaminocarbonyl)aminophenoxy)-7-methoxy-6-quinolinecarboxamide and a solvent. In this preparation process, as a solvent, for example, an alcohol such as methanol, ethanol, and 2-propanol can be used, and ethanol is preferred. There is no particular restriction on the stirring temperature, but the stirring temperature is preferably from 20 to 60° C., and more preferably 40° C.

The crystals (C) can be still also obtained by a preparation process comprising mixing 4-(3-chloro-4-(cyclopropylaminocarbonyl)aminophenoxy)-7-methoxy-6-quinolinecarboxamide, acetic acid, and methanesulfonic acid to dissolve. More specifically, for example, the carboxamide, acetic acid, and methanesulfonic acid are mixed to dissolve the carboxamide therein by heating, and then thereto 2-propanol as a poor solvent is added followed by gradually cooling the resulting mixture to about 15° C. so that the crystals (C) of methanesulfonate can be prepared. Further, it is preferred to add the seed crystals (C) of methanesulfonate with the poor solvent and to add isopropyl acetate to accelerate the appearance of the crystals. There is no particular restriction on the amount of acetic acid, but acetic acid preferably from 5 to 10 times, more preferably from 7 to 8 times, as much as the solute is used. As for the amount of methanesulfonic acid, from 1.0 to 1.5 equivalents, preferably 1.2 equivalents, based on the solute can be used. There is no particular restriction on the amount of the poor solvent, but the poor solvent preferably from 2 to 10 times, more preferably from 4 to 5 times, as much as the solute is used. When isopropyl acetate is added, there is no particular restriction on the amount of isopropyl acetate, but isopropyl acetate preferably from 2 to 10 times, more preferably 5 times, as much as the solute is used. There is no particular restriction on the heating temperature, but the heating temperature is preferably 40° C. For cooling, it may take from 10 min. to 6 hr., preferably from 1 to 2 hr., to cool down gradually from the heating temperature to about 15° C.

In another preparation process wherein 4-(3-chloro-4-(cyclopropylaminocarbonyl)aminophenoxy)-7-methoxy-6-quinolinecarboxamide, acetic acid, and methanesulfonic acid are mixed to dissolve, the carboxamide, acetic acid, and methanesulfonic acid are mixed to dissolve the carboxamide therein at room temperature (or about 30° C.), and then thereto 2-propanol as a poor solvent is added followed by gradually cooling the resulting mixture to about 15° C. Resultant crystals are collected by filtration, and then the above crystals and a solvent are mixed and stirred so that the crystals (C) of methanesulfonate can be prepared. Further, it is preferred to add the seed crystals (C) of methanesulfonate with the poor solvent. There is no particular restriction on the amount of acetic acid, but acetic acid preferably from 5 to 20 times, more preferably 10 times, as much as the solute is used. As for the amount of methanesulfonic acid, from 1.0 to 2.5 equivalents, preferably from 1.8 to 2.2 equivalents, based on the solute can be used. There is no particular restriction on the amount of the poor solvent, but the poor solvent preferably from 10 to 30 times, more preferably 20 times, as much as the solute is used. For cooling, it may take from 10 min. to 4 hr., preferably from 30 min. to 2 hr., to cool down gradually from room temperature (or about 30° C.) to about 15° C. As a solvent to be mixed with the collected crystals, for example, an alcohol such as methanol, ethanol, and 2-propanol can be used, and ethanol is preferred.

In further still another process for preparing the crystals (C), the crystals (B) of methanesulfonate of 4-(3-chloro-4-(cyclopropylaminocarbonyl)aminophenoxy)-7-methoxy-6-quinolinecarboxamide is moisturized.

Crystals of dimethyl sulfoxide solvate of methanesulfonate can be obtained by mixing the carboxamide, dimethyl sulfoxide, and methanesulfonic acid to dissolve the carboxamide therein by heating, and then by adding thereto a poor solvent followed by cooling the resulting mixture to about 15° C. Further, it is preferred to add the seed crystals (A) of methanesulfonate with the poor solvent. There is no particular restriction on the amount of dimethyl sulfoxide, but dimethyl sulfoxide preferably from 5 to 20 times, more preferably from 8 to 10 times, as much as the solute is used. As for the amount of methanesulfonic acid, from 1.0 to 4.0 equivalents, preferably from 1.2 to 3.5 equivalents, based on the solute can be used. As a poor solvent, for example, ethyl acetate, isopropyl acetate, 1-propanol, 2-propanol, etc., can be used, and ethyl acetate and 2-propanol are preferred. There is no particular restriction on the amount of the poor solvent, but the poor solvent preferably from 10 to 30 times, more preferably 20 times, as much as the solute is used. Further, the poor solvent can be added at once, or divided into from 2 to 4 parts, preferably 2 parts, for addition. In such case, the amount ratio of the first addition and the second addition is from 1:1 to 1:5, and preferably 1:4. There is no particular restriction on the heating temperature, but the heating temperature is preferably from 50 to 100° C., and more preferably 60 to 80° C. For cooling, it may take from 10 min. to 6 hr., preferably from 1 to 2 hr., to cool down from the heating temperature to about 15° C.

The crystals (F) can be obtained by a preparation process comprising mixing 4-(3-chloro-4-(cyclopropylaminocarbonyl)aminophenoxy)-7-methoxy-6-quinolinecarboxamide, acetic acid, and methanesulfonic acid to dissolve. More specifically, for example, the carboxamide, acetic acid, and methanesulfonic acid are mixed to dissolve the carboxamide therein by heating, and then thereto a poor solvent is added followed by gradually cooling the resulting mixture to room temperature so that the crystals (F) of hydrate of methanesulfonate can be prepared. Further, it is preferred to add the seed crystals (A) of methanesulfonate with the poor solvent. There is no particular restriction on the amount of acetic acid, but acetic acid preferably from 5 to 20 times, more preferably 10 times, as much as the solute is used. As for the amount of methanesulfonic acid, from 1.0 to 2.0 equivalents, preferably from 1.3 to 1.6 equivalents, based on the solute can be used. As a poor solvent, for example, ethyl acetate and isopropyl acetate can be used, and ethyl acetate is preferred. There is no particular restriction on the amount of the poor solvent, but the poor solvent preferably from 10 to 30 times, more preferably 20 times, as much as the solute is used. Further, the poor solvent can be added at once, or divided into from 2 to 4 parts, preferably 2 parts, for addition. In such case, the amount ratio of the first addition and the second addition is from 1:1 to 1:5, and preferably 1:3. There is no particular restriction on the heating temperature, but the heating temperature is preferably from 40 to 60° C., and more preferably 50° C. For cooling, it may take from 10 min. to 6 hr., preferably from 2 to 4 hr., to cool down gradually from the heating temperature to room temperature.

The crystals (I) can be obtained by a preparation process comprising mixing 4-(3-chloro-4-(cyclopropylaminocarbonyl)aminophenoxy)-7-methoxy-6-quinolinecarboxamide, acetic acid, and methanesulfonic acid to dissolve. More specifically, for example, the carboxamide, acetic acid, and methanesulfonic acid are mixed to dissolve the carboxamide therein by heating, and then thereto a poor solvent is added followed by gradually cooling the resulting mixture to room temperature so that the crystals (I) of an acetic acid solvate of methanesulfonate can be prepared. Further, it is preferred to add the seed crystals (C) of methanesulfonate with the poor solvent and to add isopropyl acetate to accelerate the appearance of the crystals. There is no particular restriction on the amount of acetic acid, but acetic acid preferably from 5 to 10 times, more preferably from 7 to 8 times, as much as the solute is used. As for the amount of methanesulfonic acid, from 1.0 to 1.5 equivalents, preferably 1.2 equivalents, based on the solute can be used. As a poor solvent, for example, 1-propanol 1-butanol, tert-butanol, etc., can be used, and 1-propanol is preferred. There is no particular restriction on the amount of the poor solvent, but the poor solvent preferably from 5 to 20 times, more preferably from 8 to 10 times, as much as the solute is used. Further, the poor solvent can be added at once, or divided into from 2 to 4 parts, preferably 2 parts, for addition. In such case, the amount ratio of the first addition and the second addition is from 1:1 to 1:5, and preferably 1:3.5. When isopropyl acetate is added, there is no particular restriction on the amount of isopropyl acetate, but isopropyl acetate preferably from 2 to 10 times, more preferably 5 times, as much as the solute is used. There is no particular restriction on the heating temperature, but the heating temperature is preferably 40° C. For cooling, it may take from 10 min. to 6 hr., preferably from 1 to 2 hr., to cool down gradually from the heating temperature to room temperature.

The crystals (α) can be obtained by a preparation process comprising mixing 4-(3-chloro-4-(cyclopropylaminocarbonyl)aminophenoxy)-7-methoxy-6-quinolinecarboxamide, a solvent, and ethanesulfonic acid to dissolve. More specifically, for example, the carboxamide, the solvent, and ethanesulfonic acid are mixed to dissolve the carboxamide therein by heating, and then thereto a poor solvent is added followed by gradually cooling the resulting solution to room temperature so that the crystals (α) of ethanesulfonate can be prepared. As a solvent, for example, dimethyl sulfoxide, etc., can be used. There is no particular restriction on the amount of the solvent, but the solvent preferably from 5 to 20 times, more preferably 10 times, as much as the solute is used. As for the amount of ethanesulfonic acid, from 1.0 to 1.5 equivalents, preferably 1.2 equivalents, based on the solute can be used. As a poor solvent, for example, ethyl acetate, etc., can be used. There is no particular restriction on the amount of the poor solvent, but the poor solvent preferably from 5 to 20 times, more preferably 10 times, as much as the solute is used. There is no particular restriction on the heating temperature, but the heating temperature is preferably from 50 to 70° C., and more preferably 60° C. For cooling, it may take from 10 min. to 24 hr., preferably from 1 to 2 hr., to cool down gradually from the heating temperature to room temperature.

The crystals (β) can be obtained by a preparation process comprising mixing the crystals (α) of ethanesulfonate of 4-(3-chloro-4-(cyclopropylaminocarbonyl)aminophenoxy)-7-methoxy-6-quinolinecarboxamide and a solvent. As a solvent, for example, methanol, ethanol, 2-propanol, etc., can be used, and ethanol is preferred. There is no particular restriction on the amount of the solvent, but the solvent preferably from 5 to 20 times, more preferably 10 times, as much as the solute is used. There is no particular restriction on the amount of water, but water preferably from 1/10 to 1/2 times, more preferably 1/6 times, as much as ethanol is used.

The crystals (β) can be also obtained by a preparation process comprising mixing 4-(3-chloro-4-(cyclopropylaminocarbonyl)aminophenoxy)-7-methoxy-6-quinolinecarboxamide, acetic acid, and ethanesulfonic acid to dissolve. More specifically, for example, the carboxamide, acetic acid, and ethanesulfonic acid are mixed to dissolve the carboxamide therein by heating, and then thereto a poor solvent and water are added followed by cooling the resulting mixture to 0° C. so that the crystals (β) of a hydrate of ethanesulfonate can be prepared. Further, it is preferred to add the seed crystals (β) of ethanesulfonate with the poor solvent. There is no particular restriction on the amount of acetic acid, but acetic acid preferably from 2.5 to 10 times, more preferably 5 times, as much as the solute is used. As for the amount of ethanesulfonic acid, from 1.0 to 1.5 equivalents, preferably 1.2 equivalents, based on the solute can be used. As a poor solvent, for example, ethanol, 2-propanol, etc., can be used, and 2-propanol is preferred. There is no particular restriction on the amount of the poor solvent, but the poor solvent preferably from 10 to 40 times, more preferably 30 times, as much as the solute is used. Further, the poor solvent can be added at once, or divided into from 2 to 4 parts, preferably 2 parts, for addition. In such case, the amount ratio of the first addition and the second addition is from 1:1 to 1:5, and preferably from 1:1.5 to 1:2. There is no particular restriction on the amount of water, but water preferably from 1/10 to 1/30 times, more preferably 1/20 times, as much as the poor solvent is used. There is no particular restriction on the heating temperature, but the heating temperature is preferably from 50 to 70° C., and more preferably 60° C. For cooling, it may take from 10 min. to 6 hr., preferably from 2 to 4 hr., to cool down from the heating temperature to 0° C.

Crystals of dimethyl sulfoxide solvate of ethanesulfonate can be obtained by mixing the carboxamide, dimethyl sulfoxide, and ethanesulfonic acid to dissolve the carboxamide therein by heating, and then by adding a poor solvent thereto followed by cooling the resulting solution to 0° C. Further, it is preferred to add the seed crystals (β) of ethanesulfonate with the poor solvent. There is no particular restriction on the amount of dimethyl sulfoxide, but dimethyl sulfoxide preferably from 5 to 20 times, more preferably 10 times, as much as the solute is used. As for the amount of ethanesulfonic acid, from 1.0 to 1.5 equivalents, preferably 1.2 equivalents, based on the solute can be used. As a poor solvent, for example, ethyl acetate, etc., can be used. There is no particular restriction on the amount of the poor solvent, but the poor solvent preferably from 5 to 20 times, more preferably 10 times, as much as the solute is used. Further, the poor solvent can be added at once, or divided into from 2 to 4 parts, preferably 2 parts, for addition. In such case, the amount ratio of the first addition and the second addition is from 1:1 to 3:1, and preferably 3:2. There is no particular restriction on the heating temperature, but the heating temperature is preferably from 50 to 70° C., and more preferably 60° C. For cooling, it may take from 10 min. to 6 hr., preferably from 1 to 2 hr., to cool down from the heating temperature to 0° C.

(Pharmaceutical Composition)

The pharmaceutical composition in accordance with the present invention comprises: in addition to the active ingredient consisting of the compound represented by Formula (1), salt thereof, or solvate of the foregoing, as described above;

(i) a compound, a 5% (w/w) aqueous solution or suspension of which has a pH of 8 or more; and/or (ii) silicic acid, salt thereof, or solvate of the foregoing.

Further, the compound whose pH of a 5% (w/w) aqueous solution or suspension thereof is 8 or more contributes to the suppression of the decomposition of the active ingredient under humidified and heated storage conditions, and hence hereinafter is referred to as the "stabilizer." Moreover, silicic acid, salt thereof, or solvate of the foregoing contributes to the inhibition of the gelation of the pharmaceutical composition, and hence hereinafter is referred to as the "gelation inhibitor."

As the stabilizer, magnesium oxide, calcium oxide, sodium carbonate, disodium hydrogenphosphate, sodium citrate, dipotassium hydrogenphosphate, sodium acetate, sodium hydrogencarbonate, and sodium hydroxide are preferred. Of these, magnesium oxide and calcium oxide are particularly preferred in view of an increase in weight and coloration. The amount of the stabilizer to add to the pharmaceutical composition is preferably from 0.5 to 15, more preferably from 1 to 10, and most preferably from 1 to 5 mass parts based on 100 mass parts of the pharmaceutical composition.

As the gelation inhibitor, light anhydrous silicic acid, silicon dioxide hydrate, calcium silicate, magnesium silicate, magnesium aluminosilicate, magnesium aluminometasilicate, magnesium aluminum silicate, synthetic aluminum silicate, and hydrous silicic dioxide are preferred. Of these, light anhydrous silicic acid, silicon dioxide hydrate, and calcium silicate are more preferred, and light anhydrous silicic acid and silicon dioxide hydrate are most preferred. The amount of the gelation inhibitor to add to the pharmaceutical composition is preferably from 4 to 20, and more preferably from 8 to 20 mass parts based on 100 mass parts of the pharmaceutical composition.

In the pharmaceutical composition in accordance with the present invention, in addition to the active ingredient consisting of the compound represented by Formula (1), salt thereof, or solvate of the foregoing, the stabilizer, and the gelation inhibitor; additives such as a diluent, a binder, a lubricant, a disintegrant, a coloring agent, a flavoring agent, an emulsifier, a surfactant, a solubilizing agent, a suspending agent, an isotonizing agent, a buffer, a preservative, an antioxidant, a stabilizing agent, and an absorption promoter can be added thereto.

Examples of diluents include lactose, sucrose, glucose, cornstarch, mannitol, sorbitol, starch, alpha starch, dextrin, crystalline cellulose, light anhydrous silicic acid, aluminum silicate, calcium silicate, magnesium aluminometasilicate, calcium hydrogenphosphate, etc.

Examples of binders include polyvinyl alcohol, methylcellulose, ethylcellulose, gum Arabic, tragacanth, gelatin, shellac, hydroxypropylmethylcellulose, hydroxypropylcellulose, sodium carboxymethylcellulose, polyvinylpyrrolidone, Macrogol, etc.

Examples of lubricants include magnesium stearate, calcium stearate, sodium stearyl fumarate, talc, polyethylene glycol, colloidal silica, etc.

Examples of disintegrants include crystalline cellulose, agar, gelatin, calcium carbonate, sodium hydrogencarbonate, calcium citrate, dextrin, pectin, low-substituted hydroxypropylcellulose, carboxymethylcellulose, carboxymethylcellulose calcium, croscarmellose sodium, carboxymethyl starch, carboxymethyl starch sodium, carmellose, carmellose sodium, crospovidone, low-substituted carboxymethyl starch sodium, partially alpha starch, etc. The amount of the disintegrant to add to the pharmaceutical composition is preferably from 0.1 to 30, and more preferably from 1 to 20 mass parts based on 100 mass parts of the pharmaceutical composition.

As the disintegrant, low-substituted hydroxypropylcellulose, carboxymethyl starch sodium, carmellose sodium, carmellose calcium, croscarmellose sodium, crospovidone, and partially alpha starch are preferred. Low-substituted hydroxypropylcellulose, carmellose calcium, croscarmellose sodium, crospovidone, and partially alpha starch are more preferred. Croscarmellose sodium is most preferred.

Examples of coloring agents include iron sesquioxide, yellow iron sesquioxide, carmine, caramel, beta-carotene, titanium oxide, talc, riboflavin sodium phosphate, yellow aluminum lake, etc, which have been approved as additives for medicaments.

Flavoring agents include cocoa powder, menthol, aromatic powder, mentha oil, borneol, powdered cinnamon bark, etc.

Examples of emulsifiers or surfactants include stearyl triethanolamine, sodium lauryl sulfate, lauryl aminopropionic acid, lecithin, glycerin monostearate, sucrose fatty acid ester, glycerin fatty acid ester, etc.

Examples of solubilizers include polyethylene glycol, propylene glycol, benzyl benzoate, ethanol, cholesterol, triethanolamine, sodium carbonate, sodium citrate, Polysorbate 80, nicotinamide, etc.

Examples of suspending agents include, in addition to the above surfactants, hydrophilic polymers such as polyvinyl alcohol, polyvinylpyrrolidone, methylcellulose, hydroxymethylcellulose, hydroxyethylcellulose, and hydroxypropylcellulose.

Examples of isotonizing agent include glucose, sodium chloride, mannitol, sorbitol, etc.

Examples of buffers include buffer solutions of phosphate, acetate, carbonate, citrate, etc.

Examples of preservatives include methylparaben, propylparaben, chlorobutanol, benzyl alcohol, phenethyl alcohol, dehydroacetic acid, sorbic acid, etc.

Examples of antioxidants include sulfite, ascorbic acid, alpha-tocopherol, etc.

Further, the pharmaceutical composition can be formulated into oral preparations such as tablets, powders, granules, capsules, syrups, troches, and inhalants; external preparations such as suppositories, ointments, ophthalmic ointments, tapes, eye drops, nasal drops, ear drops, cataplasms, and lotions; or injections. Oral preparations are formulated by combining the above additives as desired. Moreover, optionally surface of these oral preparations may be coated.

External preparations are formulated by combining, among the above described additives, in particular, the diluent, the binder, the flavoring agent, the emulsifier, the surfactant, the solubilizer, the suspending agent, the isotonizing agent, the preservative, the antioxidant, the stabilizing agent, and the absorption promoter, as desired. Injections are formulated by combining, among the above described additives, in particular, the emulsifier, the surfactant, the solubilizer, the suspending agent, the isotonizing agent, the buffer, the preservative, the antioxidant, the stabilizing agent, and the absorption promoter, as desired.

The pharmaceutical composition in accordance with the present invention can be prepared by a well-known method. For example, to prepare tablets, a preparation process comprising steps of pre-mixing, granulating, drying, milling, main-mixing, compression, coating, and screening in this order can be applied. Either wet granulation (a non-aqueous system is preferred) or dry granulation may be employed.

In the pre-mixing step, a diluent and a binder are mixed, for example, in a 20 L super mixer. In the granulating step, to the resulting mixture, the active ingredient and an organic solvent such as ethanol are added, which are then granulated, for example, in a 20 L super mixer. In the drying step, the resulting granules are dried in a tray dryer, etc. The milling step is then conducted by a power mill, etc. To the milled granules, a disintegrant and a lubricant are added, and the main mixing step is conducted, for example, in a 10/20 L tumbler mixer, etc. Then, the compression step is conducted by a tablet press. Finally, the screening step is conducted to obtain the pharmaceutical composition (tablets).

Further, before the addition of a diluent and a binder in the pre-mixing step, another pre-mixing step wherein the active ingredient and the gelation inhibitor are added in advance can be performed. In such case, in the granulating step, only an organic solvent such as ethanol will be added. Moreover, between the coating step and the screening step, a mixing step in a 5 L tumbler mixer, etc., may be performed.

The dosage of the pharmaceutical composition in accordance with the invention depends on symptoms, age, and dosage forms, but in general, in terms of the active ingredient, from 100 µg to 10 g thereof is administered daily once or in a few divided portions to an adult.

The pharmaceutical composition in accordance with the present invention is extremely useful as an angiogenic inhibitor, and is effective as an agent to prevent or treat diseases against which angiogenic inhibition is effective, an angiogenic inhibitor, an anti-tumor agent, an agent to treat angioma, a cancer metastasis inhibitor, an agent to treat retinal angiogenesis, an agent to treat diabetic retinopathy, an agent to treat inflammatory diseases, an agent to treat inflammatory diseases selected from the group consisting of osteoarthritis, rheumatic arthritis, psoriasis, and delayed hyperactivity, and an agent to treat atherosclerosis.

Further, when the pharmaceutical composition in accordance with the present invention is used as an anti-tumor agent, the target tumor thereof is, for example, pancreatic cancer, stomach cancer, colorectal cancer, breast cancer, prostate cancer, lung cancer, renal cancer, brain tumor, blood cancer, or ovarian cancer. In particular, stomach cancer, colorectal cancer, prostate cancer, or renal cancer is a preferred target.

Moreover, the pharmaceutical composition in accordance with the present invention exhibits a potent c-Kit kinase inhibitory action, and hence is useful as an anti-tumor agent against tumors exacerbated by activated c-Kit kinase (acute myeloid leukemia, mast cell leukemia, small cell lung cancer, GIST, testicular tumor, ovarian cancer, breast cancer, brain tumor, neuroblastoma, and colorectal cancer). The pharmaceutical composition in accordance with the present invention is also useful as an agent to treat diseases such as mastocytosis in which the involvement of c-Kit kinase is suspected, allergies, and asthma.

EXAMPLES

The present invention is further explained in detail by referring to examples and comparative examples in the following paragraphs. However, the present invention shall not be limited by the following examples by any means.

[Preparation of Medicament (Active Ingredient)]

Preparation Example 1

Preparation (1) of 4-(3-chloro-4-(cyclopropylaminocarbonyl)aminophenoxy)-7-methoxy-6-quinolinecarboxamide Phenyl N-(4-(6-carbamoyl-7-methoxy-4-quinolyl)oxy-2-chlorophenyl)carbamate (17.5 g, 37.7 mmol) disclosed in WO 02/32872 was dissolved in N,N-dimethylformamide (350 mL), and then cyclopropylamine (6.53 mL, 94.25 mmol) was added to the reaction mixture under a nitrogen atmosphere, followed by stirring overnight at room temperature. To the mixture was added water (1.75 L), and the mixture was stirred. Precipitated crude crystals were collected by filtration, washed with water, and dried at 70° C. for 50 min. To the obtained crude crystals was added ethanol (300 mL), and then the mixture was heated under reflux for 30 min to dissolve, followed by stirring overnight to cool slowly down to room temperature. Precipitated crystals was collected by filtration and dried under vacuum, and then further dried at 70° C. for 8 hours to give the titled crystals (12.91 g; 80.2%).

Preparation Example 2

Preparation (2) of 4-(3-chloro-4-(cyclopropylaminocarbonyl)aminophenoxy)-7-methoxy-6-quinolinecarboxamide (1) Preparation of phenyl N-(2-chloro-4-hydroxyphenyl)carbamate

[Formula 3]

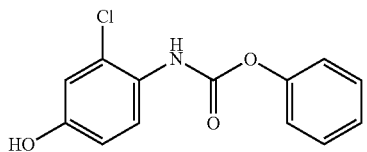

To a suspension of 4-amino-3-chlorophenol (23.7 g) in N,N-dimethylformamide (100 mL) was added pyridine (23.4 mL) while cooling in an ice bath, and phenyl chloroformate (23.2 mL) was added dropwise below 20° C. After stirring at room temperature for 30 min, water (400 mL), ethyl acetate (300 mL), and 6N-HCl (48 mL) were added and stirred. The organic layer was separated, washed twice with a 10% aqueous sodium chloride solution (200 mL), and dried over magnesium sulfate. The solvent was evaporated to give 46 g of the titled compound as a solid.

$^1$H-NMR Spectrum (CDCl$_3$) δ(ppm): 5.12 (1 h, br s), 6.75 (1H, dd, J=9.2, 2.8 Hz), 6.92 (1H, d, J=2.8 Hz), 7.18-7.28 (4H, m), 7.37-7.43 (2H, m), 7.94 (1H, br s)

(2) Preparation of 1-(2-chloro-4-hydroxyphenyl)-3-cyclopropylurea

[Formula 4]

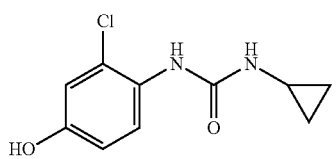

To a solution of phenyl N-(2-chloro-4-hydroxyphenyl)carbamate in N,N-dimethylformamide (100 mL) was added cyclopropylamine (22.7 mL) while cooling in an ice bath, and the stirring was continued at room temperature overnight. Water (400 mL), ethyl acetate (300 mL), and 6N-HCl (55 mL) were added thereto, and the mixture was stirred. The organic layer was then separated, washed twice with a 10% aqueous sodium chloride solution (200 mL), and dried over magnesium sulfate. The solvent was evaporated to give prism crystals, which were collected by filtration and washed with heptane to give 22.8 g of the titled compound (yield from 4-amino-3-chlorophenol: 77%).

$^1$H-NMR Spectrum (CDCl$_3$) δ(ppm): 0.72-0.77 (2H, m), 0.87-0.95 (2H, m), 2.60-2.65 (1H, m), 4.89 (1H, br s), 5.60 (1H, br s), 6.71 (1H, dd, J=8.8, 2.8 Hz), 6.88 (1H, d, J=2.8 Hz), 7.24-7.30 (1H, br s), 7.90 (1H, d, J=8.8 H)

(3) Preparation of 4-(3-chloro-4-(cyclopropylaminocarbonyl)aminophenoxy)-7-methoxy-6-quinolinecarboxamide To dimethyl sulfoxide (20 mL) were added 7-methoxy-4-chloroquinoline-6-carboxamide (0.983 g), 1-(2-chloro-4-hydroxyphenyl)-3-cyclopropylurea (1.13 g) and cesium carbonate (2.71 g), and the mixture was heated and stirred at 70° C. for 23 hours. The reaction mixture was cooled to room temperature, and water (50 mL) was added, and the resultant crystals were then collected by filtration to give 1.56 g of the titled compound (yield: 88%).

Preparation Example 3

Preparation (3) of 4-(3-chloro-4-(cyclopropylaminocarbonyl)aminophenoxy)-7-methoxy-6-quinolinecarboxamide 7-Methoxy-4-chloroquinoline-6-carboxamide (5.00 kg, 21.13 mol), dimethyl sulfoxide (55.05 kg), 1-(2-chloro-4-hydroxyphenyl)-3-cyclopropylurea (5.75 kg, 25.35 mol) and potassium t-butoxide (2.85 kg, 25.35 mol) were introduced in this order into a reaction vessel under a nitrogen atmosphere. The mixture was stirred for 30 min at 20° C., and the temperature was raised to 65° C. over 2.5 hours. The mixture was stirred at the same temperature for 19 hours. 33% (v/v) acetone-water (5.0 L) and water (10.0 L) were added dropwise over 3.5 hours. After the addition was completed, the mixture was stirred at 60° C. for 2 hours. 33% (v/v) acetone-water (20.0 L) and water (40.0 L) were added dropwise at 55° C. or more over 1 hour. After stirring at 40° C. for 16 hours, precipitated crystals were collected by filtration using a nitrogen pressure filter, and was washed with 33% (v/v) acetone-water (33.3 L), water (66.7 L), and acetone (50.0 L) in that order. The obtained crystals were dried at 60° C. for 22 hours using a conical vacuum dryer to give 7.78 kg of the titled compound (yield: 96.3%).

Further, all of the $^1$H-NMR chemical sift values of 4-(3-chloro-4-(cyclopropylaminocarbonyl)aminophenoxy)-7-methoxy-6-quinolinecarboxamide prepared in Preparation Examples 1 to 3 described above agreed with those of 4-(3-chloro-4-(cyclopropylaminocarbonyl)aminophenoxy)-7-methoxy-6-quinolinecarboxamide described in WO 02/32872.

[Stability Evaluation of Medicament]

The crystals (C) (hereinafter, referred to as the "medicament Y") of methanesulfonate of 4-(3-chloro-4-(cyclopropylaminocarbonyl)aminophenoxy)-7-methoxy-6-quinolinecarboxamide (the "medicament X") synthesized in the above "Preparation of Medicament (Active Ingredient)" was combined with the following 10 compounds (that exhibit various pH values when 5% (w/w) aqueous solutions or suspensions were made therewith. In the table, pH values thereof are shown). Stability of the medicament X therewith was evaluated.

TABLE 1

|  | pH value of 5% (w/w) aqueous solution or suspension |
|---|---|
| Magnesium oxide (MgO, Tomita Pharmaceutical Co., Ltd.) | 10.63 |
| Sodium carbonate (Na$_2$CO$_3$, Wako Pure Chemical Industries, Ltd.) | 11.45 |
| Disodium hydrogenphosphate (Na$_2$HPO$_4$, Kanto Chemical Co., Inc.) | 9.26 |
| Sodium citrate (Sodium citrate, Kozakai Pharmaceutical Co., Ltd.) | 8.22 |
| Dipotassium hydrogenphosphate (K$_2$HPO$_4$, Wako Pure Chemical Industries, Ltd.) | 9.11 |
| Sodium acetate (Sodium acetate, Wako Pure Chemical Industries, Ltd.) | 8.46 |
| Sodium hydrogencarbonate (NaHCO$_3$, Wako Pure Chemical Industries, Ltd.) | 8.15 |
| Sodium hydroxide (NaOH, Wako Pure Chemical Industries, Ltd.) | 13.56 |
| Glycine (Glycine, Ajinomoto Co., Inc.) | 6.17 |
| δ-Gluconolactone (δ-Gluconolactone, Kanto Chemical Co., Inc.) | 2.40 |

Anhydrous dibasic calcium phosphate (a diluent, from Kyowa Chemical Industry Co., Ltd.), croscarmellose sodium (a disintegrant, trade name: Ac-Di-Sol, from FMC International Inc.), hydroxypropylcellulose (a binder, trade name: HPC-L, from Nippon Soda Co., Ltd.), and the medicament Y are mixed in a ratio of 10/2.3/3/0.19 (w/w/w/w). To the resulting mixture, water was added, which then underwent the mixing/wet granulation process in a tablet mill followed by drying at 60° C. for 5 hr. to give the pellets.

Approximately 50 mg of each of stabilizers, magnesium oxide (MgO), sodium carbonate (Na$_2$CO$_3$), disodium hydrogenphosphate (Na$_2$HPO$_4$), sodium citrate, dipotassium hydrogenphosphate (K$_2$HPO$_4$), sodium acetate, sodium hydrogencarbonate (NaHCO$_3$), sodium hydroxide (NaOH), glycine, and δ-gluconolactone was combined together to grind in a mortar, with which approximately 500 mg of the above pellets were kneaded in a mortar. To the resulting mixture, 50 L of water was added and mixed further.

The prepared mixture was divided into about 100 mg in 2 PP tubes, which were then stressed for a week under the conditions of 60° C./open and under the conditions of 60° C./75% relative humidity/open (hereinafter, relative humidity is abbreviated as "RH", and "open" refers to conditions wherein an open tube is heated and humidified). To the stressed mixture, 8 mL of an extractant was added, which then underwent sonication. The resulting suspension was centrifuged to give the supernatant as a sample solution, which then was analyzed by HPLC. The results are shown in Table 2. In Table 2, the results from the one with no stabilizer are also shown.

TABLE 2

| Additive | 60° C./open, 1 week | | 60° C./75% RH/open, 1 week | |
|---|---|---|---|---|
|  | HPLC purity (%) | Decomposed product A (%) | HPLC purity (%) | Decomposed product A (%) |
| No additive | 97.0 | 0.40 | 95.6 | 1.63 |
| MgO | 97.4 | 0.08 | 97.2 | 0.06 |
| Na$_2$CO$_3$ | 97.6 | 0.06 | 97.3 | 0.12 |
| Na$_2$HPO$_4$ | 97.5 | 0.06 | 97.5 | 0.08 |
| δ-Gluconolactone | 97.9 | 0.10 | 95.6 | 1.88 |
| Sodium citrate | 97.6 | 0.10 | 97.6 | 0.09 |
| K$_2$HPO$_4$ | 97.4 | 0.06 | 97.4 | 0.08 |
| Sodium acetate | 97.6 | 0.08 | 97.4 | 0.21 |
| Glycine | 97.0 | 0.15 | 92.3 | 1.38 |
| NaHCO$_3$ | 97.5 | 0.11 | 97.3 | 0.10 |
| NaOH | 97.5 | 0.06 | 97.4 | 0.06 |

The relationship between the pH value of a 5% (w/w) aqueous solution or suspension of each stabilizer and the decomposed product A (see the chemical formula described above) is also shown in FIG. 1. These results demonstrate that when the pH value of a 5% (w/w) aqueous solution or suspension of the stabilizer is 8 or more, the decomposition can be significantly reduced.

[Preparation of Pharmaceutical Composition]

Example 1

10 mg Tablets: Containing Magnesium Oxide

In a 1 L super mixer 2.5 g of the medicament Y, 10 g of magnesium oxide (a stabilizer, from Tomita Pharmaceutical Co., Ltd.), 48.5 g of D-mannitol (a diluent, from Towa Chemical Industry Co., Ltd.), 10 g of partially alpha starch (a disintegrant, trade name: PCS (pharmaceutical grade), from Asahi Kasei Corporation), 22.5 g of crystalline cellulose (a diluent, trade name: Avicel PH101, from Asahi Kasei Corporation), and 3 g of hydroxypropylcellulose (a binder, trade name: HPC-L, from Nippon Soda Co., Ltd.) were mixed. Then thereto a suitable amount of purified water was added followed by granulation, drying, and milling to give the granules. To these granules, 3 g of croscarmellose sodium (a disintegrant, trade name: Ac-Di-Sol, from FMC International Inc.) and 0.5 g of magnesium stearate (a lubricant) were admixed, and then tablets were formed by a tablet press to give tablets (the total mass per tablet was 400 mg) containing 10 mg of the medicament Y per tablet.

Comparative Example 1

10 mg Tablets: Containing No Magnesium Oxide

In a 1 L super mixer 2.5 g of the medicament Y, 10 g of calcium hydrogenphosphate (a diluent), 48.5 g of D-mannitol (a diluent, from Towa Chemical Industry Co., Ltd.), 10 g of partially alpha starch (a disintegrant, trade name: PCS (pharmaceutical grade), from Asahi Kasei Corporation), 22.5 g of crystalline cellulose (a diluent, trade name: Avicel PH101, from Asahi Kasei Corporation), and 3 g of hydroxypropylcellulose (a binder, trade name: HPC-L, from Nippon Soda Co., Ltd.) were mixed. Then thereto a suitable amount of purified water was added followed by granulation, drying, and milling to give the granules. To these granules, 3 g of croscarmellose sodium (a disintegrant, trade name: Ac-Di-Sol, from FMC International Inc.) and 0.5 g of magnesium stearate (a lubricant) were admixed, and then tablets were formed by a tablet press to give tablets (the total mass per tablet was 400 mg) containing 10 mg of the medicament Y per tablet.

Stability was tested for the tablets prepared in Example 1 and Comparative Example 1. In the test, after the tablets were stored at 5° C., at 25° C., and at 40° C. and under relative humidity 75% RH, for 3 months each, impurity levels (%) were determined by HPLC. The results are shown in Table 3 below. As shown in Table 3, the tablets containing magnesium oxide (MgO) (Example 1) are superior in stability to the tablets containing no magnesium oxide (MgO) (Comparative Example 1). In particular, the stability under the humidified conditions was remarkably improved with the stabilizer.

TABLE 3

| Storage conditions | Example 1 | Comparative Example 1 |
| --- | --- | --- |
| 5° C./3 Months | 0 | 0 |
| 25° C./3 Months | 0 | 0.17 |
| 40° C. · 75% RH/3 Months | 0 | 1.58 | values: impurity levels (%) determined by HPLC

Further, the ability of decomposition suppression was examined for magnesium oxide, disodium hydrogenphosphate, sodium hydrogencarbonate, and sodium hydroxide.

A placebo tablet containing 8.0 mg of light anhydrous silicic acid (trade name: AEROSIL (registered trademark) 200, from Nippon Aerosil Co., Ltd.), 52.5 mg of D-mannitol (from Towa Chemical Industry Co., Ltd.), 30.0 mg of crystalline cellulose (trade name: Avicel PH101, from Asahi Kasei Corporation), 3.0 mg of hydroxypropylcellulose (trade name: HPC-L, from Nippon Soda Co., Ltd.), 5.0 mg of croscarmellose sodium (trade name: Ac-Di-Sol, from FMC International Inc.), 1.5 mg of sodium stearyl fumarate (from JRS Pharma LP), and 5.0 mg of opadry yellow was prepared according to an ordinary method. Approximately 30 g of the placebo tablets were ground in a tablet mill, to which then about 33 mg of the medicament Y was added. By repetitive mixing of the medicament Y with the ground placebo tablets, 1/1000 diluted powder (0.1%) was obtained.

Approximately 100 mg of each of stabilizers (magnesium oxide, disodium hydrogenphosphate, sodium hydrogencarbonate, and sodium hydroxide) was mixed with 1,900 mg of the 0.1% powder in a mortar to prepare a powder containing a 5% stabilizer. Likewise, a powder containing a 4, 3, 2, or 1% stabilizer was prepared.

Figure 6:
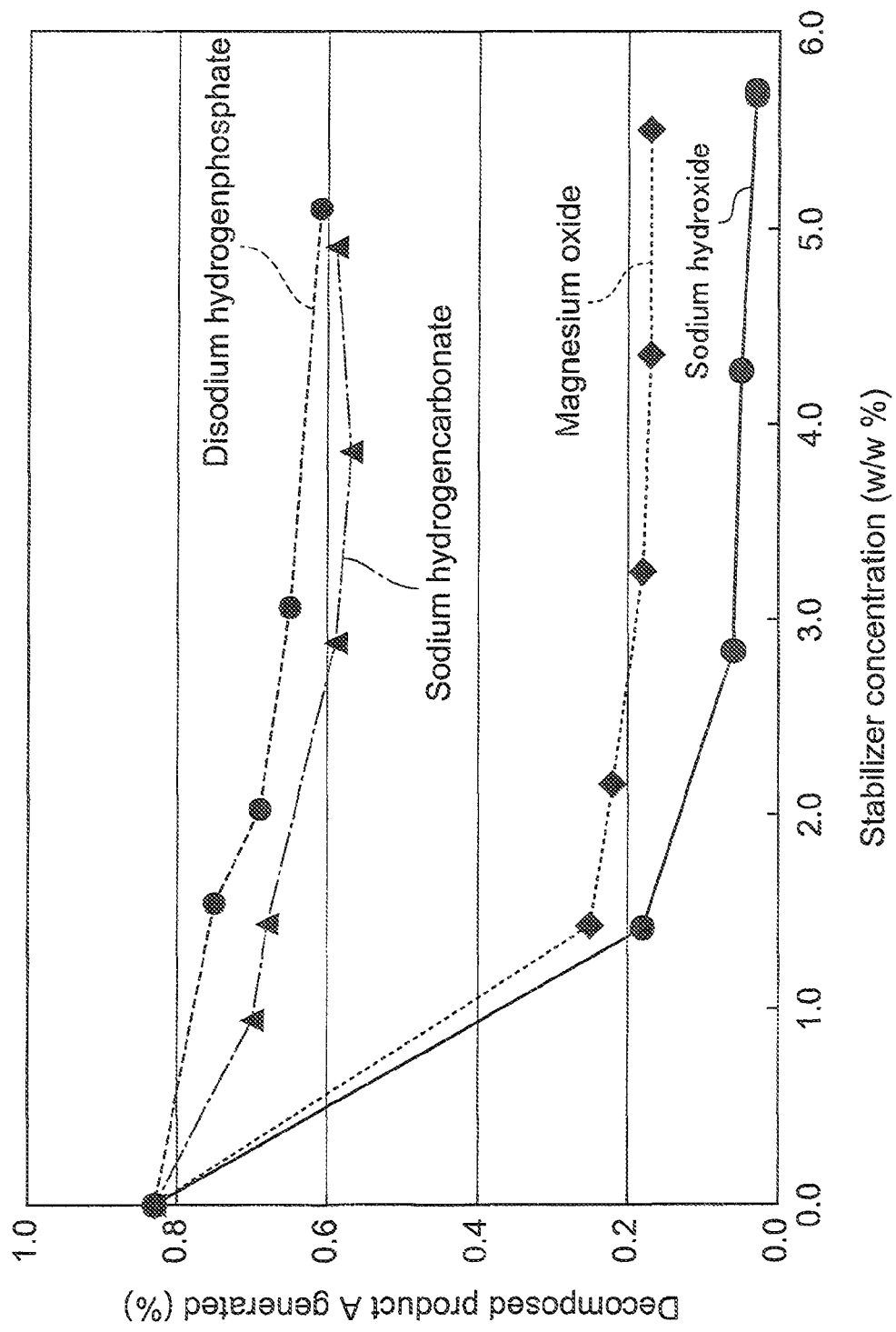
FIG. 6 is a graph illustrating the amount of the decomposed product A generated when various kinds of stabilizers were added at various concentrations.

In a glass vial, approximately 200 mg of each of the prepared mixtures (0.2 mg of the medicament X is contained) was stored and stressed under the conditions of 65° C./75% RH/open for a week. To the stressed mixture, 5 mL of an extractant was added, which then underwent sonication. The resulting suspension was centrifuged to give the supernatant as a sample solution, which then was analyzed by HPLC. The results are shown in FIG. 6. FIG. 6 is a graph illustrating the amount of the decomposed product A generated when various kinds of stabilizers were added at various concentrations. The results demonstrate that sodium hydroxide provided the highest stabilizing effect, the decomposition of the medicament X being reduced by adding only 1% of sodium hydroxide. Further, the stabilizing effect of magnesium oxide was similar to that of sodium hydroxide, the decomposition of the medicament X being significantly reduced by adding only 1% of magnesium oxide. The stabilizing effect of magnesium oxide was almost constant by adding 3% or more thereof.

[Inhibition of Gelation]

Example 2

1 mg Tablets

In a 20 L super mixer, 24 g of the medicament Y and 192 g of light anhydrous silicic acid (a gelation inhibitor, trade name: AEROSIL (registered trademark) 200, from Nippon Aerosil Co., Ltd.) were mixed, and thereto 1,236 g of D-mannitol (a diluent, from Towa Chemical Industry Co., Ltd.), 720 g of crystalline cellulose (a diluent, trade name: Avicel PH101, from Asahi Kasei Corporation), and 72 g of hydroxypropylcellulose (a binder, trade name: HPC-L, from Nippon Soda Co., Ltd.) were further added and mixed. A suitable amount of absolute ethanol was then added thereto to give the pellets containing the medicament Y. These pellets were dried in a tray dryer (at 60° C.), and then the size of the pellets was controlled in a power mill to give the granules. With these granules, 120 g of croscarmellose sodium (a disintegrant, trade name: Ac-Di-Sol, from FMC International Inc.) and 36 g of sodium stearyl fumarate (a lubricant, from JRS Pharma LP) were mixed in a 20 L tumbler mixer, and tablets were formed by a tablet press to give the tablets, the total mass per tablet of which was 100 mg. Further, the tablets were coated with a 10% aqueous solution of opadry yellow (OPADRY03F42069 YELLOW, from Colorcon (Japan) Limited) by a tablet coating machine to give the coated tablets, the total mass per tablet of which was 105 mg.

Example 3

10 mg Tablets

In a 20 L super mixer, 60 g of the medicament Y and 192 g of light anhydrous silicic acid (a gelation inhibitor, trade name: AEROSIL (registered trademark) 200, from Nippon Aerosil Co., Ltd.) were mixed, and thereto 1,200 g of D-mannitol (a diluent, from Towa Chemical Industry Co., Ltd.), 720 g of crystalline cellulose (a diluent, trade name: Avicel PH101, from Asahi Kasei Corporation), and 72 g of hydroxypropylcellulose (a binder, trade name: HPC-L, from Nippon Soda Co., Ltd.) were further added and mixed. A suitable amount of absolute ethanol was then added thereto to give the pellets containing the medicament Y. These pellets were dried in a tray dryer (at 60° C.), and then the size of the pellets was controlled in a power mill to give the granules. With these granules, 120 g of croscarmellose sodium (a disintegrant, trade name: Ac-Di-Sol, from FMC International Inc.) and 36 g of sodium stearyl fumarate (a lubricant, from JRS Pharma LP) were mixed in a 20 L tumbler mixer, and tablets were formed by a tablet press to give the tablets, the total mass per tablet of which was 400 mg. Further, the tablets were coated with a 10% aqueous solution of opadry yellow (OPADRY03F42069 YELLOW, from Colorcon (Japan) Limited) by a tablet coating machine to give the coated tablets, the total mass per tablet of which was 411 mg.

Example 4

100 mg Tablets

In a 1 L super mixer, 31.4 g of the medicament Y and 4 g of light anhydrous silicic acid (a gelation inhibitor, trade name: AEROSIL (registered trademark) 200, from Nippon Aerosil Co., Ltd.) were mixed, and thereto 40.1 g of anhydrous dibasic calcium phosphate (a diluent, from Kyowa Chemical Industry Co., Ltd.), 10 g of low-substituted hydroxypropylcellulose (a binder, trade name: L-HPC (LH-21), from Shin-Etsu Chemical Co., Ltd.), and 3 g of hydroxypropylcellulose (a binder, trade name: HPC-L, from Nippon Soda Co., Ltd.) were further added and mixed. A suitable amount of absolute ethanol was then added thereto to give the pellets containing the medicament Y. These pellets were dried in a tray dryer (at 60° C.), and then the size of the pellets was controlled in a power mill to give the granules. With these granules, 10 g of croscarmellose sodium (a disintegrant, trade name: Ac-Di-Sol, from FMC International Inc.) and 1.5 g of sodium stearyl fumarate (a lubricant, from JRS Pharma LP) were mixed, and tablets were formed by a tablet press to give the tablets, the total mass per tablet of which was 400 mg.

Comparative Example 2

100 mg Tablets

In a 1 L super mixer, 31.4 g of the medicament Y, 44.1 g of anhydrous dibasic calcium phosphate (a diluent, from Kyowa Chemical Industry Co., Ltd.), 10 g of low-substituted hydroxypropylcellulose (a binder, trade name: L-HPC (LH-21), from Shin-Etsu Chemical Co., Ltd.), and 3 g of hydroxypropylcellulose (a binder, trade name: HPC-L, from Nippon Soda Co., Ltd.) were mixed. A suitable amount of absolute ethanol was then added thereto to give the pellets containing the medicament Y. These pellets were dried in a tray dryer (at 60° C.), and then the size of the pellets was controlled in a power mill to give the granules. With these granules, 10 g of croscarmellose sodium (a disintegrant, trade name: Ac-Di-Sol, from FMC International Inc.) and 1.5 g of sodium stearyl fumarate (a lubricant, from JRS Pharma LP) were mixed in a tumbler mixer, and tablets were formed by a tablet press to give the tablets, the total mass per tablet of which was 400 mg.

Example 5

100 mg Tablets: 8% of Light Anhydrous Silicic Acid

In a 1 L super mixer, 31.4 g of the medicament Y and 8 g of light anhydrous silicic acid (a gelation inhibitor, trade name: AEROSIL (registered trademark) 200, from Nippon Aerosil Co., Ltd.) were mixed, and thereto 42.1 g of anhydrous dibasic calcium phosphate (a diluent, from Kyowa Chemical Industry Co., Ltd.), and 10 g of low-substituted hydroxypropylcellulose (a binder, trade name: L-HPC (LH-21), from Shin-Etsu Chemical Co., Ltd.) were further added and mixed. A suitable amount of absolute ethanol with 2 g of hydroxypropylcellulose (a binder, trade name: HPC-L, from Nippon Soda Co., Ltd.) suspended therein was then added thereto to give the pellets containing the medicament of the present invention. These pellets were dried in a tray dryer (at 60° C.), and then the size of the pellets was controlled in a power mill to give the granules. With these granules, 5 g of croscarmellose sodium (a disintegrant, trade name: Ac-Di-Sol, from FMC International Inc.) and 1.5 g of sodium stearyl fumarate (a lubricant, from JRS Pharma LP) were mixed, and tablets were formed by a tablet press to give the tablets, the total mass per tablet of which was 400 mg.

Example 6

100 mg Tablets: 6% of Light Anhydrous Silicic Acid

In a 1 L super mixer, 31.4 g of the medicament Y and 6 g of light anhydrous silicic acid (a gelation inhibitor, trade name: AEROSIL (registered trademark) 200, from Nippon Aerosil Co., Ltd.) were mixed, and thereto 44.1 g of anhydrous dibasic calcium phosphate (a diluent, from Kyowa Chemical Industry Co., Ltd.), and 10 g of low-substituted hydroxypropylcellulose (a binder, trade name: L-HPC (LH-21), from Shin-Etsu Chemical Co., Ltd.) were further added and mixed. A suitable amount of absolute ethanol with 2 g of hydroxypropylcellulose (a binder, trade name: HPC-L, from Nippon Soda Co., Ltd.) suspended therein was then added thereto to give the pellets containing the medicament of the present invention. These pellets were dried in a tray dryer (at 60° C.), and then the size of the pellets was controlled in a power mill to give the granules. With these granules, 5 g of croscarmellose sodium (a disintegrant, trade name: Ac-Di-Sol, from FMC International Inc.) and 1.5 g of sodium stearyl fumarate (a lubricant, from JRS Pharma LP) were mixed, and tablets were formed by a tablet press to give the tablets, the total mass per tablet of which was 400 mg.

Example 7

100 mg Tablets: 4% of Light Anhydrous Silicic Acid

In a 1 L super mixer, 31.4 g of the medicament Y and 4 g of light anhydrous silicic acid (a gelation inhibitor, trade name: AEROSIL (registered trademark) 200, from Nippon Aerosil Co., Ltd.) were mixed, and thereto 46.1 g of anhydrous dibasic calcium phosphate (a diluent, from Kyowa Chemical Industry Co., Ltd.), and 10 g of low-substituted hydroxypropylcellulose (a binder, trade name: L-HPC (LH-21), from Shin-Etsu Chemical Co., Ltd.) were further added and mixed. A suitable amount of absolute ethanol with 2 g of hydroxypropylcellulose (a binder, trade name: HPC-L, from Nippon Soda Co., Ltd.) suspended therein was then added thereto to give the pellets containing the medicament of the present invention. These pellets were dried in a tray dryer (at 60° C.), and then the size of the pellets was controlled in a power mill to give the granules. With these granules, 5 g of croscarmellose sodium (a disintegrant, trade name: Ac-Di-Sol, from FMC International Inc.) and 1.5 g of sodium stearyl fumarate (a lubricant, from JRS Pharma LP) were mixed, and tablets were formed by a tablet press to give the tablets, the total mass per tablet of which was 400 mg.

The storage test and the dissolution test were conducted for the tablets prepared above according to the methods described below.

(Storage Test)

Tablets in a glass bottle with the cap open were stored at 5° C., at 60° C. and 75% RH, at 40° C. and 75% RH, or at 30° C. and 65% RH.

(Dissolution Test)

The dissolution test was conducted according to the Japanese Pharmacopoeia 14th Edition and by the paddle method under the conditions described below. The test solution: 900 mL of 0.1 mol/L hydrochloric acid. The rotation speeds: 50 rpm. The temperature of the test solution: 37° C.

Experimental Example 1

Figure 2:
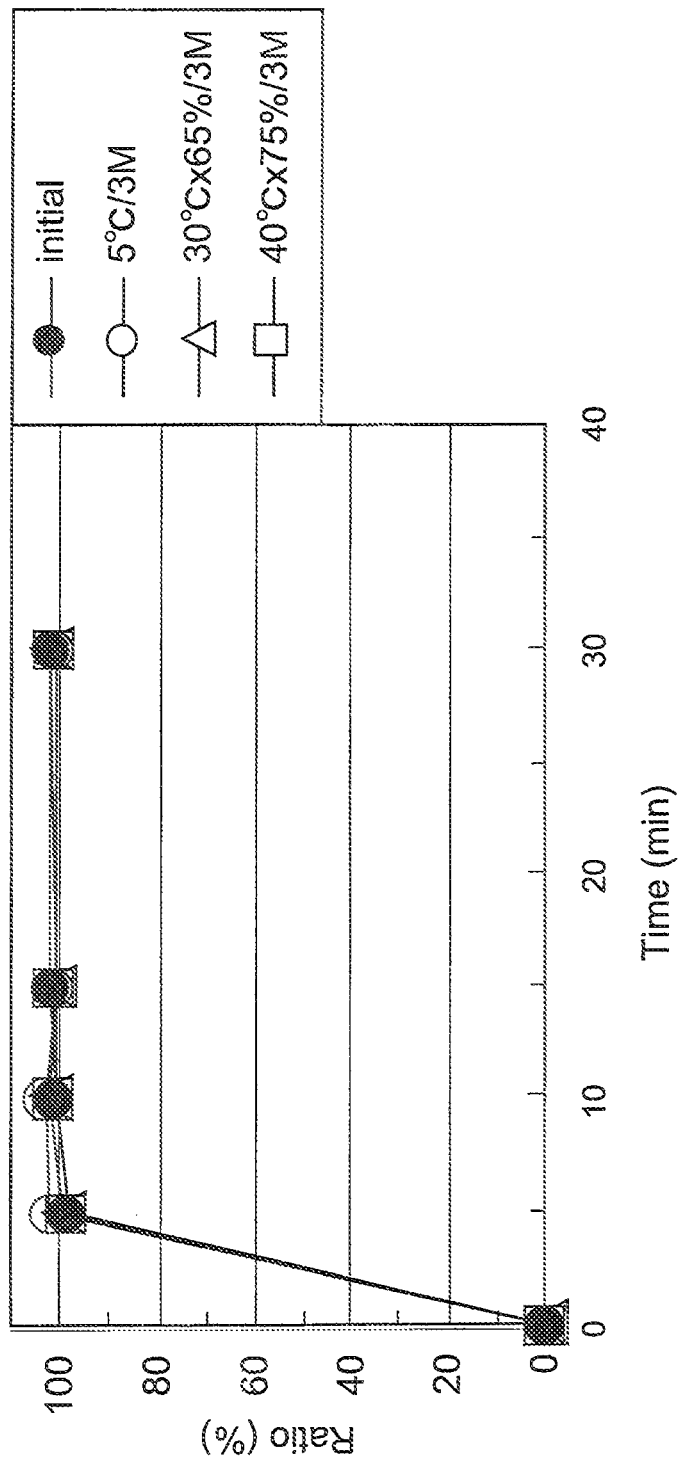
FIG. 2 illustrates the dissolution test results for the Example 2.
Figure 3:
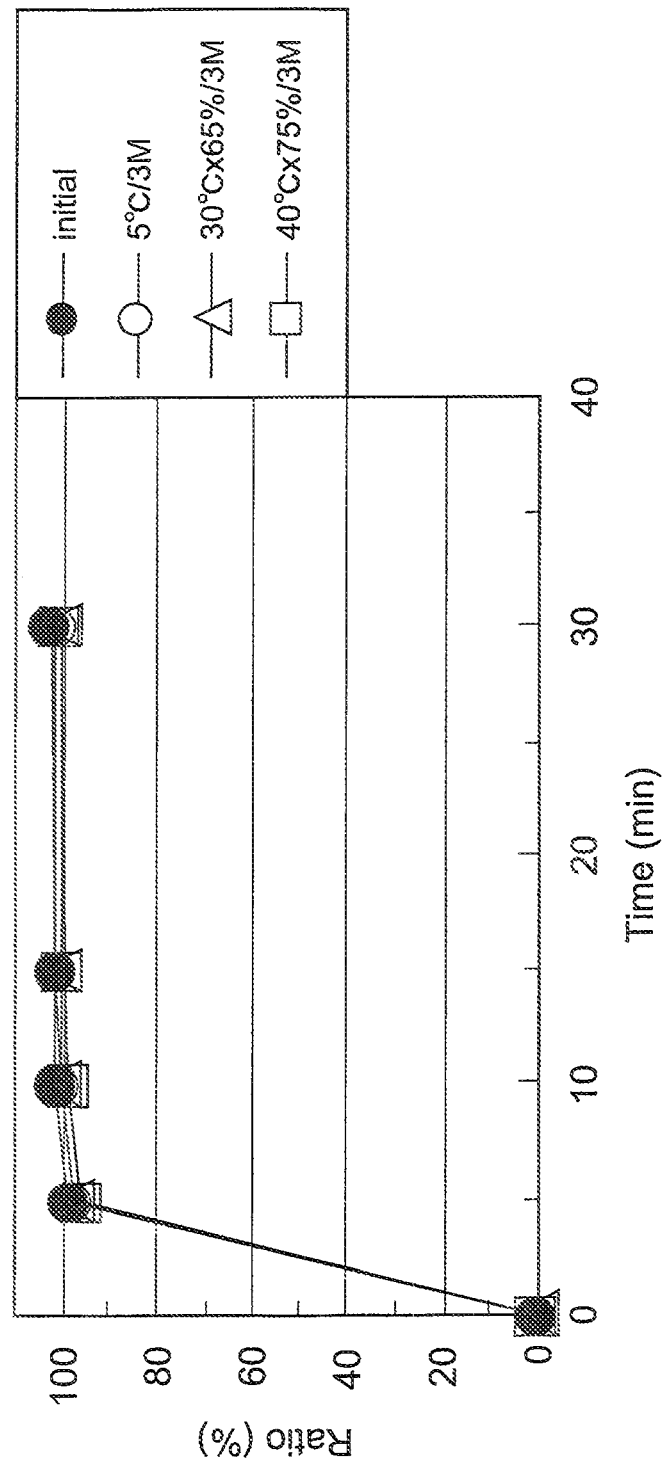
FIG. 3 illustrates the dissolution test results for the Example 3.

The storage test (the storage duration was 3 months) was conducted for the tablets prepared in Examples 2 and 3. No delayed dissolution was found for the tablets of both Examples at any of the conditions at 5° C., at 30° C. and 65% RH, and at 40° C. and 75% RH. The results of each of the examples are shown in FIGS. 2 and 3.

Experimental Example 2

Figure 4:
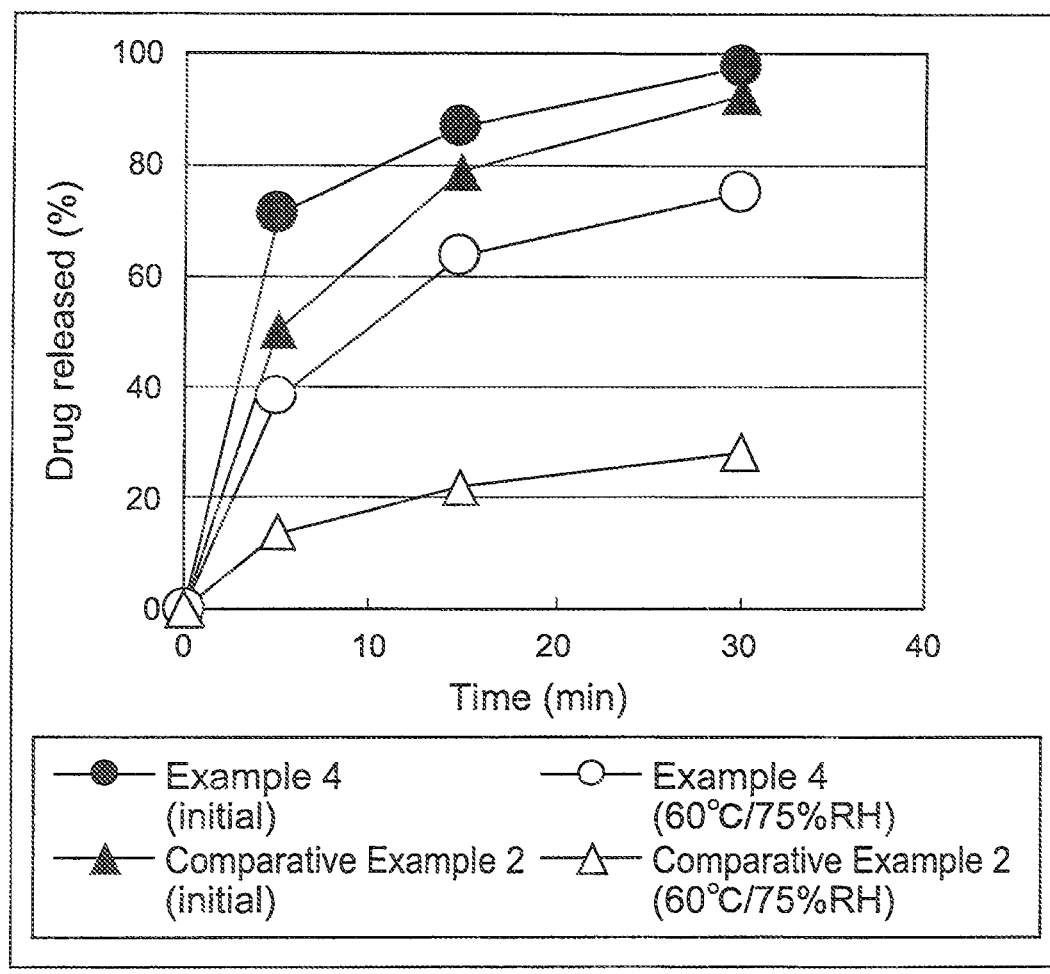
FIG. 4 illustrates the dissolution test results for the Example 4 and for the Comparative Example 2.

The tablets prepared in Example 4 and Comparative Example 2 were stored at 60° C. and 75% RH for 7 days. The tablets then underwent the dissolution test. The results are shown in FIG. 4. For the tablets of Comparative Example 2, the gelation of the tablet surface was noted even at the beginning of the test. Further, significant delayed dissolution was observed after the storage test. On the other hand, for the tablets of Example 4, the gelation on the surface was not noted on any of the tablets. The inhibition of delayed dissolution after the storage was also observed.

Experimental Example 3

Figure 5:
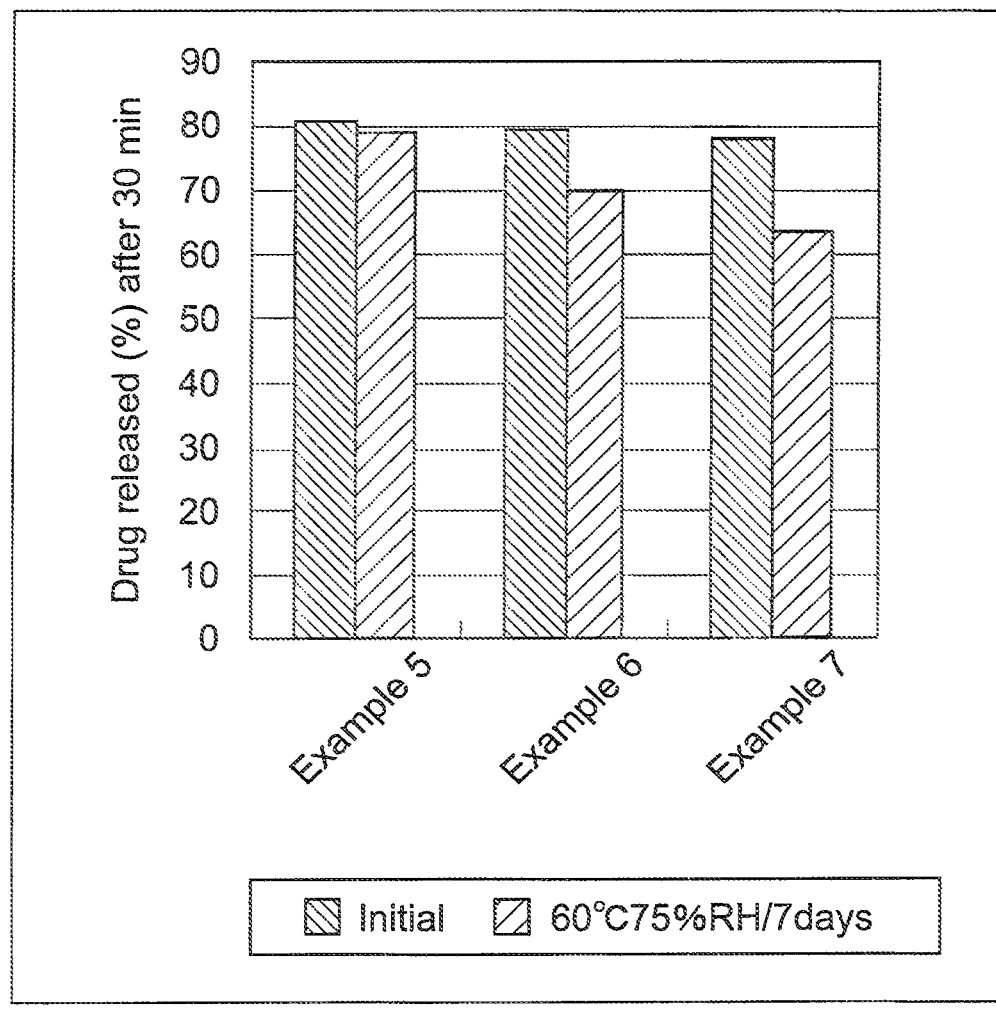
FIG. 5 illustrates the dissolution test results for the Examples 5, 6 and 7.

The tablets prepared in Examples 5 to 7 were stored at 60° C. and 75% RH for 7 days. The tablets then underwent the dissolution test. To confirm the influence of the amount of light anhydrous silicic acid contained in the tablet, the drug released (%) 30 min. after the dissolution test started was compared. The results are shown in FIG. 5. When from 16 to 32 mg of light anhydrous silicic acid was contained per 100 mg of the medicament Y, delayed dissolution seen in Comparative Example 2 was not observed. In particular, for the tablets of Example 5, wherein 32 mg of light anhydrous silicic acid was contained, delayed dissolution was barely seen after the storage as well.

The results shown above demonstrate that the addition of from 4 to 8% of the gelation inhibitor provides the pharmaceutical composition comprising the medicament X with great dissolution properties, while the gelation was effectively inhibited. Next examined were disintegration properties when higher levels of the gelation inhibitor was contained in the pharmaceutical composition. Disintegration properties when the stabilizer and the gelation inhibitor were contained therein were also examined. Disintegration properties were further examined, when silicone dioxide hydrate or calcium silicate was used in place of light anhydrous silicic acid as a gelation inhibitor.

Comparative Example 3

25 mg Tablets

To 7.85 g of the medicament Y, 22.4 g of D-mannitol (a diluent, from Towa Chemical Industry Co., Ltd.), 15.0 g of crystalline cellulose (a diluent, trade name: Avicel PH101, from Asahi Kasei Corporation), and 1.5 g of hydroxypropylcellulose (a binder, trade name: HPC-L, from Nippon Soda Co., Ltd.) were added and mixed. A suitable amount of absolute ethanol was then added thereto to give the pellets containing the medicament Y. These pellets were dried in a tray dryer (at 60° C.), and then the size of the pellets was controlled in a small speed mill to give the granules. With these granules, 2.5 g of croscarmellose sodium (a disintegrant, trade name: Ac-Di-Sol, from FMC International Inc.) and 0.8 g of sodium stearyl fumarate (a lubricant, from JRS Pharma LP) were mixed, and tablets were formed by a tablet press to give the tablets, the total mass per tablet of which was 200 mg.

Example 8

25 mg Tablets: 12% of Light Anhydrous Silicic Acid

In a 1 L super mixer, 7.85 g of the medicament Y and 6 g of light anhydrous silicic acid (a gelation inhibitor, trade name: AEROSIL (registered trademark) 200, from Nippon Aerosil Co., Ltd.) were mixed, and thereto 16.4 g of D-mannitol (a diluent, from Towa Chemical Industry Co., Ltd.), 15.0 g of crystalline cellulose (a diluent, trade name: Avicel PH101, from Asahi Kasei Corporation), and 1.5 g of hydroxypropylcellulose (a binder, trade name: HPC-L, from Nippon Soda Co., Ltd.) were further added and mixed. A suitable amount of absolute ethanol was then added thereto to give the pellets containing the medicament Y. These pellets were dried in a tray dryer (at 60° C.), and then the size of the pellets was controlled in a small speed mill to give the granules. With these granules, 2.5 g of croscarmellose sodium (a disintegrant, trade name: Ac-Di-Sol, from FMC International Inc.) and 0.8 g of sodium stearyl fumarate (a lubricant, from JRS Pharma LP) were mixed, and tablets were formed by a tablet press to give the tablets, the total mass per tablet of which was 200 mg.

Example 9

25 mg Tablets: 20% of Light Anhydrous Silicic Acid

In a 1 L super mixer, 7.85 g of the medicament Y and 10 g of light anhydrous silicic acid (a gelation inhibitor, trade name: AEROSIL (registered trademark) 200, from Nippon Aerosil Co., Ltd.) were mixed, and thereto 12.4 g of D-mannitol (a diluent, from Towa Chemical Industry Co., Ltd.), 15.0 g of crystalline cellulose (a diluent, trade name: Avicel PH101, from Asahi Kasei Corporation), and 1.5 g of hydroxypropylcellulose (a binder, trade name: HPC-L, from Nippon Soda Co., Ltd.) were further added and mixed. A suitable amount of absolute ethanol was then added thereto to give the pellets containing the medicament Y. These pellets were dried in a tray dryer (at 60° C.), and then the size of the pellets was controlled in a small speed mill to give the granules. With these granules, 2.5 g of croscarmellose sodium (a disintegrant, trade name: Ac-Di-Sol, from FMC International Inc.) and 0.8 g of sodium stearyl fumarate (a lubricant, from JRS Pharma LP) were mixed, and tablets were formed by a tablet press to give the tablets, the total mass per tablet of which was 200 mg.

Example 10

25 mg Tablets: 8% of Light Anhydrous Silicic Acid and 3% Magnesium Oxide

In a 1 L super mixer, 15.7 g of the medicament Y and 8 g of light anhydrous silicic acid (a gelation inhibitor, trade name: AEROSIL (registered trademark) 200, from Nippon Aerosil Co., Ltd.) were mixed, and thereto 3 g of magnesium oxide (a stabilizer, from Tomita Pharmaceutical Co., Ltd.), 33.8 g of D-mannitol (a diluent, from Towa Chemical Industry Co., Ltd.), 30 g of crystalline cellulose (a diluent, trade name: Avicel PH101, from Asahi Kasei Corporation), and 3 g of hydroxypropylcellulose (a binder, trade name: HPC-L, from Nippon Soda Co., Ltd.) were further added and mixed. A suitable amount of absolute ethanol was then added thereto to give the pellets containing the medicament Y. These pellets were dried in a tray dryer (at 60° C.), and then the size of the pellets was controlled in a small speed mill to give the granules. With these granules, 5 g of croscarmellose sodium (a disintegrant, trade name: Ac-Di-Sol, from FMC International Inc.) and 1.5 g of sodium stearyl fumarate (a lubricant, from JRS Pharma LP) were mixed, and tablets were formed by a tablet press to give the tablets, the total mass per tablet of which was 200 mg.

Example 11

25 mg Tablets: 8% of Light Anhydrous Silicic Acid and 5% Disodium Hydrogenphosphate In a 1 L super mixer, 7.85 g of the medicament Y and 4 g of light anhydrous silicic acid (a gelation inhibitor, trade name: AEROSIL (registered trademark) 200, from Nippon Aerosil Co., Ltd.) were mixed, and thereto 2.5 g of disodium hydrogenphosphate (a stabilizer, from Kanto Chemical Co., Inc.), 15.9 g of D-mannitol (a diluent, from Towa Chemical Industry Co., Ltd.), 15 g of crystalline cellulose (a diluent, trade name: Avicel PH101, from Asahi Kasei Corporation), and 1.5 g of hydroxypropylcellulose (a binder, trade name: HPC-L, from Nippon Soda Co., Ltd.) were further added and mixed. A suitable amount of absolute ethanol was then added thereto to give the pellets containing the medicament Y. These pellets were dried in a tray dryer (at 60° C.), and then the size of the pellets was controlled in a small speed mill to give the granules. With these granules, 2.5 g of croscarmellose sodium (a disintegrant, trade name: Ac-Di-Sol, from FMC International Inc.) and 0.8 g of sodium stearyl fumarate (a lubricant, from JRS Pharma LP) were mixed, and tablets were formed by a tablet press to give the tablets, the total mass per tablet of which was 200 mg.

Example 12

25 mg Tablets: 8% of Silicon Dioxide Hydrate

In a 1 L super mixer, 7.85 g of the medicament Y and 4 g of silicon dioxide hydrate (a gelation inhibitor, trade name: Sylysia, from Fuji Silysia Chemical Ltd.) were mixed, and thereto 18.4 g of D-mannitol (a diluent, from Towa Chemical Industry Co., Ltd.), 15.0 g of crystalline cellulose (a diluent, trade name: Avicel PH101, from Asahi Kasei Corporation), and 1.5 g of hydroxypropylcellulose (a binder, trade name: HPC-L, from Nippon Soda Co., Ltd.) were further added and mixed. A suitable amount of absolute ethanol was then added thereto to give the pellets containing the medicament Y. These pellets were dried in a tray dryer (at 60° C.), and then the size of the pellets was controlled in a small speed mill to give the granules. With these granules, 2.5 g of croscarmellose sodium (a disintegrant, trade name: Ac-Di-Sol, from FMC International Inc.) and 0.8 g of sodium stearyl fumarate (a lubricant, from JRS Pharma LP) were mixed, and tablets were formed by a tablet press to give the tablets, the total mass per tablet of which was 200 mg.

Example 13

25 mg Tablets: 8% of Calcium Silicate

In a 1 L super mixer, 7.85 g of the medicament Y and 4 g of calcium silicate (a gelation inhibitor, trade name: Florite (registered trademark), from Tokuyama Corp.) were mixed, and thereto 18.4 g of D-mannitol (a diluent, from Towa Chemical Industry Co., Ltd.), 15.0 g of crystalline cellulose (a diluent, trade name: Avicel PH101, from Asahi Kasei Corporation), and 1.5 g of hydroxypropylcellulose (a binder, trade name: HPC-L, from Nippon Soda Co., Ltd.) were further added and mixed. A suitable amount of absolute ethanol was then added thereto to give the pellets containing the medicament Y. These pellets were dried in a tray dryer (at 60° C.), and then the size of the pellets was controlled in a small speed mill to give the granules. With these granules, 2.5 g of croscarmellose sodium (a disintegrant, trade name: Ac-Di-Sol, from FMC International Inc.) and 0.8 g of sodium stearyl fumarate (a lubricant, from JRS Pharma LP) were mixed, and tablets were formed by a tablet press to give the tablets, the total mass per tablet of which was 200 mg.

The disintegration test was conducted for the tablets prepared above by the method described in the Japanese Pharmacopoeia 14th Edition. The disintegration time is summarized in Table 4.

TABLE 4

| Sample | Disintegration time |
| --- | --- |
| Comparative Example 3 | 15 min. or longer |
| Example 8 | 1.2 to 1.4 min. |
| Example 9 | 0.9 to 1.1 min. |
| Example 10 | 3.9 to 4.1 min. |
| Example 11 | 2.9 to 3.1 min. |
| Example 12 | 7.6 to 8.2 min. |
| Example 13 | 2.3 to 2.5 min. |

The tablets of any of Examples 8 to 13 had a shorter disintegration time than those from Comparative Example 3. It is shown that disintegration properties of the tablets prepared in Examples 8 to 13 were superior. The above demonstration confirms that the pharmaceutical composition of the present invention inhibits the gelation effectively.

Formulation Examples

Formulation examples comprising the crystals (C) of methanesulfonate of 4-(3-chloro-4-(cyclopropylaminocarbonyl)aminophenoxy)-7-methoxy-6-quinolinecarboxamide (the medicament X) synthesized in the above "Preparation of Medicament (Active Ingredient)" are shown. In Table 5, a formulation of a 10 mg tablet (a coated tablet) and in Table 6, a formulation of a 100 mg tablet (a coated tablet) are illustrated.

TABLE 5

| Material | Purpose | Amount contained (mg) |
| --- | --- | --- |
| The compound | Active ingredient | 12.3 |
| Magnesium oxide | Stabilizer | 10 |
| Anhydrous dibasic calcium phosphate | Diluent | 150.7 |
| D-Mannitol | Diluent | 153 |
| Partially alpha starch | Disintegrant | 20 |
| Crystalline cellulose | Diluent | 16 |
| Hydroxypropylcellulose | Binder | 12 |
| Subtotal | | 374 |
| Croscarmellose sodium | Disintegrant | 20 |
| Sodium stearyl fumarate | Lubricant | 6 |
| Subtotal | | 400 |
| Opadry yellow | Coating agent | 11 |
| Total | | 411 |

TABLE 6

| Material | Purpose | Amount contained (mg) |
|---|---|---|
| The compound | Active ingredient | 122.5 |
| Magnesium oxide | Stabilizer | 10 |
| Anhydrous dibasic calcium phosphate | Diluent | 37.5 |
| Partially alpha starch | Disintegrant | 20 |
| Croscarmellose sodium | Disintegrant | 20 |
| Purified water | Solvent | q.s. |
| Subtotal | | 210 |
| Anhydrous dibasic calcium phosphate | Disintegrant | 136 |
| Croscarmellose sodium | Lubricant | 8 |
| Crystalline cellulose | Diluent | 16 |
| Hydroxypropylcellulose | Disintegrant | 4 |
| Purified water | Solvent | q.s. |
| Subtotal | | 374 |
| Croscarmellose sodium | Disintegrant | 20 |
| Sodium stearyl fumarate | Lubricant | 6 |
| Subtotal | | 400 |
| Opadry yellow | Coating agent | 11 |
| Total | | 411 |

In Tables 5 and 6, "the compound" refers to the crystals (C) of methanesulfonate of 4-(3-chloro-4-(cyclopropylaminocarbonyl)aminophenoxy)-7-methoxy-6-quinolinecarboxamide (the medicament X), and "opadry yellow" refers to a pre-mixed materials consisting of Hydroxypropylmethylcellulose 2910, talc, Macrogol 6000 (molecular weight: 8,000), titanium oxide, and yellow iron sesquioxide in 56.0, 28.0, 10.0, 4.0, and 2.0% (w/w), respectively.

A 10 mg tablet was formulated by the following processes. The active ingredient, magnesium oxide, anhydrous dibasic calcium phosphate, D-mannitol, partially alpha starch, crystalline cellulose, and hydroxypropylcellulose were mixed, and then thereto a suitable amount of purified water was added to prepare pellets. These pellets were dried, and then the size of the pellets was controlled. To the resulting granules, croscarmellose sodium and sodium stearyl fumarate were added and mixed, and a tablet was formed. On the resulting tablet, a film of opadry yellow was coated by a fluidized bed coating technique.

A 100 mg tablet was formulated by the following processes. The active ingredient, magnesium oxide, anhydrous dibasic calcium phosphate, partially alpha starch, and croscarmellose sodium were mixed, and then thereto a suitable amount of purified water was added to prepare pellets. These pellets were dried, and then the size of the pellets was controlled. To the resulting pellets, anhydrous dibasic calcium phosphate, croscarmellose sodium, crystalline cellulose, and hydroxypropylcellulose were added and mixed, and then thereto a suitable amount of purified water was added to prepare granules. These granules were dried, and then the size of the granules was controlled. To the resulting granules, croscarmellose sodium and sodium stearyl fumarate were added and mixed, and a tablet was formed. On the resulting tablet, a film of opadry yellow was coated by a fluidized bed coating technique.

INDUSTRIAL APPLICABILITY

The pharmaceutical composition in accordance with the present invention is highly stable, and hence is clinically useful.

The invention claimed is:

1. A pharmaceutical composition comprising:
    an active ingredient consisting of 4-(3-chloro-4-(cyclopropylaminocarbonyl) aminophenoxy)-7-methoxy-6-quinolinecarboxamide, a salt thereof, or a solvate of either of the foregoing; and
    1-10 w/w % of one or more stabilizer compounds selected from the group consisting of magnesium oxide, calcium oxide, sodium carbonate, disodium hydrogenphosphate, sodium citrate, dipotassium hydrogenphosphate, sodium acetate, sodium hydrogencarbonate, and sodium hydroxide, wherein the 1-10 w/w % represents a percentage of the total weight of the pharmaceutical composition.

2. The pharmaceutical composition according to claim 1, wherein the active ingredient is a hydrochloride, hydrobromide, p-toluenesulfonate, sulfate, methanesulfonate, or ethanesulfonate salt of 4-(3-chloro-4-(cyclopropylaminocarbonyl)aminophenoxy)-7-methoxy-6-quinolinecarboxamide, or a solvate of any one of the foregoing salts.

3. The pharmaceutical composition according to claim 1, wherein the active ingredient is a methanesulfonate salt of 4-(3-chloro-4-(cyclopropylaminocarbonyl)aminophenoxy)-7-methoxy-6-quinolinecarboxamide, or a solvate of the salt.

4. The pharmaceutical composition according to claim 1, wherein the active ingredient is a methanesulfonate salt of 4-(3-chloro-4-(cyclopropylaminocarbonyl)aminophenoxy)-7-methoxy-6-quinolinecarboxamide.

5. The pharmaceutical composition according to claim 1, wherein the active ingredient is a hydrate of a methanesulfonate salt of 4-(3-chloro-4-(cyclopropylaminocarbonyl)aminophenoxy)-7-methoxy-6-quinolinecarboxamide.

6. The pharmaceutical composition according to claim 1, wherein the active ingredient is a dimethyl sulfoxide solvate of a methanesulfonate salt of 4-(3-chloro-4(cyclopropylaminocarbonyl) aminophenoxy)-7-methoxy-6-quinolinecarboxamide.

7. The pharmaceutical composition according to claim 1, wherein the active ingredient is an acetic acid solvate of a methanesulfonate salt of 4-(3-chloro-4-(cyclopropylaminocarbonyl)aminophenoxy)-7-methoxy-6-quinolinecarboxamide.

8. The pharmaceutical composition according to claim 4, wherein the methanesulfonate salt of 4-(3-chloro-4-(cyclopropylaminocarbonyl)aminophenoxy)-7-methoxy-6-quinolinecarboxamide is crystalline and has a powder X-ray diffraction pattern comprising diffraction peaks at diffraction angles (2θ±0.2°) 9.65° and 18.37° that are characteristic of form (A).

9. The pharmaceutical composition according to claim 4, wherein the methanesulfonate salt of 4-(3-chloro-4-(cyclopropylaminocarbonyl)aminophenoxy)-7-methoxy-6-quinolinecarboxamide is crystalline and has a powder X-ray diffraction pattern comprising diffraction peaks at diffraction angles (2θ±0.2°) 5.72° and 13.84° that are characteristic of form (B).

10. The pharmaceutical composition according to claim 5, wherein the hydrate of a methanesulfonate salt of 4-(3-chloro-4-(cyclopropylaminocarbonyl)aminophenoxy)-7-methoxy-6-quinolinecarboxamide is crystalline and has a powder X-ray diffraction pattern comprising diffraction peaks at diffraction angles (2θ±0.2°) 8.02° and 18.14° that are characteristic of form (F).

11. The pharmaceutical composition according to claim 7, wherein the acetic acid solvate of a methanesulfonate salt of 4-(3-chloro-4-(cyclopropylaminocarbonyl)aminophenoxy)-7-methoxy-6-quinolinecarboxamide is crystalline and has a powder X-ray diffraction pattern comprising diffraction peaks at diffraction angles (2θ±0.2°) 9.36° and 12.40° that are characteristic of form (I).

12. The pharmaceutical composition according to claim 8, wherein the crystalline salt is prepared by a process comprising mixing 4-(3-chloro-4-(cyclopropylaminocarbonyl)aminophenoxy)-7-methoxy-6-quinolinecarboxamide, a solvent, and methanesulfonic acid to dissolve the carboxamide.

13. The pharmaceutical composition according to claim 8, wherein the crystalline salt is prepared by a process comprising mixing 4-(3-chloro-4-(cyclopropylaminocarbonyl)aminophenoxy)-7-methoxy-6-quinolinecarboxamide, acetic acid, and methanesulfonic acid to dissolve the carboxamide.

14. The pharmaceutical composition according to claim 9, wherein the crystalline salt is prepared by a process comprising removing acetic acid from a crystalline acetic acid solvate of a methanesulfonate salt of 4-(3-chloro-4-(cyclopropylaminocarbonyl)aminophenoxy)-7-methoxy-6-quinolinecarboxamide having form (I).

15. The pharmaceutical composition according to claim 10, wherein the crystalline salt is prepared by a process comprising mixing together 4-(3-chloro-4-(cyclopropylaminocarbonyl)aminophenoxy)-7-methoxy-6-quinolinecarboxamide, acetic acid, and methanesulfonic acid to dissolve the carboxamide.

16. The pharmaceutical composition according to claim 11, wherein the crystalline salt is prepared by a process comprising mixing together 4-(3-chloro-4-(cyclopropylaminocarbonyl)aminophenoxy)-7-methoxy-6-quinolinecarboxamide, acetic acid, and methanesulfonic acid to dissolve the carboxamide.

17. The pharmaceutical composition of claim 1 wherein the stabilizer compound is magnesium oxide.

18. The pharmaceutical composition of claim 4 wherein the stabilizer compound is magnesium oxide.

19. A process for improving stability of a pharmaceutical composition comprising an active ingredient consisting of 4-(3-chloro-4-(cyclopropylaminocarbonyl)aminophenoxy)-7-methoxy-6-quinolinecarboxamide, a salt thereof, or a solvate of either of the foregoing, comprising adding 1-10 w/w % of one or more stabilizer compounds selected from the group consisting of magnesium oxide, calcium oxide, sodium carbonate, disodium hydrogenphosphate, sodium citrate, dipotassium hydrogenphosphate, sodium acetate, sodium hydrogencarbonate, and sodium hydroxide, wherein the 1-10 w/w % represents a percentage of the total weight of the pharmaceutical composition.

* * * * *

UNITED STATES PATENT AND TRADEMARK OFFICE
CERTIFICATE OF CORRECTION

PATENT NO.         : 9,504,746 B2
APPLICATION NO.    : 13/870507
DATED              : November 29, 2016
INVENTOR(S)        : Hisao Furitsu et al.

It is certified that error appears in the above-identified patent and that said Letters Patent is hereby corrected as shown below:

In the Claims

Column 30
Claim 1, Line 3, delete "(cyclopropylaminocarbonyl) aminophenoxy)" and insert
-- (cyclopropylaminocarbonyl)aminophenoxy) --.

Column 30
Claim 6, Line 35, delete "-4(cyclopropylaminocarbonyl) aminophenoxy)" and insert
-- -4-(cyclopropylaminocarbonyl)aminophenoxy) --.

Signed and Sealed this
Ninth Day of May, 2017

Michelle K. Lee
*Director of the United States Patent and Trademark Office*